US008349991B2

(12) United States Patent
Colton et al.

(10) Patent No.: US 8,349,991 B2
(45) Date of Patent: Jan. 8, 2013

(54) AMPHIPHILIC POLYMERS AND METHODS OF USE THEREOF

(75) Inventors: Clark K. Colton, Newton, MA (US); Arthur Watterson, Nashua, NH (US); Rajesh Kumar, Dract, MA (US); Virinder S. Parmar, Lowell, MA (US); Robert Fisher, West Roxbury, MA (US); Jayant Kumar, Westford, MA (US)

(73) Assignees: Massachusetts Institute of Technology, Cambridge, MA (US); University of Massachusetts Lowell, Lowell, MA (US)

( * ) Notice: Subject to any disclaimer, the term of this patent is extended or adjusted under 35 U.S.C. 154(b) by 178 days.

(21) Appl. No.: 11/405,012

(22) Filed: Apr. 17, 2006

(65) Prior Publication Data
US 2006/0269479 A1 Nov. 30, 2006

Related U.S. Application Data

(60) Provisional application No. 60/672,533, filed on Apr. 19, 2005, provisional application No. 60/672,856, filed on Apr. 20, 2005, provisional application No. 60/732,633, filed on Nov. 3, 2005.

(51) Int. Cl.
*C08G 63/06* (2006.01)
*C08G 63/12* (2006.01)
*C08G 69/08* (2006.01)
*C08G 75/00* (2006.01)
*C08G 63/00* (2006.01)
*C08G 67/00* (2006.01)
*C08G 69/00* (2006.01)
*A61K 47/30* (2006.01)

(52) U.S. Cl. ........ 528/209; 528/331; 528/172; 528/271; 528/272; 514/772.3

(58) Field of Classification Search .................. 528/127, 528/209, 331; 514/772.3
See application file for complete search history.

(56) References Cited

U.S. PATENT DOCUMENTS

| 4,151,051 | A | 4/1979 | Evans |
| 4,151,052 | A | 4/1979 | Goto et al. |
| 4,209,367 | A | 6/1980 | Seko |
| 4,233,436 | A | 11/1980 | Robinson |
| 4,631,330 | A | 12/1986 | Dietz et al. |
| 5,013,830 | A | 5/1991 | Ontsuka et al. |
| 5,149,797 | A | 9/1992 | Pederson |
| 5,220,007 | A | 6/1993 | Pederson |
| 5,256,775 | A | 10/1993 | Froehler |
| 5,366,878 | A | 11/1994 | Pederson |
| 5,403,711 | A | 4/1995 | Walder et al. |
| 5,491,133 | A | 2/1996 | Walder et al. |
| 5,565,350 | A | 10/1996 | Kmiec et al. |
| 5,623,065 | A | 4/1997 | Cook et al. |
| 5,652,355 | A | 7/1997 | Metelev |
| 5,652,356 | A | 7/1997 | Agrawal |
| 5,700,922 | A | 12/1997 | Cook |
| 5,703,126 | A * | 12/1997 | Pavia et al. .................... 514/562 |
| 6,191,255 | B1 | 2/2001 | Seiki et al. |
| 6,210,707 | B1 * | 4/2001 | Papahadjopoulos et al. .. 424/450 |
| 6,217,912 | B1 * | 4/2001 | Park et al. ..................... 424/501 |
| 6,521,736 | B2 * | 2/2003 | Watterson et al. ............ 528/272 |
| 6,610,269 | B1 | 8/2003 | Klaveness |
| 6,716,627 | B2 | 4/2004 | Dobie |
| 6,962,963 | B2 * | 11/2005 | Kumar et al. .................... 528/26 |
| 7,173,102 | B2 * | 2/2007 | DeGrado et al. .............. 528/322 |
| 2002/0099164 | A1 | 7/2002 | Watterson |
| 2003/0144458 | A1 | 7/2003 | Watterson |
| 2003/0181613 | A1 * | 9/2003 | Lele et al. ...................... 526/222 |
| 2004/0022757 | A1 * | 2/2004 | Sawaguchi ................. 424/70.31 |
| 2004/0092449 | A1 | 5/2004 | Ekwuribe |
| 2004/0152176 | A1 | 8/2004 | Kumar |
| 2004/0208844 | A1 * | 10/2004 | Ignatious ................... 424/78.17 |
| 2005/0065290 | A1 | 3/2005 | Shah |
| 2005/0220880 | A1 * | 10/2005 | Lewis et al. .................. 424/486 |
| 2006/0094857 | A1 * | 5/2006 | Kumar et al. ................. 528/220 |

FOREIGN PATENT DOCUMENTS

JP 52-38486 3/1977

OTHER PUBLICATIONS

Jehnichen et al. (Materials Science Forum, vols. 443-444, 2004, p. 223-226).*
Discher et al., "Polymer Vesicles", Scienc vol. 297, Aug. 9, 2002, entire document.
Kumar, R., Chen, M.-S., Parmar, V. S., Samuelson, L. A., Kumar, J., Nicolosi, R., Yoganathan, S., and Watterson, A. C. Supramolecular assemblies based on copolymers of PEG600 and functionalized aromatic diesters for drug delivery applications. Journal of the American Chemical Society. 126: 10640-10644, 2004.
Kumar, R., Shakil, N. A., Chen, M.-H., Parmar, V. S., Samuelson, L. A., Kumar, J., and Watterson, A. C. Chemo-enzymatic synthesis and characterization of novel functionalized amphiphilic polymers. Journal of Macromolecular Science, A39: 1137-1149, 2002.
Thomas, S. R., Gradon, L., Pratsinis, S. E., Pratt, R. G., Fotou, G. P., McGoron, A. J., Podgorski, A. L., and Millard, R. W. Perfluorocarbon Compound Aerosols for Delivery to the Lung as Potential 19F Magnetic Resonance Reporters of Regional Pulmonary pO2. Investigative Radiology, 32: 29-38; 1997.
Folli, S., et al Cancer Research, 54: 2643-2649, 1994.
Kumar, R., Tyagi, R., Parmar, V. S., Samuelson, L. A., Kumar, J., and Watterson, A. C. Biocatalytic "Green" synthesis of PEG-based aromatic polyesters: optimization of the substrate and reaction conditions. Green Chemistry, 6: 516-520, 2004.
Kumar, R., Tyagi, R., Parmar, V. S., Samuelson, L. A., and Watterson, A. C. *Candida antarctica* lipase B catalyzed copolymerizations of non-proteinogenic amino acids and poly(ethylene glycol) to generate novel functinalized polyesters. Journal of Macromolecular Science: Pure and Applied Chemistry, A40: 1283, 2003.

(Continued)

*Primary Examiner* — Liam Heincer
(74) *Attorney, Agent, or Firm* — Fish & Richardson P.C.

(57) ABSTRACT

The present invention relates to amphiphilic polymers, and micelles and compositions comprising the same, and their use in a variety of biological settings, including imaging, targeting drugs, or a combination thereof for diagnostic and therapeutic purposes.

41 Claims, 23 Drawing Sheets

OTHER PUBLICATIONS

Tyagi, R., Kumar, R., Parmar, V. S., Samuelson, L. A., Kumar, J., and Watterson, A. C. Biocatalytic routes for the synthesis of amino acid containing amphiphilic copolymers for drug delivery applications. Polymer Preprint, 44: 778, 2003.

Sharma, S. K., Sharma, A. K., Kumar, R., Parmar, V. S., Kumar, J., Samuelson, L. A., and Watterson, A. C. Synthesis of amino functionalized amphiphilic copolymers as potential gene delivery carriers. Polymer Preprint, 44: 791, 2003.

Sharma, S. K., Sharma, A. K., Parmar, V. S., Kumar, J., Samuelson, L. A., and Watterson, A. C. Synthesis of Amphiphilic Guanylated Polymers as potntial Gene Delivery Carriers. Journal of Macromolecular Science: Pure and Applied Chemistry, A41: 1459, 2004.

Chen, M. H., Kumar, R., Yang, K., Parmar, V. S., Samuelson, L. A., and Watterson, A. C. Studies on the supramolecular organization of amphiphilic copolymers into nano-micelles by light scattering techniques. Polymer Preprints, 44: 1199-1200, 2003.

Becker, A., et al. Nature Biotechnology, 19: 327-331, 2001.

Kimura, et al. (Magnetic Resonance Imaging, 22: 855-860, 2004).

Busse, L. J., et al. Medical Physics, 13: 518-524, 1986.

Sharma, S. K., et al., Chemical Communication 23: 2689-2691 2004.

Josephson et al., "Near-Infrared Fluorescent Nanoparticles as Combined MR/Optical Imaging Probes", Bioconjugate Chem. 13(3):554-560, 2002.

Kircher et al., "Imaging of enzyme activity using dual wavelength optical reporters". Mol Imaging. 1(2):89-95, 2002.

Laukemper-Ostendorf et al., "F-MRI of perflubron for measurement of oxygen partial pressure in porcine lungs during partial liquid ventilation", Magnetic Resonance in Medicine, 47:82-89, 2002.

Noth et al., "In vivo determination of the partial oxygen pressure in perfluorocarbon-loaded alginate capsules implanted into the peritoneal cavity and different tissues", Magnetic Resonance in Medicine 42(6):1039-47, 1999.

Roberts, M. J., et al. "Chemistry for peptide and protein PEGylation" Advanced Drug Delivery Reviews: 54:459-476, 2002.

Waggoner A., "Covalent labeling of proteins and nucleic acids with fluorophores, Methods Enzymol". 1995;246:362-73. Department of Biological Sciences, Carnegie Mellon University, Pittsburgh.

Williams et al., "Mapping of oxygen tension and cell distribution in a hollow-fiber bioreactor using magnetic resonance imaging". Biotechnol Bioeng 56:56-61, 1997.

Supplementary European Search Report, EP 06750510, Feb. 21, 2011.

Watterson Arthur C. et al.: "Indo-U.S. collaborative studies on biocatalytic generation of novel molecular architectures", Pure and Applied Chemistry, vol. 77, No. 1, Jan. 2005.

Moore A et al: "In Vivo Targeting of Underglycosylated MUC-1 Tumor Antigen Using a Multimodal Imaging Probe", Cancer Research 20040301 US, vol. 64, No. 5, Mar. 1, 2004, pp. 1821-1827.

* cited by examiner

Synthetic scheme for preparation of basic copolymer structures

R = groups for the amino acids:
arginine, alanine, glycine, 2-fluorophenyl glycine R' = fluorocarbon and hydrocarbon groups R = groups for the amino acids:
arginine, alanine, glycine, 2-fluorophenyl glycine R' = fluorocarbons or hydrocarbons (95%)

Perfluorocarbon side chains

Encapsulated perfluorocarbon cargo

Micelle nanoparticles with perfluorocarbon side chains and cargo

HGVTSAPDTRPAPGSTAPPA

IMMUNODOMINANT REGION TARGETED BY EPPT PEPTIDE

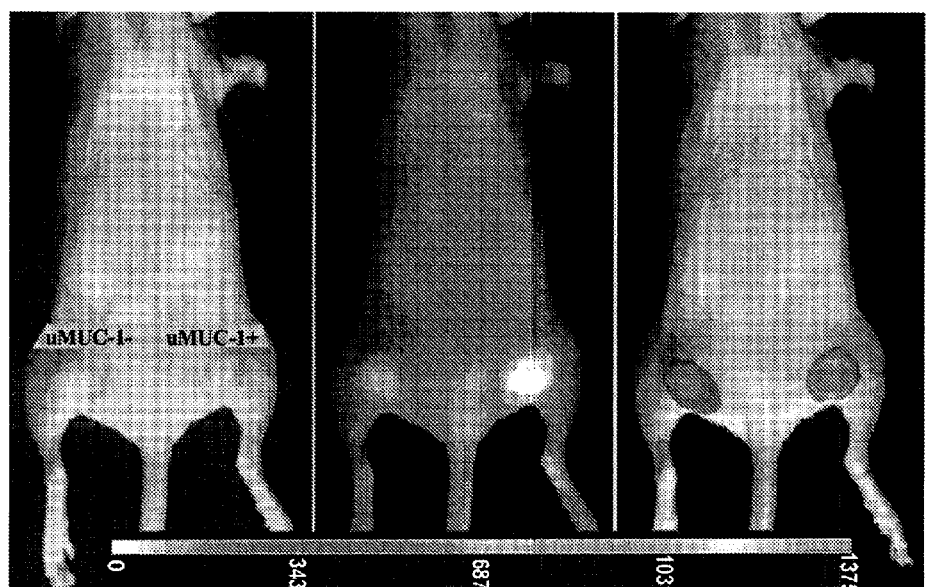
FIG. 8B
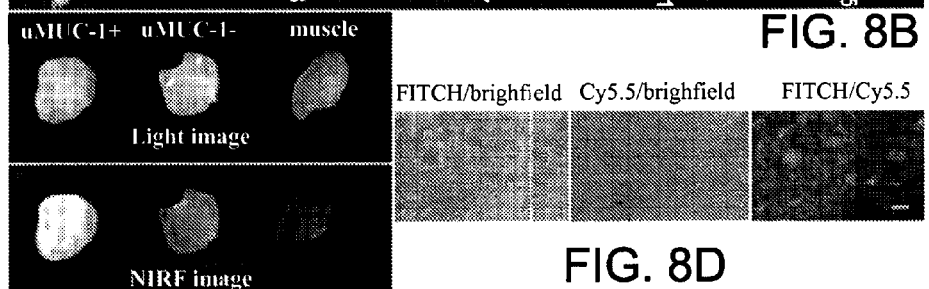
FIG. 8C
FIG. 8D

First Stage of Synthesis Enzymatic Polymerization $R_2 = (CF_2)_8CF_3$ , $(CF_2)_6CF_3$ , $(CF_2)_3CF_3$ $R_2 = CH_2OCH_2(CF)_8CF_3$ , $CH_2OCH_2(CF_2)_6CF_3$ , $CH_2OCH_2(CF_2)_4CF_3$ $R_2 = CH_2OCH_2CH_2(CF_2)_{11}CF_3$ Alternations for perfluorocarbon side chains

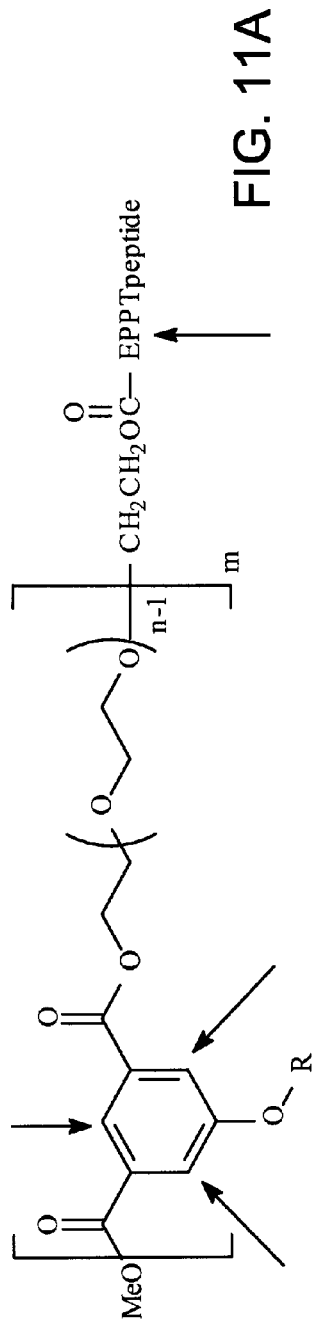
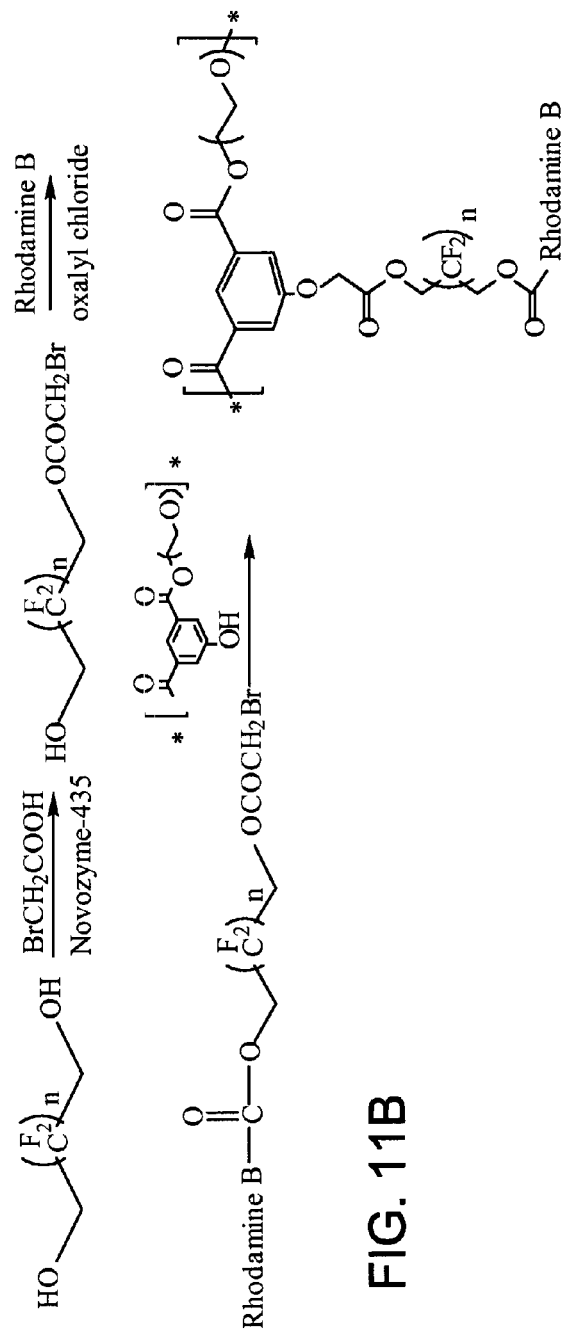
FIG. 11A
FIG. 11B

SEQUENCE LISTING

<160> NUMBER OF SEQ ID NOS: 5

<210> SEQ ID NO 1
<211> LENGTH: 15
<212> TYPE: PRT
<213> ORGANISM: Homo sapiens

<400> SEQUENCE: 1

Tyr Cys Ala Arg Glu Pro Pro Thr Arg Thr Phe Ala Tyr Trp Gly
1               5                   10                  15

<210> SEQ ID NO 2
<211> LENGTH: 24
<212> TYPE: PRT
<213> ORGANISM: Homo sapiens

<400> SEQUENCE: 2

Tyr Cys Ala Cys Met Ala Arg Glu Pro Pro Thr Arg Thr Phe Ala Tyr
1               5                   10                  15

Trp Gly Lys Phe Ile Thr Cys Lys
            20

<210> SEQ ID NO 3
<211> LENGTH: 21
<212> TYPE: DNA
<213> ORGANISM: Homo sapiens

<400> SEQUENCE: 3
acaggttctg gtcatgcaag c                                            21

<210> SEQ ID NO 4
<211> LENGTH: 26
<212> TYPE: DNA
<213> ORGANISM: Homo sapiens

<400> SEQUENCE: 4
ctcacagcat tcttctcagt agagct                                       26

<210> SEQ ID NO 5
<211> LENGTH: 29
<212> TYPE: DNA
<213> ORGANISM: Homo sapiens

<400> SEQUENCE: 5
tggagaaaag gagacttcgg ctacccaga                                    29

AMPHIPHILIC POLYMERS AND METHODS OF USE THEREOF

CROSS-REFERENCE TO RELATED APPLICATIONS

This Application claims the benefit of U.S. Provisional Application Ser. No. 60/672,533, filed Apr. 19, 2005, U.S. Provisional Application Ser. No. 60/672,856, filed Apr. 20, 2005 and U.S. Provisional Application Ser. No. 60/732,633 filed Nov. 3, 2005, all of which are hereby incorporated by reference in their entirety.

FIELD OF THE INVENTION

This invention provides amphiphilic polymers, processes for producing the same and methods of use thereof. Polymers of this invention may be used in diagnostics and imaging, as well as treatments of diseases and disorders including cancer and gene therapy applications.

BACKGROUND OF THE INVENTION

One of the most fundamental limitations to reducing mortality due to a number of diseases, including cancer, is the fact that current medical imaging techniques, such as CT and MRI, provide detailed anatomical snapshots of the body but fail to provide accurate, basic information necessary to manage the patient's disease optimally.

The limitations are manifested in several ways, such as for example in cancer: (1) Small primary tumors go undetected. Even under the best conditions, tumors smaller than 2 mm (roughly 500,000 cells) cannot be seen. (2) Metastatic disease is grossly underdiagnosed, and patients with negative scans for metastases at initial presentation routinely go on to develop, and die, from metastatic cancer. (3) Treatment response to therapy is poorly measured. "Measurable disease" is absent after surgical excision of many tumors. The standard of care is to blindly treat with chemotherapy selected by convention using prior retrospective studies and to consider this treatment a success or failure only in retrospect (e g., failure is when a relapse occurs in less than 5 years). Residual metastatic disease can expand undetected. When metastatic disease leads to a tumor that is large enough to be detected (stage 4), it is often too late for anything but a modest extension in patient lifetime with available treatments.

How can conventional imaging be so far off the mark? One reason is that conventional radiologic approaches produce their images based upon bulk structural and anatomical features of the tissue. For example, the image displayed in MRI is that of protons in water or fat as modified by relative concentration and environment. The degree to which, for example, a tumor can be visualized on conventional CT or MRI is merely a function of the ability of that tumor to differentially scatter, absorb, or emit radiation as compared to the surrounding tissue and inherent background noise. It is not surprising that this signal has little sensitivity and specificity for the detection of a tumor.

The signal can be enhanced, however, through the use of targeted probes. Supramolecular assemblies that can be made to form nanospherical structures for carrying contrast agent, such as liposomes and polymer micelles, offer potential for improving various imaging modalities. Results with such liposomes, however, have essentially been disappointing.

Moreover, equally frustrating is a lack of versatile delivery systems for therapeutics, targeted delivery, and a reliable means of proper dosing and tissue distribution of the therapeutic.

SUMMARY OF THE INVENTION

The invention provides, in one embodiment, an amphiphilic polymer, characterized by the structure of the general formula I:

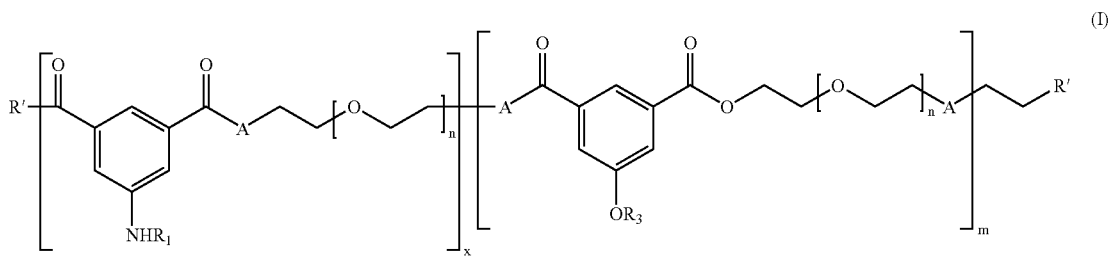

wherein

R is a hydroxyl (OH), O-alkyl, O-Acyl, O-Activating group, SH, S-alkyl, or an acid activating group such as halogen (Cl, Br, I), O-vinyl, O-allyl, O-aryl, OCOalkyl, OCOaryl, $OCH_2CF_3$, $NH_2$, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety;

R' is OH, $NH_2$, SH;

each $R_1$ group is, independently,

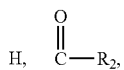

a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a perfluorocarbon, a perfluorocarbon-$R_4$, a perfluorocarbon-$OR_4$,

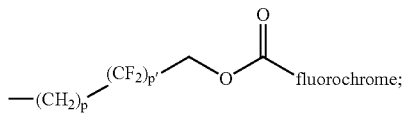

each $R_2$ group is, independently, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a perfluorocarbon, a perfluorocarbon-$R_4$, a perfluorocarbon-$OR_4$,

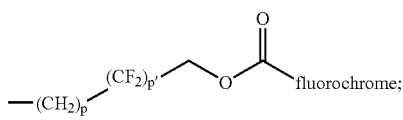

each $R_3$ group is, independently

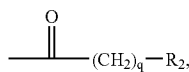

a hydrogen, a hydroxyl (OH), O-alkyl, SH, S-alkyl, or an acid activating group such as halogen (Cl, Br, I), O-vinyl, O-allyl, O-aryl, OCOalkyl, OCOaryl, $OCH_2CF_3$, $NH_2$, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety;

each $R_4$ group is, independently, an alkyl group, an alkylene group, a carboxylate group, a carboxylic acid group, an amino group, an ammonium group, an alkoxyl group, a hydroxyl group or another nitrogen, oxygen or sulfur-containing group;

each A group is, independently, O, NH, S, a fluorochrome,

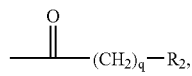

an indole-containing compound, an antibody or antibody fragment, a peptide, an oligonucleotide, a drug, a ligand for a biological target, an immunoconjugate, a chemomimetic functional group, a glycolipid, a labeling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, an acyl group, an aryl group, a linear or branched alkenyl group, a linear or branched alkyl group, wherein said alkyl, alkenyl or aryl group is substituted with a perfluorocarbon, perfluorocarbon-$R_4$, perfluorocarbon-$OR_4$, perfluorocarbon-$OR_4$, or

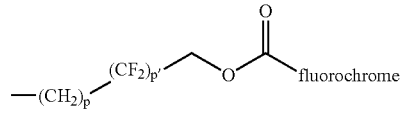

n, m, p, p' and x are integers; and q is an integer between 0-10.

In another embodiment, this invention provides a polymer is characterized by the structure of the general formula II:

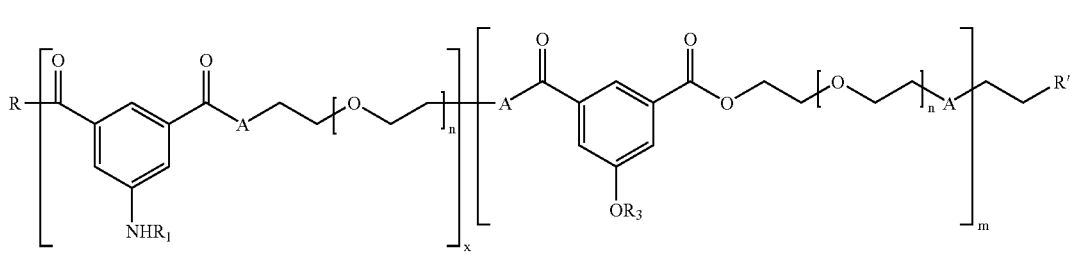

wherein R'=OH, $NH_2$, SH;
R=OH, OAlkyl, OAryl, OAcyl, OActivating group;
$R_1$ and $R_3$ are H; and
A=O, NH, S.

In another embodiment, this invention provides an amphiphilic polymer, characterized by the structure of the general formula III:

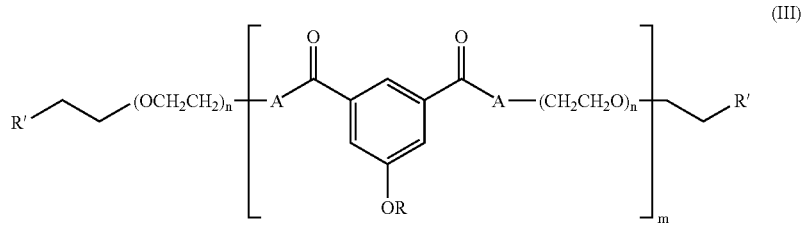

wherein
each R group is, independently: a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, an acyl group, an aryl group, a linear or branched alkenyl group, a linear or branched alkyl group, wherein said alkyl, alkenyl or aryl group is substituted with a perfluorocarbon, perfluorocarbon-$R_4$, perfluorocarbon-$OR_4$, or

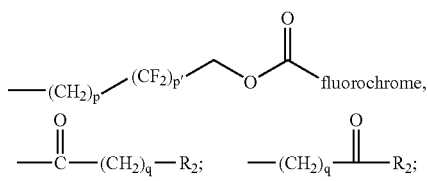

each R' group is, independently, a hydrogen, a hydroxyl (OH), O-alkyl, SH, S-alkyl, or an acid activating group a labeling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, an acyl group, an aryl group, a linear or branched alkenyl group, a linear or branched alkyl group, wherein said alkyl, alkenyl or aryl group is substituted with a perfluorocarbon, perfluorocarbon-$R_4$, perfluorocarbon-$OR_4$, or

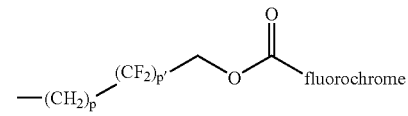

p and p' are integers;
n is at least 1; and
m is at least 1.

In another embodiment, this invention provides an amphiphilic polymer, characterized by the structure of the general formula IV:

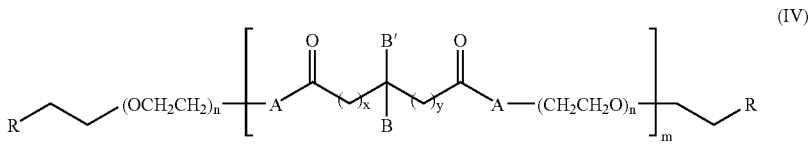

such as halogen (Cl, Br, I), O-vinyl, O-allyl, O-aryl, OCOalkyl, OCOaryl, OCH$_2$CF$_3$NH$_2$, SH, an acyl group, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, or

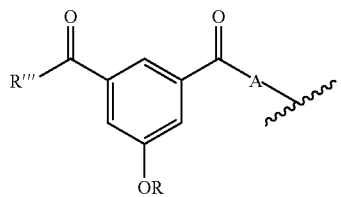

wherein
R''' is a hydroxyl group, an alkoxyl group or a primary or secondary amino group, O activating group, SH and S-alkyl;
$R_4$ is independently an alkyl group, an alkylene group, a carboxylate group, a carboxylic acid group, and amino group, an ammonium group, an alkoxyl group, a hydroxyl group or another nitrogen, oxygen or sulfur-containing group, a halogen;
A is a fluorochrome, an indole-containing compound, an antibody or antibody fragment, a peptide, an oligonucleotide, a drug, a ligand for a biological target, an immunoconjugate, a chemomimetic functional group, a glycolipid, wherein
each R group, independently, is a hydroxyl (OH), OCH$_2$CF$_3$, NH$_2$, SH, S, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, a halogen, an aryl group, a linear or branched alkenyl group, a linear or branched alkyl group, wherein said alkyl, alkenyl or aryl group is substituted with a perfluorocarbon, perfluorocarbon-$R_4$, perfluorocarbon-$OR_4$, or

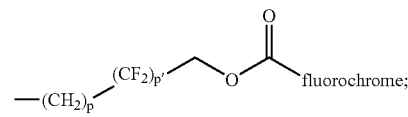

$R_4$ is independently an alkyl group, an alkylene group, a carboxylate group, a carboxylic acid group, and amino group, an ammonium group, an alkoxyl group, a hydroxyl group or another nitrogen, oxygen or sulfur-containing group
B or B' is, independently: alkyl, substituted alkyl, aryl, substituted aryl, OH, NH$_2$, OR, NHR;
x=0-6;
y=0-6;
p, p' are integers;
n is at least 1; and
m is at least 1.

In another embodiment, this invention provides an amphiphilic polymer, characterized by the structure of the general formula V:

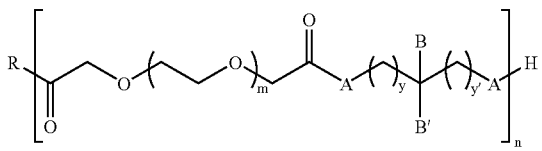

wherein
R is a hydroxyl (OH), O-alkyl, SH, S-alkyl, or an acid activating group such as halogen (Cl, Br, I), O-vinyl, O-allyl, O-aryl, OCOalkyl, OCOaryl, $OCH_2CF_3NH_2$, NH, SH, an acyl group, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, an aryl group, a linear or branched alkenyl group, a linear or branched alkyl group, wherein said alkyl, alkenyl or aryl group is substituted with a perfluorocarbon, perfluorocarbon-$R_4$, perfluorocarbon-$OR_4$, or

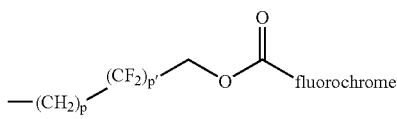

$R_4$ is independently an alkyl group, an alkylene group, a carboxylate group, a carboxylic acid group, and amino group, an ammonium group, an alkoxyl group, a hydroxyl group or another nitrogen, oxygen or sulfur-containing group A is, independently: O, S or NH B or B' is, independently: alkyl, substituted alkyl, aryl, substituted aryl, OH, $NH_2$, OR, NHR;

n is an integer from 1-10,000

Each m, independently, is an integer from 1-1,000;

y or y' independently, is an integer from 1-10.

In another embodiment, this invention provides an amphiphilic polymer, characterized by the structure of the general formula VI:

(VI)

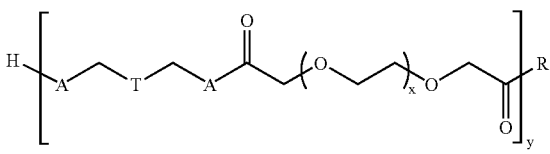

wherein
R is a hydroxyl (OH), O-alkyl, SH, S-alkyl, or an acid activating group such as halogen (Cl, Br, I), O-vinyl, O-allyl, O-aryl, OCOalkyl, OCOaryl, $OCH_2CF_3NH_2$, NH, SH, an acyl group, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, an aryl group, a linear or branched alkenyl group, a linear or branched alkyl group, wherein said alkyl, alkenyl or aryl group is substituted with a perfluorocarbon, perfluorocarbon-$R_4$, perfluorocarbon-$OR_4$, or

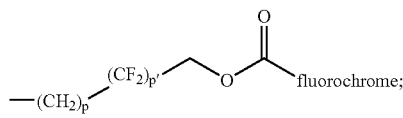

$R_4$ is independently an alkyl group, an alkylene group, a carboxylate group, a carboxylic acid group, and amino group, an ammonium group, an alkoxyl group, a hydroxyl group or another nitrogen, oxygen or sulfur-containing group;

T, independently is:

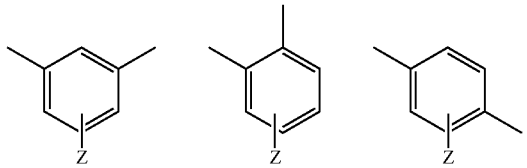

z is, independently, a halogen, a nitro group, a hydroxy group, an amino group, an alkyl group, a substituted alkyl group, an aryl group, a substituted aryl group, wherein said substituted alkyl or aryl group is substituted with a perfluorocarbon, perfluorocarbon-$R_4$, perfluorocarbon-$OR_4$, or

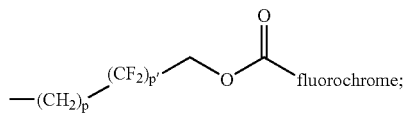

A is, independently O, S, NH;

p, p' are integers;

each x, independently, is an integer from 1-1000; and y is an integer from 1-10,000.

In another embodiment, this invention provides an amphiphilic polymer, characterized by the structure of the general formula VII:

(VII)

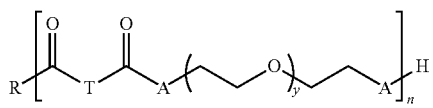

wherein
R is a hydroxyl (OH), O-alkyl, SH, S-alkyl, or an acid activating group such as halogen (Cl, Br, I), O-vinyl, O-allyl, O-aryl, OCOalkyl, OCOaryl, $OCH_2CF_3NH_2$, NH, SH, an acyl group, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, an aryl group, a linear or branched alkenyl group, a linear or branched alkyl group, wherein said alkyl, alkenyl or aryl group is substituted with a perfluorocarbon, perfluorocarbon-$R_4$, perfluorocarbon-$OR_4$, or

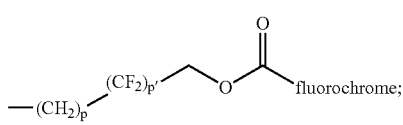

$R_4$ is independently an alkyl group, an alkylene group, a carboxylate group, a carboxylic acid group, and amino group, an ammonium group, an alkoxyl group, a hydroxyl group or another nitrogen, oxygen or sulfur-containing group;

T, independently is:

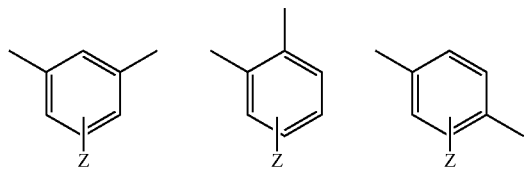

z is, independently, H, alkyl, aryl, $NH_2$, NH-alkyl, NH-acyl, NH-aryl, OH, O-acyl, O-alkyl, O-aryl, a halogen, a nitro group, a hydroxy group, a substituted alkyl group, a substituted aryl group, wherein said substituted alkyl or aryl group is substituted with a perfluorocarbon, perfluorocarbon-$OR_4$ or

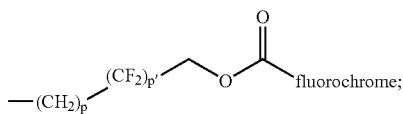

A is, independently O, S, NH;
p, p' are integers;
each y, independently, is an integer from 1-1000; and
n is an integer from 1-10,000.

In another embodiment, this invention provides a composition or a micelle comprising a polymer of this invention.

In another embodiment, this invention provides a process for producing an amphiphilic polymer comprising perfluorocarbons, the process comprising the steps of:
  contacting a dialkyl 5-hydroxy-isophthalate, a dialkyl 5-alkoxy-isophthalate, a dialkyl 5-amino-isophthalate, any derivative thereof or any combination thereof with a polyethylene glycol to form an amphiphilic copolymer; and
  linking a perfluorocarbons to said amphiphilic copolymer, thereby being a process for producing amphiphilic polymers comprising perfluorocarbons.

In another embodiment, this invention provides a method of imaging a cell, the method comprising the steps of contacting a cell with an amphiphilic polymer of this invention and imaging said cell, whereby said polymer enables the imaging of said cell.

In another embodiment, this invention provides a method of targeted delivery of at least one agent in a subject comprising the steps of administering to said subject an amphiphilic polymer of this invention, wherein said polymer comprises said agent and a targeting agent.

In another embodiment, this invention provides a method for detecting neoplastic cells in a subject, comprising contacting a cell in, or a cell derived from said subject with an effective tumor-detecting amount of an amphiphilic polymer of this invention, wherein said polymer comprises a targeting moiety specific for neoplastic cells; and detecting any of said polymer associated with neoplastic cells present in said subject.

BRIEF DESCRIPTION OF THE DRAWINGS

FIGS. 11A-11C depict structures of the polymers with various substituents. Structure of nanospheres and positions available for iodination (11A). A scheme for the fluorescent labeling of perfluorinated side chains (11B). A representative polymer showing possible sites for radioiodination, and for fluorophore and perfluorocarbon attachment (11C).

DETAILED DESCRIPTION OF THE INVENTION

Figure 1:
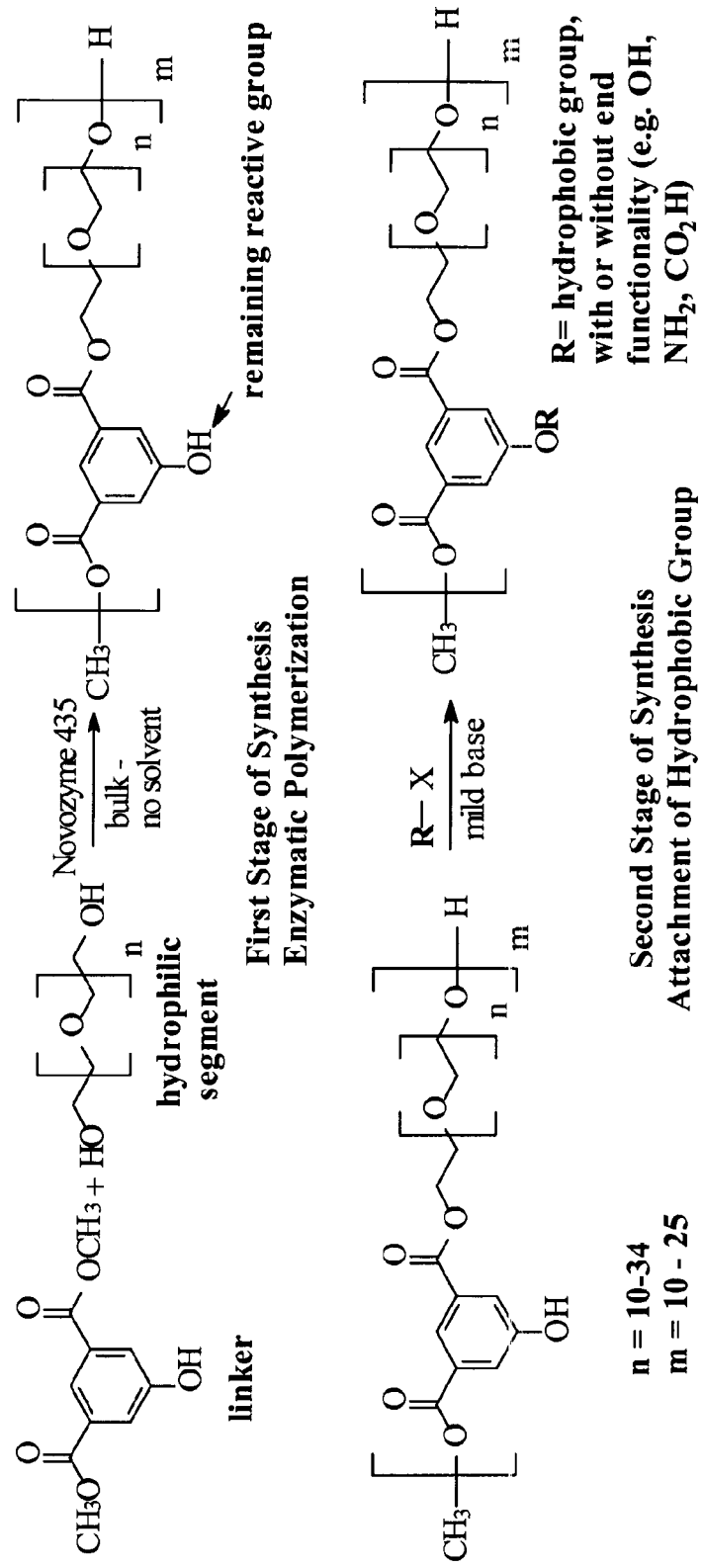
FIG. 1 depicts a synthetic scheme for the preparation of a basic copolymer structure.

The invention provides, in one embodiment, an amphiphilic polymer, characterized by the structure of the general formula I:

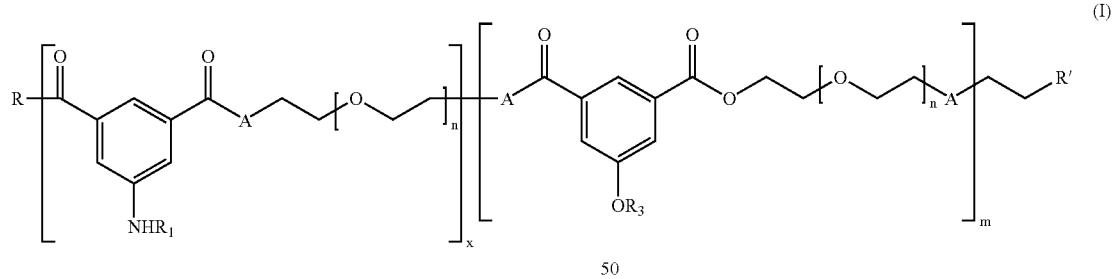

wherein
R is a hydroxyl (OH), O-alkyl, O-Acyl, O-Activating group, SH, S-alkyl, or an acid activating group such as halogen (Cl, Br, I), O-vinyl, O-allyl, O-aryl, OCOalkyl, OCOaryl, OCH$_2$CF$_3$, NH$_2$, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an. antimetabolite, a microtubule inhibitor, a radioactive material, a targeting moiety;
R' is OH, NH$_2$, SH, OR", NHR", SR";
Where R" is a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety; each R$_1$ group is, independently,

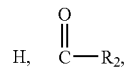

a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a perfluorocarbon, a perfluorocarbon-R$_4$, a perfluorocarbon-OR$_4$,

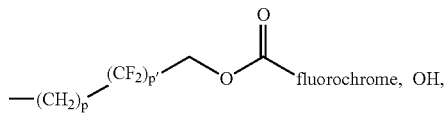

NH$_2$, NH, S, SH, O-alkyl;
each R$_2$ group is, independently, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a perfluorocarbon, a perfluorocarbon-R$_4$, a perfluorocarbon-OR$_4$,

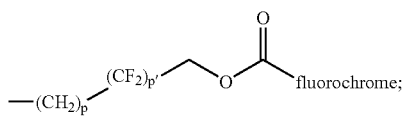

each R$_3$ group is, independently,

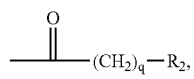

a hydrogen, a hydroxyl (OH), O-alkyl, SH, S-alkyl, or an acid activating group such as halogen (Cl, Br, I), O-vinyl, O-allyl, O-aryl, OCOalkyl, OCOaryl, OCH$_2$CF$_3$, NH$_2$, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety;

each $R_4$ group is, independently, an alkyl group, an alkylene group, a carboxylate group, a carboxylic acid group, an amino group, an ammonium group, an alkoxyl group, a hydroxyl group or another nitrogen, oxygen or sulfur-containing group, a halogen;

each A group is, independently, O, NH, S, a fluorochrome,

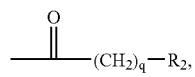

an indole-containing compound, an antibody or antibody fragment, a peptide, an oligonucleotide, a drug, a ligand for a biological target, an immunoconjugate, a chemomimetic functional group, a glycolipid, a labeling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, an acyl group, an aryl group, a linear or branched alkenyl group, a linear or branched alkyl group, wherein said alkyl, alkenyl or aryl group is substituted with a perfluorocarbon, perfluorocarbon-$R_4$, perfluorocarbon-$OR_4$, perfluorocarbon-$OR_4$, or

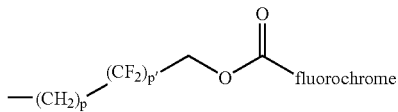

n, m, p, p' and x are integers; and
q is an integer between 0-10.

In another embodiment, this invention provides a polymer is characterized by the structure of the general formula II:

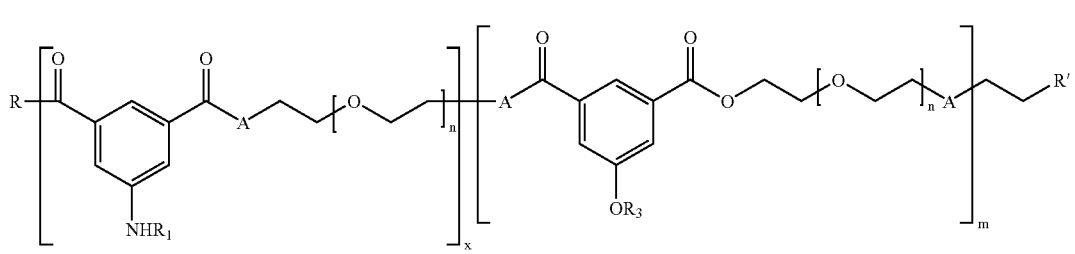

wherein R'=OH, $NH_2$, SH, OAlkyl, OAryl, OAcyl, OActivating group;
R=OH, $NH_2$, SH, OAlkyl, OAryl, OAcyl, OActivating group;
$R_1$=H;
$R_3$=H, a hydroxyl (OH), O-alkyl, SH, S-alkyl, or an acid activating group such as halogen (Cl, Br, I), O-vinyl, O-allyl, O-aryl, OCOalkyl, OCOaryl, $OCH_2CF_3$, $NH_2$, (a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety); and
A=O, NH, S.

In another embodiment, this invention provides an amphiphilic polymer, characterized by the structure of the general formula III:

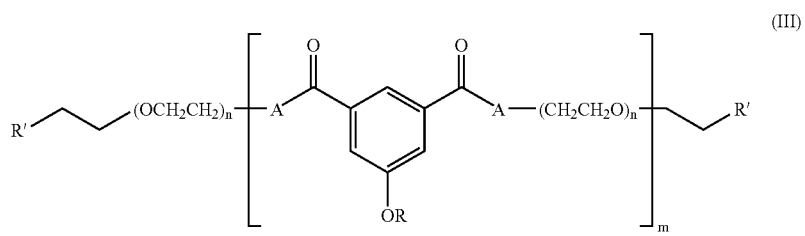

wherein
each R group is, independently: a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, an acyl group, an aryl group, a linear or branched alkenyl group, a linear or branched alkyl group, wherein said alkyl, alkenyl or aryl group is substituted with a perfluorocarbon, perfluorocarbon-$R_4$, perfluorocarbon-$OR_4$, or

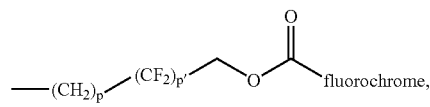

-continued

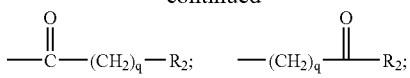

each R' group is, independently, a hydrogen, a hydroxyl (OH), O-alkyl, SH, S-alkyl, or an acid activating group such as halogen (Cl, Br, I), O-vinyl, O-allyl, O-aryl, OCOalkyl, OCOaryl, OCH$_2$CF$_3$NH$_2$, SH, an acyl group, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, orOR", NHR", SR"

wherein R" is a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety;

wherein R'" is a hydroxyl group, an alkoxyl group or a primary or secondary amino group, O activating group, SH and S-alkyl;

R$_2$ is, independently, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a perfluorocarbon, a perfluorocarbon-R$_4$, a perfluorocarbon-OR$_4$,

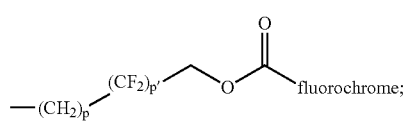

R$_4$ is independently an alkyl group, an alkylene group, a carboxylate group, a carboxylic acid group, and amino group, an ammonium group, an alkoxyl group, a hydroxyl group or another nitrogen, oxygen or sulfur-containing group, a halogen;

A is a fluorochrome, an indole-containing compound, an antibody or antibody fragment, a peptide, an oligonucleotide, a drug, a ligand for a biological target, an immunoconjugate, a chemomimetic functional group, a glycolipid, a labeling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, an acyl group, an aryl group, a linear or branched alkenyl group, a linear or branched alkyl group, wherein said alkyl, alkenyl or aryl group is substituted with a perfluorocarbon, perfluorocarbon-R$_4$, perfluorocarbon-OR$_4$, or

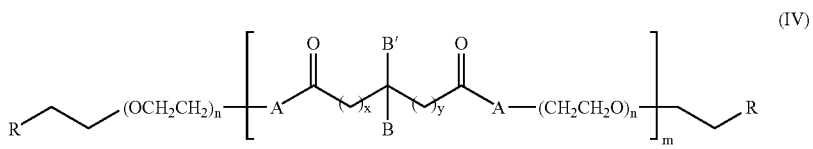

p and p' are integers;
n is at least 1; and
m is at least 1.

In another embodiment, this invention provides an amphiphilic polymer, characterized by the structure of the general formula IV:

$$R\diagdown(OCH_2CH_2)_n-\left[A-\underset{O}{\overset{O}{\|}}C-(\overset{B'}{\underset{B}{C}})_x(CH_2)_y-\underset{O}{\overset{O}{\|}}C-A-(CH_2CH_2O)_n\right]_m R \quad (IV)$$

wherein
each R group, independently, is a hydroxyl (OH), OCH$_2$CF$_3$, NH$_2$, SH, S, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, a halogen, an aryl group, a linear or branched alkenyl group, a linear or branched alkyl group, wherein said alkyl, alkenyl or aryl group is substituted with a perfluorocarbon, perfluorocarbon-R$_4$, perfluorocarbon-OR$_4$, or

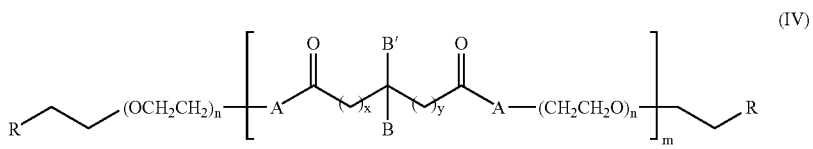

R$_4$ is independently an alkyl group, an alkylene group, a carboxylate group, a carboxylic acid group, and amino group, an ammonium group, an alkoxyl group, a hydroxyl group, a halogen or another nitrogen, oxygen or sulfur-containing group B or B' is, independently: alkyl, substituted alkyl, aryl, substituted aryl, OH, NH$_2$, OR$_1$, NHR$_1$; OCOR$_1$, NHCOR$_1$ Where R$_1$ is alkyl, substituted alkyl, aryl, substituted aryl, wherein the said alkyl or aryl group is either perfluorinated or substituted with perfluorinated compound.

x=0-10;
y=0-10;
p, p' are integers;
n is at least 1; and
m is at least 1.

In another embodiment, this invention provides an amphiphilic polymer, characterized by the structure of the general formula V:

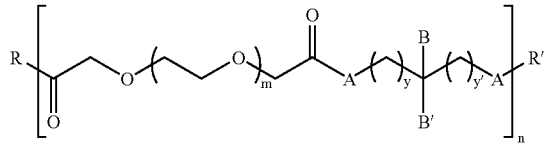
(V)

wherein
R is a hydroxyl (OH), O-alkyl, SH, S-alkyl, or an acid activating group such as halogen (Cl, Br, I), O-vinyl, O-allyl, O-aryl, OCOalkyl, OCOaryl, OCH$_2$CF$_3$NH$_2$, NH, SH, an acyl group, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, an aryl group, a linear or branched alkenyl group, a linear or branched alkyl group, wherein said alkyl, alkenyl or aryl group is substituted with a perfluorocarbon, perfluorocarbon-R$_4$, perfluorocarbon-OR$_4$, or

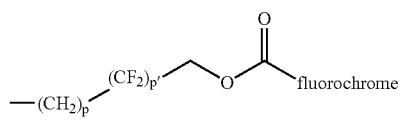

R' is hydrogen, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, an aryl group, a linear or branched alkenyl group, a linear or branched alkyl group, wherein said alkyl, alkenyl or aryl group is substituted with a perfluorocarbon, perfluorocarbon-R$_4$, perfluorocarbon-OR$_4$;

R$_4$ is independently an alkyl group, an alkylene group, a carboxylate group, a carboxylic acid group, and amino group, an ammonium group, an alkoxyl group, a hydroxyl group or another nitrogen, oxygen or sulfur-containing group A is, independently: O, S or NH B or B' is, independently, alkyl, substituted alkyl, aryl, substituted aryl, OH, NH$_2$, OR$_1$, NHR$_1$; Where R$_1$ is alkyl, substituted alkyl, aryl, substituted aryl, wherein the said alkyl or aryl group is either perfluorinated or substituted with perfluorinated compound, NHR;

n is an integer from 1-10,000

Each m, independently, is an integer from 1-1,000;

y or y' independently, is an integer from 1-10.

In another embodiment, this invention provides an amphiphilic polymer, characterized by the structure of the general formula VI:

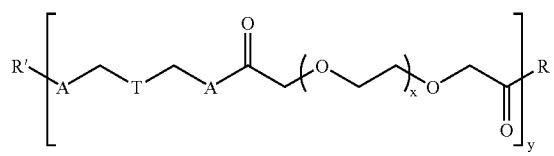
(VI)

wherein
R is a hydroxyl (OH), O-alkyl, SH, S-alkyl, or an acid activating group such as halogen (Cl, Br, I), O-vinyl, O-allyl, O-aryl, OCOalkyl, OCOaryl, OCH$_2$CF$_3$NH$_2$, NH, SH, an acyl group, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, an aryl group, a linear or branched alkenyl group, a linear or branched alkyl group, wherein said alkyl, alkenyl or aryl group is substituted with a perfluorocarbon, perfluorocarbon-R$_4$, perfluorocarbon-OR$_4$, or

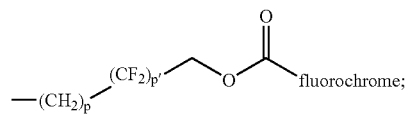

R' is hydrogen, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, an aryl group, a linear or branched alkenyl group, a linear or branched alkyl group, wherein said alkyl, alkenyl or aryl group is substituted with a perfluorocarbon, perfluorocarbon-R$_4$, perfluorocarbon-OR4.

R$_4$ is independently an alkyl group, an alkylene group, a carboxylate group, a carboxylic acid group, and amino group, an ammonium group, an alkoxyl group, a hydroxyl group or another nitrogen, oxygen or sulfur-containing group;

T, independently is:

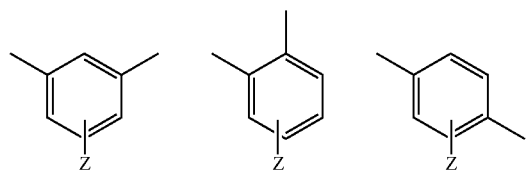

z is, independently, a halogen, a nitro group, a hydroxy group, an amino group, an alkyl group, a substituted alkyl group, an aryl group, a substituted aryl group, wherein said substituted alkyl or aryl group is substituted with a perfluorocarbon, perfluorocarbon-R$_4$, perfluorocarbon-OR$_4$, or

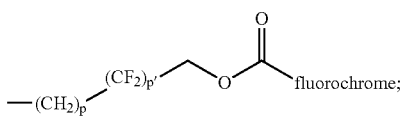

A is, independently O, S, NH;

p, p' are integers;

each x, independently, is an integer from 1-1000; and y is an integer from 1-10,000.

In another embodiment, this invention provides an amphiphilic polymer, characterized by the structure of the general formula VII:

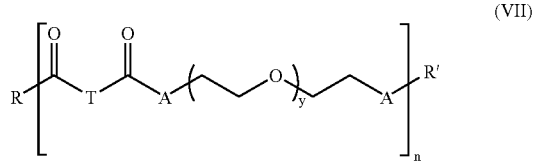

wherein

R is a hydroxyl (OH), O-alkyl, SH, S-alkyl, or an acid activating group such as halogen (Cl, Br, I), O-vinyl, O-allyl, O-aryl, OCOalkyl, OCOaryl, $OCH_2CF_3NH_2$, NH, SH, an acyl group, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, an aryl group, a linear or branched alkenyl group, a linear or branched alkyl group, wherein said alkyl, alkenyl or aryl group is substituted with a perfluorocarbon, perfluorocarbon-$R_4$, perfluorocarbon-$OR_4$, or

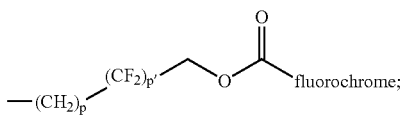

R' is hydrogen, a fluorochrome, an indole-containing compound, an antibody or antibody fragment, a peptide, an oligonucleotide, a drug, a ligand for a biological target, an immunoconjugate, a chemomimetic functional group, a glycolipid, a labelling agent, an enzyme, a metal ion chelate, an enzyme cofactor, a cytotoxic compound, a growth factor, a hormone, a cytokine, a toxin, a prodrug, an antimetabolite, a microtubule inhibitor, a radioactive material, a targeting moiety, an aryl group, a linear or branched alkenyl group, a linear or branched alkyl group, wherein said alkyl, alkenyl or aryl group is substituted with a perfluorocarbon, perfluorocarbon-$R_4$, perfluorocarbon-$OR_4$;

$R_4$ is independently an alkyl group, an alkylene group, a carboxylate group, a carboxylic acid group, and amino group, an ammonium group, an alkoxyl group, a hydroxyl group or another nitrogen, oxygen or sulfur-containing group;

T, independently is:

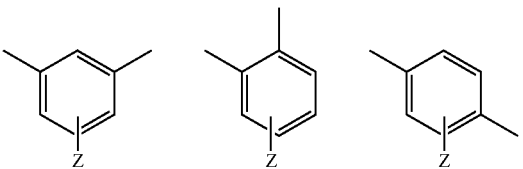

z is, independently, H, alkyl, aryl, $NH_2$, NH-alkyl, NH-acyl, NH-aryl, OH, O-acyl, O-alkyl, O-aryl, a halogen, a nitro group, a hydroxy group, a substituted alkyl group, a substituted aryl group, wherein said substituted alkyl or aryl group is substituted with a perfluorocarbon, perfluorocarbon-$R_4$, perfluorocarbon-$OR_4$, or

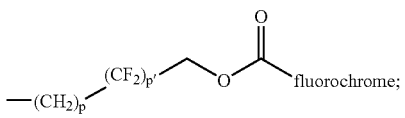

A is, independently O, S, NH;

p, p' are integers;

each y, independently, is an integer from 1-1000; and n is an integer from 1-10,000.

In one embodiment, the polymers with a structure characterized by formula I or II of this invention will be such that the weight of a fraction of the polymer ranges between 0-5% or, in another embodiment, 6-99% of the weight of said polymer, or, in another embodiment, 5-10% of the weight of said polymer, or in another embodiments, x represents about 10-25% of the weight of said polymer, or in another embodiment, x represents from about 30-75% of the weight of said polymer, or in another embodiment, x represents from about 50-100% of the weight of said polymer, wherein the fraction is represented by the structure:

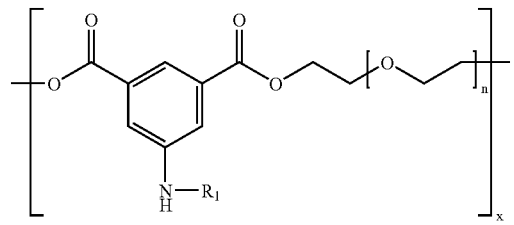

In one embodiment, the polymers with a structure characterized by formula I or II of this invention will be such that the weight of a fraction of the polymer ranges between 1-94% or, in another embodiment, 0% of the weight of said polymer, or, in another embodiment, 5-10% of the weight of said polymer, or in another embodiments, x represents about 10-25% of the weight of said polymer, or in another embodiment, x represents from about 30-75% of the weight of said polymer, or in another embodiment, x represents from about 50-90% of the weight of said polymer, wherein the fraction is represented by the structure:

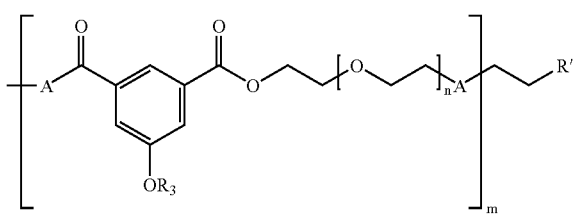

The polymers of this invention are amphiphilic. In one embodiment, the term "amphiphilic" refers to a molecule that contains both hydrophilic and lipophilic (or, synonymously, hydrophobic) moieties.

In one embodiment, the term "alkyl" refers to $C_{1-32}$ straight-chain or $C_{1-32}$ branched hydrocarbons, e.g. methyl, isolbutyl, hexyl, etc. In another embodiment, the term "alkyl" (or "lower alkyl") refers to both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), $-CF_3$, $-CN$ and the like.

In one embodiment, the term "alkoxy" refers to an alkyl group connected to a main chain or backbone through an oxygen atom. In another embodiment, the term "alkoxyl" or "alkoxy" are interchangeable, and representative alkoxyl groups include methoxy, ethoxy, propyloxy, tert-butoxy and the like.

In one embodiment, the term "aryl" refers to aromatic rings such as phenyl, pyridinyl, thienyl, thiazolyl, or furyl, optionally substituted with one or more groups, such as a halo group, a haloalkyl group, an amino group, or an alkyl group. In one embodiment, the term "aryl" includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $-CF_3$, $-CN$, or the like. The term "aryl" also includes polycyclic ring systems having two or more rings in which two or more carbons are common to two adjoining rings (the rings are "fused") wherein at least one of the rings is aromatic, e.g., the other rings can be cycloalkyls, cycloalkenyls, cycloalkynyls, aryls and/or heterocyclyls. In one embodiment, the term "aryloxy" refers to aryl groups attached to a main chain or backbone through an oxygen atom.

In one embodiment, the term "amine" refers to any amine, including primary, secondary, tertiary, quaternary, or a combination thereof, as applicable herein.

In one embodiment, the term "acid activating group" refers to a group which facilitates conjugation of the polymers with a desired substance, via a suitable reactive derivative of a carboxylic acid, which may comprise inter-alia, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as methanol, ethanol, isopropanol, butanol or N-hydroxybenzotriazole; an acyl azide, for example an azide formed by the reaction of the acid and azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

In one embodiment, the term "fluorochrome" refers to a fluorescent substance and may comprise, inter-alia, DAPI, FITC, Cy3, Cy3.5, Cy5, Cy5.5, Cy7, GFP, and others as will be appreciated by one skilled in the art, each selected for specific properties, for example, as described by Waggoner, A. (Methods in Enzymology 246:362-373 (1995) herein incorporated by reference).

In one embodiment, the term "antibody or antibody fragment" refers to intact antibody molecules as well as functional fragments thereof, such as Fab, F(ab')2, and Fv that are capable of binding to an epitope. In one embodiment, an Fab fragment refers to the fragment which contains a monovalent antigen-binding fragment of an antibody molecule, which can be produced by digestion of whole antibody with the enzyme papain to yield an intact light chain and a portion of one heavy chain. In one embodiment, Fab' fragment refers to a part of an antibody molecule that can be obtained by treating whole antibody with pepsin, followed by reduction, to yield an intact light chain and a portion of the heavy chain. Two Fab' fragments may be obtained per antibody molecule. In one embodiment, $(Fab')_2$ refers to a fragment of an antibody that can be obtained by treating whole antibody with the enzyme pepsin without subsequent reduction. In another embodiment, $F(ab')_2$ is a dimer of two Fab' fragments held together by two disulfide bonds. In one embodiment, Fv, may refer to a genetically engineered fragment containing the variable region of the light chain and the variable region of the heavy chain expressed as two chains. In one embodiment, the antibody fragment may be a single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference).

In one embodiment, the antibody will recognize an epitope, which in another embodiment, refers to antigenic determinant on an antigen to which the paratope of an antibody binds. Epitopic determinants may, in other embodiments, consist of chemically active surface groupings of molecules such as amino acids or carbohydrate side chains and in other embodiments, may have specific three dimensional structural characteristics, and/or in other embodiments, have specific charge characteristics.

Antibody fragments according to the present invention can be prepared by proteolytic hydrolysis of the antibody or by expression in E. Coli or mammalian cells (e.g. Chinese hamster ovary cell culture or other protein expression systems) of DNA encoding the fragment.

In other embodiments, antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

In one embodiment, the term "peptide" refers to native peptides (either degradation products, synthetically synthesized peptides or recombinant peptides) and/or peptidomimetics (typically, synthetically synthesized peptides), such as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), *-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom.

These modifications can occur at any of the bonds along the peptide chain and even at several (2-3) at the same time. Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

In one embodiment, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" may include both D- and L-amino acids.

Peptides or proteins of this invention may be prepared by various techniques known in the art, including phage display libraries [Hoogenboom and Winter, J. Mol. Biol. 227:381 (1991); Marks et al., J. Mol. Biol. 222:581 (1991)].

In one embodiment, the term "oligonucleotide" is interchangeable with the term "nucleic acid", and may -refer to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

Nucleic acid sequences, of which the polymers, micelles and/or compositions of this invention may be comprised, may include their being a part a particular vector, depending, in one embodiment, upon the desired method of introduction of the sequence within cells. In one embodiment, such vectors may be encapsulated within the micelles of this invention. In one embodiment, polynucleotide segments encoding sequences of interest can be ligated into commercially available expression vector systems suitable for transducing/transforming mammalian cells and for directing the expression of recombinant products within the transduced cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides.

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be expressed by a cell is not readily assayable, an expression system can first be optimized using a reporter gene linked to the regulatory elements and vector to be used. The reporter gene encodes a gene product, which is easily detectable and, thus, can be used to evaluate efficacy of the system. Standard reporter genes used in the art include genes encoding β-galactosidase, chloramphenicol acetyl transferase, luciferase and human growth hormone, or any of the marker proteins listed herein.

As will be appreciated by one skilled in the art, a fragment or derivative of a nucleic acid sequence or gene that encodes for a protein or peptide can still function in the same manner as the entire, wild type gene or sequence. Likewise, forms of nucleic acid sequences can have variations as compared to wild type sequences, nevertheless encoding the protein or peptide of interest, or fragments thereof, retaining wild type function exhibiting the same biological effect, despite these variations. Each of these represents a separate embodiment of this present invention.

The nucleic acids can be produced by any synthetic or recombinant process such as is well known in the art. Nucleic acids can further be modified to alter biophysical or biological properties by means of techniques known in the art. For example, the nucleic acid can be modified to increase its stability against nucleases (e.g., "end-capping"), or to modify its lipophilicity, solubility, or binding affinity to complementary sequences.

DNA according to the invention can also be chemically synthesized by methods known in the art. For example, the DNA can be synthesized chemically from the four nucleotides in whole or in part by methods known in the art. Such methods include those described in Caruthers (1985). DNA can also be synthesized by preparing overlapping double-stranded oligonucleotides, filling in the gaps, and ligating the ends together (see, generally, Sambrook et al. (1989) and Glover et al. (1995)). DNA expressing functional homologues of the protein can be prepared from wild-type DNA by site-directed mutagenesis (see, for example, Zoller et al. (1982); Zoller (1983); and Zoller (1984); McPherson (1991)). The DNA obtained can be amplified by methods known in the art. One suitable method is the polymerase chain reaction (PCR) method described in Saiki et al. (1988), Mullis et al., U.S. Pat. No. 4,683,195, and Sambrook et al. (1989).

Methods for modifying nucleic acids to achieve specific purposes are disclosed in the art, for example, in Sambrook et al. (1989). Moreover, the nucleic acid sequences of the invention can include one or more portions of nucleotide sequence that are non-coding for the protein of interest. Variations in the DNA sequences, which are caused by point mutations or by induced modifications (including insertion, deletion, and substitution) to enhance the activity, half-life or production of the polypeptides encoded thereby, are also encompassed in the invention.

In another embodiment, the agent that inhibits gene expression, activity or function comprises a nucleic acid. The nucleic acid may, in one embodiment, be DNA, or in another embodiment, the nucleic acid is RNA. In other embodiments, the nucleic acid may be single or double stranded.

In another embodiment, the agent is a nucleic acid that is antisense in orientation to a sequence encoding for a caspase.

In one embodiment, the polymers, micelles or compositions of this invention may be used for gene silencing applications. In one embodiment, the activity or function of a particular gene is suppressed or diminished, via the use of antisense oligonucleotides, which are chimeric molecules, containing two or more chemically distinct regions, each made up of at least one nucleotide. In one embodiment, the antisense molecules may be conjugated to the polymers of this invention, as described, or in another embodiment, encapsulated within micelles of this invention, much as any of the respective groups listed herein, applicable in the methods of this invention, in another embodiment, may be conjugated to the polymers of this invention, or encapsulated within micelles of this invention.

Antisense oligonucleotides, in one embodiment, may be chimeric oligonucleotides, which contain at least one region wherein the oligonucleotide is modified so as to confer upon the oligonucleotide an increased resistance to nuclease degradation, increased cellular uptake, and/or increased binding affinity for the target polynucleotide. An additional region of the oligonucleotide may serve as a substrate for enzymes capable of cleaving RNA:DNA or RNA:RNA hybrids, which according to this aspect of the invention, serves as a means of gene silencing via degradation of specific sequences. Cleavage of the RNA target can be routinely detected by gel electrophoresis and, if necessary, associated nucleic acid hybridization techniques known in the art.

The chimeric antisense oligonucleotides may, in one embodiment, be formed as composite structures of two or more oligonucleotides and/or modified oligonucleotides, as is well described in the art (see, for example, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922), and can, in another embodiment, comprise a ribozyme sequence.

Inhibition of gene expression, activity or function is effected, in another embodiment, via the use of small interfering RNAs, which provides sequence-specific inhibition of gene expression. Administration of double stranded/duplex RNA (dsRNA) corresponding to a single gene in an organism can silence expression of the specific gene by rapid degradation of the mRNA in affected cells. This process is referred to as gene silencing, with the dsRNA functioning as a specific RNA inhibitor (RNAi). RNAi may be derived from natural sources, such as in endogenous virus and transposon activity, or it can be artificially introduced into cells (Elbashir S M, et al (2001). Nature 411:494-498) via microinjection (Fire et al. (1998) Nature 391: 806-11), or by transformation with gene constructs generating complementary RNAs or fold-back RNA, or by other vectors (Waterhouse, P. M., et al. (1998). Proc. Natl. Acad. Sci. USA 95, 13959-13964 and Wang, Z., et al. (2000). J. Biol. Chem. 275, 40174-40179). The RNAi mediating mRNA degradation, in one embodiment, comprises duplex or double-stranded RNA, or, in other embodiments, include single-stranded RNA, isolated RNA (partially purified RNA, essentially pure RNA, synthetic RNA, recombinantly produced RNA), as well as altered RNA that differs from naturally occurring RNA by the addition, deletion and/or alteration of one or more nucleotides.

When referring to nucleic acid sequences utilized as modulators in this invention, it is to be understood that such reference allows for the incorporation of non-nucleotide material, which may be added, for example, to the end(s) of the nucleotide sequence, including for example, terminal 3' hydroxyl groups, or internal additions, at one or more nucleotides. Nucleic acids may, in another embodiment, incorporate non-standard nucleotides, including non-naturally-occurring nucleotides. Alterations may also include the construction of blunt and/or overhanging ends. Collectively all such altered nucleic acids may be referred to as analogs, and represent contemplated embodiments of the invention.

In another embodiment, gene expression can be inhibited/downregulated simply by "knocking out" the gene. Typically this is accomplished by disrupting the gene, the promoter regulating the gene or sequences between the promoter and the gene. Such disruption can be specifically directed to a particular gene by homologous recombination where a "knockout construct" contains flanking sequences complementary to the domain to which the construct is targeted. Insertion of the knockout construct (e.g. into the gene of interest) results in disruption of that gene. The phrases "disruption of the gene" and "gene disruption" refer to insertion of a nucleic acid sequence into one region of the native DNA sequence (in some embodiments, in one or more exons) and/or the promoter region of a gene so as to decrease or prevent expression of that gene in the cell as compared to the wild-type or naturally occurring sequence of the gene.

Knockout constructs can be produced by standard methods known to those of skill in the art. The knockout construct can be chemically synthesized or assembled, e.g., using recombinant DNA methods. The DNA sequence to be used in producing the knockout construct is digested with a particular restriction enzyme selected to cut at a location(s) such that a new DNA sequence encoding a marker gene can be inserted in the proper position within this DNA sequence. The proper position for marker gene insertion is that which will serve to prevent expression of the native gene; this position will depend on various factors such as the restriction sites in the sequence to be cut, and whether an exon sequence or a promoter sequence, or both is (are) to be interrupted (i.e., the precise location of insertion necessary to inhibit promoter function or to inhibit synthesis of the native exon).

It is to be understood that the above nucleic acids may be delivered to any tissue or cells in one embodiment, in their native form, or, in another embodiment within an expression vector that is competent to transfect cells in vitro and/or in vivo, and comprise an embodiment of this invention.

In another embodiment, this invention provides a method of nucleic acid delivery, comprising contacting a cell with a polymer, micelle or composition of this invention, comprising a nucleic acid of interest. In one embodiment, the nucleic acid encodes for a compound, which stimulates organogenesis, for example, the compound is osteogenic, chondrogenic or angiogenic. In another embodiment, the nucleic acid encodes for an antibacterial, antiviral, antifungal or antiparasitic peptide or protein. In another embodiment, the nucleic acid encodes for a peptide or protein with cytotoxic or anticancer activity. In another embodiment, the nucleic acid encodes for an enzyme, a receptor, a channel protein, a hormone, a cytokine or a growth factor. In another embodiment, the nucleic acid encodes for a peptide or protein, which is immunostimulatory. In another embodiment, the nucleic acid encodes for a peptide or protein, which inhibits inflammatory or immune responses. In another embodiment, release of the nucleic acid occurs over a period of time.

In one embodiment, the polymers, micelles or compositions of this invention are targeted to cells. In one embodiment, the cell may be any responsive cell, such as, in one embodiment, an epithelial cell, a lung cell, a kidney cell, a liver cell, a cardiocyte, an astrocyte, a glial cell, a prostate cell, a professional antigen presenting cell, a lymphocyte, an M cell, a pancreatic cell, a stem cell, a myoblast, a hepatocyte, an osteoblast, an osteocyte, an osteoclast, a chondrocyte, a chodroblast, or other bone or cartilage cells and may be used for applications as described in, for example, Wilson, J. M et al. (1988) Proc. Natl. Acad. Sci. USA 85:3014-3018; Armentano, D. et al. (1990) Proc. Natl. Acad. Sci. USA 87:6141-6145; Wolff, J. A. et al. (1990) Science 247:1465-1468; Chowdhury, J. R. et al. (1991) Science 254:1802-1805; Ferry, N. et al. (1991) Proc. Natl. Acad. Sci. USA 88:8377-8381; Wilson, J. M. et al. (1992) J. Biol. Chem. 267:963-967; Quantin, B. et al. (1992) Proc. Natl. Acad. Sci. USA 89:2581-2584; Dai, Y. et al. (1992) Proc. Natl. Acad. Sci. USA 89:10892-10895; van Beusechem, V. W. et al. (1992) Proc. Natl. Acad Sci. USA 89:7640-7644; Rosenfeld, M. A. et al. (1992) Cell 68:143-155; Kay, M. A. et al. (1992) Human Gene Therapy 3:641-647; Cristiano, R. J. et al. (1993) Proc. Natl. Acad Sci. USA 90:2122-2126; Hwu, P. et al. (1993) J. Immunol. 150: 4104-4115; and Herz, J. and Gerard, R. D. (1993) Proc. Natl. Acad Sci. USA 90:2812-2816.

In one embodiment, the polymers, micelles or compositions of this invention comprise a drug. In one embodiment, the term "drug" refers to a substance applicable for use in the diagnosis, or in another embodiment, cure, or in another embodiment, mitigation, or in another embodiment, treatment, or or in another embodiment, prevention of a disease, disorder, condition or infection. In one embodiment, the term "drug" refers to any substance which affect the structure or function of the the target to which it is applied.

In another embodiment, the term "drug" refers to a molecule that alleviates a symptom of a disease or disorder when administered to a subject afflicted thereof. In one embodiment, a drug is a synthetic molecule, or in another embodiment, a drug is a naturally occurring compound isolated from a source found in nature.

In one embodiment, drugs may comprise antihypertensives, antidepressants, antianxiety agents, anticlotting agents, anticonvulsants, blood glucose-lowering agents, decongestants, antihistamines, antitussives, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism in agents, antibiotics, antiviral agents, anti-neoplastics, barbituates, sedatives, nutritional agents, beta blockers, emetics, anti-emetics, diuretics, anticoagulants, cardiotonics, androgens, corticoids, anabolic agents, growth hormone secretagogues, anti-infective agents, coronary vasodilators, carbonic anhydrase inhibitors, antiprotozoals, gastrointestinal agents, serotonin antagonists, anesthetics, hypoglycemic agents, dopaminergic agents, anti-Alzheimer's Disease agents, anti-ulcer agents, platelet inhibitors and glycogen phosphorylase inhibitors.

In one embodiment, examples of the drugs conjugated to the polymers of this invention, or in another embodiment, encapsulated within a micelle of this invention, comprise, inter-alia, antihypertensives including prazosin, nifedipine, trimazosin, amlodipine, and doxazosin mesylate; the antianxiety agent hydroxyzine; a blood glucose lowering agent such as glipizide; an anti-impotence agent such as sildenafil citrate; anti-neoplastics such as chlorambucil, lomustine or echinomycin; anti-inflammatory agents such as betamethasone, prednisolone, piroxicam, aspirin, flurbiprofen and (+)-N-(4-[3-(4-fluorophenoxy)phenoxy]-2-cyclopenten-1-yl}-N-hyroxyurea; antivirals such as acyclovir, nelfinavir, or virazole; vitamins/nutritional agents such as retinol and vitamin E; emetics such as apomorphine; diuretics such as chlorthalidone and spironolactone; an anticoagulant such as dicumarol; cardiotonics such as digoxin and digitoxin; androgens such as 17-methyltestosterone and testosterone; a mineral corticoid such as desoxycorticosterone; a steroidal hypnotic/anesthetic such as alfaxalone; an anabolic agent such as fluoxymesterone or methanstenolone; antidepression agents such as fluoxetine, pyroxidine, venlafaxine, sertraline, paroxetine, sulpiride,[3,6-dimethyl-2-(2,4,6-trimethyl-phenoxy)-pyridin-4-yl]-(lethylpropyl)-amine or 3,5-dimethyl-4-(3'-pentoxy)-2-(2',4',6'-trimethylphenoxy)pyridine; an antibiotic such as ampicillin and penicillin G; an anti-infective such as benzalkonium chloride or chlorhexidine; a coronary vasodilator such as nitroglycerin or mioflazine; a hypnotic such as etomidate; a carbonic anhydrase inhibitor such as acetazolamide or chlorzolamide; an antifungal such as econazole, terconazole, fluconazole, voriconazole or griseofulvin; an antiprotozoal such as metronidazole; an imidazole-type antineoplastic such as tubulazole; an anthelmintic agent such as thiabendazole or oxfendazole; an antihistamine such as astemizole, levocabastine, cetirizine, or cinnarizine; a decongestant such as pseudoephedrine; antipsychotics such as fluspirilene, penfluridole, risperidone or ziprasidone; a gastrointestinal agent such as loperamide or cisapride; a serotonin antagonist such as ketanserin or mianserin; an anesthetic such as lidocaine; a hypoglycemic agent such as acetohexamide; an anti-emetic such as dimenhydrinate; an antibacterial such as cotrimoxazole; a dopaminergic agent such as L-DOPA; anti-Alzheimer agents such as THA or donepezil; an anti-ulcer agent/H2 antagonist such as famotidine; a sedative/hypnotic such as chlordiazepoxide or triazolam; a vasodilator such as alprostadil; a platelet inhibitor such as prostacyclin; an ACE inhibitor/antihypertensive such as enalaprilic acid or lisinopril; a tetracycline antibiotic such as oxytetracycline or minocycline; a macrolide antibiotic such as azithromycin, clarithromycin, erythromycin or spiramycin; and glycogen phosphorylase inhibitors such as [R-(R*S*)]-5-chloro-N-[2-hydroxy-3{methoxymethylamino}-3-oxo-1-(phenylmethyl)-propyl]-IH-indole-2-carboxamide or 5-chloro-1-Hindole-2-carboxylic acid [(IS)-benzyl(2R)-hydroxy-3-((3R,4S)dihydroxy-pyrrolidin-1-yl-)-oxypropyl] amide.

Further examples of drugs deliverable by the invention are the glucose-lowering drug chlorpropamide, the anti-fungal fluconazole, the anti-hypercholesterolemic atorvastatin calcium, the antipsychotic thiothixene hydrochloride, the anxiolytics hydroxyzine hydrochloride or doxepin hydrochloride, the anti-hypertensive amlodipine besylate, the antiinflammatories piroxicam and celicoxib and valdicoxib, and the antibiotics carbenicillin indanyl sodium, bacampicillin hydrochloride, troleandomycin, and doxycycline hyclate.

In another embodiment a drug of this invention may comprise other antineoplastic agents such as platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, paclitaxel and other taxenes, rapamycin, manumycin A, TNP-470, plicamycin (mithramycin), aminoglutethimide,estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, interferon .alpha.-2a, interferon .alpha.-2b, teniposide (VM-26), vinblastine sulfate (VLB), vincristine sulfate, bleomycin sulfate, hydroxyurea ,procarbazine, and dacarbazine; mitotic inhibitors such as etoposide, colchicine, and the vinca alkaloids, radiopharmaceuticals such as radioactive iodine and phosphorus products; hormones such as progestins, estrogens and antiestrogens; anti-helmintics, antimalarials, and antituberculosis drugs; biologicals such as immune serums, antitoxins and antivenoms; rabies prophylaxis products; bacterial vaccines; viral vaccines; respiratory products such as xanthine derivatives theophylline and aminophylline; thyroid agents such as iodine products and anti-thyroid agents; cardiovascular products including chelating agents and mercurial diuretics and cardiac glycosides; glucagon; blood products such as parenteral iron, hemin, hematoporphyrins and their derivatives; biological response modifiers such as muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-L-alanyl-D-isoglutamine; anti-fungal agents such as ketoconazole, nystatin, griseofulvin, flucytosine (5-fc), miconazole, amphotericin B, ricin, cyclosporins, and β-lactam antibiotics (e.g., sulfazecin); hormones such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, oxytocin, vassopressin, and their derivatives; vitamins such as cyanocobalamin neinoic acid, retinoids and derivatives such as retinol palmitate, and .alpha.-tocopherol; peptides, such as manganese super oxide dismutase; enzymes such as alkaline phosphatase; anti-allergic agents such as amelexanox; anti-coagulation agents such as phenprocoumon and heparin; circulatory drugs such as propranolol; metabolic potentiators such as glutathione; antituberculars such as para-aminosalicylic acid, isoniazid, capreomycin sulfate cycloserine, ethambutol hydrochloride ethionamide, pyrazinamide, rifampin, and streptomycin sulfate; antivirals such as amantadine azidothymidine (AZT, DDI, Foscarnet, or Zidovudine), ribavirin and vidarabine monohydrate (adenine arabinoside, ara-A); antianginals such as diltiazem, nifedipine, verapamil, erythritol tetranitrate, isosorbide dinitrate, nitroglycerin (glyceryl trinitrate) and pentaerythritol tetranitrate; anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin including penicillin G and penicillin V, ticarcillin rifampin and tetracycline; antiinflammatories such as diflunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine,hydroxychloroquine, metronidazole, quinine and meglumine antimonate; antirheumatics such as penicillamine; narcotics such as paregoric;opiates such as codeine, heroin, methadone, morphine and opium; cardiac glycosides such as deslanoside, digitoxin, digoxin, digitalin and digitalis; neuromuscular blockers such as atracurium mesylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; general anesthetics such as droperidol, etomidate, fentanyl citrate with droperidol, ketamine hydrochloride, methohexital sodium and thiopental sodium; and radioactive particles or ions such as strontium, iodide rhenium and yttrium.

In one embodiment, the term "drug" refers to a therapeutic compound. In one embodiment, the therapeutic compound is a peptide, a protein or a nucleic acid. In another embodiment, the therapeutic compound is organogenic, such as osteogenic, chondrogenic or angiogenic. In another embodiment, the therapeutic compound is an antibacterial, antiviral, antifungal or antiparasitic compound. In another embodiment, the therapeutic compound has cytotoxic or anti-cancer activity. In another embodiment, the therapeutic compound is an enzyme, a receptor, a channel protein, a hormone, a cytokine or a growth factor. In another embodiment, the therapeutic compound is immunostimulatory. In another embodiment, the therapeutic compound inhibits inflammatory or immune responses.

In one embodiment, the term "therapeutic", refers to a molecule, which when provided to a subject in need, provides a beneficial effect. In some cases, the molecule is therapeutic in that it functions to replace an absence or diminished presence of such a molecule in a subject. In one embodiment, the molecule is a nucleic acid coding for the expression of a protein is absent, such as in cases of an endogenous null mutant being compensated for by expression of the foreign protein. In other embodiments, the endogenous protein is mutated, and produces a non-functional protein, compensated for by the expression of a heterologous functional protein. In other embodiments, expression of a heterologous protein is additive to low endogenous levels, resulting in cumulative enhanced expression of a given protein. In other embodiments, the molecule stimulates a signalling cascade that provides for expression, or secretion, or others of a critical element for cellular or host functioning. In one embodiment, the therapeutic compound is a protein or polypeptide.

In one embodiment, the therapeutic protein may include cytokines, such as interferons or interleukins, or their receptors. Lack of expression of cytokines, or of the appropriate ones, has been implicated in susceptibility to diseases, and enhanced expression may lead to resistance to a number of infections. Expression patterns of cytokines may be altered to produce a beneficial effect, such as for example, a biasing of the immune response toward a Th1 type expression pattern, or a Th2 pattern in infection, or in autoimmune disease, wherein altered expression patterns may prove beneficial to the host.

In another embodiment, the therapeutic protein may comprise an enzyme, such as one involved in glycogen storage or breakdown. In another embodiment, the therapeutic protein comprises a transporter, such as an ion transporter, for example CFTR, or a glucose transporter, or other transporters whose deficiency, or inappropriate expression, results in a variety of diseases.

In another embodiment, the therapeutic protein comprises a tumor suppressor, or proapoptotic compound, which alters progression of cancer-related events.

In another embodiment, the therapeutic compound of the present invention may comprise an immunomodulating protein. In one embodiment, the immunomodulating protein comprises cytokines, chemokines, complement or components, such as interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1a and MIP-1b, or complement components.

In another embodiment, a therapeutic compound of this invention may comprise a growth factor, or tissue-promoting factor. In one embodiment, the therapeutic compound is a bone morphogenetic protein, or OP-1, OP-2, BMP-5, BMP-6, BMP-2, BMP-3, BMP-4, BMP-9, DPP, Vg-1, 60A, or Vgr-1. In another embodiment, the therapeutic compound facilitates nerve regeneration or repair, and may include NGF, or other growth factors.

In one embodiment, drug may also refer to a nucleic acid, or construct comprising a nucleic acid, whose expression ameliorates or abrogates symptoms of a disease or a disorder, or diminishes, suppresses or inhibits a disease, disorder or condition. In one embodiment, the nucleic acid or construct comprising the same, is used for gene therapy, for providing or replacing endogenous expression, or in another embodiment, suppressing endogenous expression.

In another embodiment, the therapeutic molecule may be natural or non-natural insulins, amylases, proteases, lipases, kinases, phosphatases, glycosyl transferases, trypsinogen, chymotrypsinogen, carboxypeptidases, hormones, ribonucleases, deoxyribonucleases, triacylglycerol lipase, phospholipase A2, elastases, amylases, blood clotting factors, UDP glucuronyl transferases, ornithine transcarbamoylases, cytochrome p450 enzymes, adenosine deaminases, serum thymic factors, thymic humoral factors, thymopoietins, growth hormones, somatomedins, costimulatory factors, antibodies, colony stimulating factors, erythropoietin, epidermal growth factors, hepatic erythropoietic factors (hepatopoietin), liver-cell growth factors, interleukins, interferons, negative growth factors, fibroblast growth factors, transforming growth factors of the a family, transforming growth factors of the β family, gastrins, secretins, cholecystokinins, somatostatins, serotonins, substance P, transcription factors or combinations thereof.

In one embodiment, the polymers, micelles or compositions of this invention may further comprise a ligand for a biological target, which in another embodiment, provides for directional specificity as to which cells or tissues are provided the the polymers, micelles or compositions of this invention. In one embodiment, the term "ligand for a biological target" refers to a molecule which enables the specific delivery of the polymer, micelle or composition of this invention to a particular site in vivo. In one embodiment, such a ligand may be referred to as an "anti-receptor", which functions to direct the polymer or micelle to, for example, virally infected cells, via anti-receptor binding to viral proteins expressed on infected cell surfaces. In this case, antireceptors to promote fusion with virally-infected cells, will recognize and bind to virally expressed surface proteins. For example, HIV-1 infected cells may express HIV-associated proteins, such as gp120, and therefore the presence of CD4 on the polymer or micelle surface promotes targeting to HIV infected cells, via CD4-gp120 interaction.

The anti-receptor proteins or polypeptide fragments thereof may be designed to enhance fusion with cells infected with members of the following viral families: Arenaviridae, Bunyaviridae, Coronaviridae, Filoviridae, Flaviviridae, Herpesviridae, Hepadnaviridae, Orthomyxoviridae, Paramyxoviridae,Poxviridae, Retroviridae, and Rhabdoviridae. Additional viral targeting agents may be derived from the following: African Swine Fever Virus, Borna Disease Virus, Hepatitis X, HIV-1, Human T Lymphocyte virus type-I (HTLV-1), HTLV-2, 1 5 lentiviruses, Epstein-Barr Virus, papilloma viruses, herpes simplex viruses, hepatitis B and hepatitis C.

In another embodiment, targeting virally-infected cells may be accomplished through the additional expression of viral co-receptors on an exposed surface of the polymers/micelles of this invention, for enhanced fusion facilitation with infected cells. In one embodiment, the polymers/micelles of this invention comprise an HIV co-receptor such as $CXCR_4$ or CCR5, for example.

Bacterial proteins expressed during intracellular infection are also potential targets contemplated for therapeutic intervention by polymers/micelles of this invention. The intracellular bacteria may include, amongst others: Shigella, Salmonella, Legionella, Streptococci, Mycobacteria, Francisella and Chlamydiae (See G. L. Mandell, "Introduction to Bacterial Disease" IN CECIL TEXTBOOK OF MEDICINE, (W.B. Saunders Co., 1996) 1556-7). These bacteria would be expected to express a bacteria-related protein on the surface of the infected cell to which the polymers/micelles of this invention would attach.

In another embodiment, the targeting moieties may include integrins or class II molecules of the MHC, which may be upregulated on infected cells such as professional antigen presenting cells.

Proteins of parasitic agents, which reside intracellularly, also are targets contemplated for targeting by the polymers/micelles of this invention. The intracellular parasites contemplated include for example, Protozoa. Protozoa, which infect cells, include: parasites of the genus *Plasmodium* (e.g., *Plasmodium falciparum, P. Vivax, P. ovale and P. malariae*), *Trypanosoma, Toxoplasma, Leishmania*, and *Cryptosporidium.*

Diseased and/or abnormal cells may be targeted using the polymers/micelles of this invention by the methods described above. The diseased or abnormal cells contemplated include: infected cells, neoplastic cells, pre-neoplastic cells, inflammatory foci, benign tumors or polyps, cafe au lait spots, leukoplakia, other skin moles, self-reactive cells, including T and/or NK cells, etc. Any cell, to which specific delivery of an agent to modulate its activity is contemplated for the methods of this invention, and represents an embodiment thereof.

The polymers/micelles of this invention may be targeted using an anti-receptor that will recognize and bind to its cognate receptor or ligand expressed on a diseased or abnormal cell, in another embodiment.

In one embodiment, the targeting agent specifically binds, or preferentially binds only diseased cells, for delivery of a therapeutic agent, or in another embodiment, a cytotoxic agent. In one embodiment, the targeting agent is an antibody, or fragment thereof. Examples of antibodies include those antibodies, which react with malignant prostatic epithelium but not with benign prostate tissue (e.g., ATCC No. HB-9119; ATCC HB-9120; and ATCC No. HB-1 1430) or react with malignant breast cancer cells but not with normal breast tissue (e.g., ATCC No. HB-8691; ATCC No. HB-10807; and 21HB-108011). Other antibodies or fragments thereof, which react with diseased tissue and not with normal tissue, would be apparent to the skilled artisan.

A wide variety of tumor-specific antibodies are known in the art, such as those described in U.S. Pat. Nos. 6,197,524, 6,191,255, 6,183,971, 6,162,606, 6,160,099, 6,143,873, 6,140,470, 6,139,869, 6,113,897, 6,106,833, 6,042,829, 6,042,828, 6,024,955, 6,020,153, 6,015,680, 5,990,297, 5,990,287, 5,972,628, 5,972,628, 5,959,084, 5,951,985, 5,939,532, 5,939,532, 5,939,277, 5,885,830, 5,874,255, 5,843,708, 5,837,845, 5,830,470, 5,792,616, 5,767,246, 5,747,048, 5,705,341, 5,690,935, 5,688,657, 5,688,505, 5,665,854, 5,656,444, 5,650,300, 5,643,740, 5,635,600, 5,589,573, 5,576,182, 5,552,526, 5,532,159, 5,525,337, 5,521,528, 5,519,120, 5,495,002, 5,474,755, 5,459,043, 5,427,917, 5,348,880, 5,344,919, 5,338,832, 5,298,393, 5,331,093, 5,244,801, and 5,169,774. See also The Monoclonal Antibody Index Volume 1: Cancer (3rd edition). Accordingly, the polymers, micelles and/or compositions of this invention may comprise tumor-specific antibodies which may recognize tumors derived from a wide variety of tissue types, including, but not limited to, breast, prostate, colon, lung, pharynx, thyroid, lymphoid, lymphatic, larynx, esophagus, oral mucosa, bladder, stomach, intestine, liver, pancreas, ovary, uterus, cervix, testes, dermis, bone, blood and brain.

In another embodiment, the polymers, micelles or compositions of this invention will incorporate an antibody which possesses tumoricidal activity. Antibodies that possess tumoricidal activity are also known in the art, including IMC-C225, EMD 72000, OvaRex Mab B43.13, anti-ganglioside G(D2) antibody ch14.18, C017-1A, trastuzumab, rhuMAb VEGF, sc-321, AF349, BAF349, AF743, BAF743, MAB743, AB1875, Anti-Flt-4AB3127, FLT41-A, rituximab, 2C3, CAMPATH 1H, 2G7, Alpha IR-3, ABX-EGF, MDX-447, anti-p75 IL-2R, anti-p64 IL-2R, and 2A11.

Epitopes to which tumor-specific antibodies bind are also well known in the art. For example, epitopes bound by the tumor-specific antibodies of the invention include, but are not limited to, those known in the art to be present on CA-125, gangliosides G(D2), G(M2) and G(D3), CD20, CD52, CD33, Ep-CAM, CEA, bombesin-like peptides, PSA, HER2/neu, epidermal growth factor receptor, erbB2, erbB3, erbB4, CD44v6, Ki-67, cancer-associated mucin, VEGF, VEGFRs (e.g., VEGFR3), estrogen receptors, Lewis-Y antigen, TGF$\beta$1, IGF-1 receptor, EGF$\alpha$, c-Kit receptor, transferrin receptor, IL-2R and CO17-1A. It is to be understood that antibodies to these, and other epitopes, may be designed by methods well known in the art, such as, for example, as described in Harlow and Lane (1988) Antibodies: A Laboratory Manual, Cold Spring Harbor Laboratory, New York (Harlow and Lane, 1988), or "Current Protocols in Immunology" (Coligan, 1991), and may be incorporated in the polymers, micelles and/or compositions of this invention, and represents embodiments thereof.

In one embodiment, the targeting moiety is a peptide, an antibody, an antibody fragment, a receptor, Protein A, Protein G, biotin, avidin, streptavidin, a metal ion chelate, an enzyme cofactor, a nucleic acid or a ligand.

In another embodiment, the targeting moiety is a peptide which binds to an underglycosylated mucin-1 protein. In one embodiment, the peptide is an EPPT1 peptide.

Mucin-1 (MUC-1) is a transmembrane molecule, which is overexpressed on the cell surface and in intracellular compartments of almost all human epithelial cell adenocarcinomas, including more than 90% of human breast cancers, ovarian, pancreatic, colorectal, lung, prostate, colon and gastric carcinomas. Expression has been demonstrated in non-epithelial cancer cell lines (for example, astrocytoma, melanoma, and neuroblastoma), as well as in hematological malignancies such as multiple myeloma and some B-cell non-Hodgkin lymphomas, constituting more than 50% of all cancers in humans.

In one embodiment, the synthetic peptide EPPT1, also known as alpha-M2 peptide (YCAREPPTRTFAYWG-SEQ ID NO: 1), derived from the CDR3 Vh region of a monoclonal antibody (ASM2) raised against human epithelial cancer cells, is used in the polymers/micelles and/or methods of this invention.

In one embodiment, the targeting moiety enhances attachment to a molecule, or, in another embodiment, a cell in low abundance, which is of interest. In another embodiment, the targeting moiety enhances attachment following supply of an energy source. In one embodiment, the targeting moiety is chemically attached to the polymers via a chemical cross-linking group, or in another embodiment, forms a stable association with the polymer, or, in another embodiment, forms an association with the polymer, which readily dissociates following changes in solution conditions, such as, for example, salt concentration or pH.

In one embodiment, the targeting moiety may be an antibody, which specifically recognizes a molecule of interest, such as a protein or nucleic acid. In another embodiment, the antibody may specifically recognize a reporter molecule attached to a molecule of interest. In another embodiment, the targeting moiety may be an antibody fragment, Protein A, Protein G, biotin, avidin, streptavidin, a metal ion chelate, an enzyme cofactor, or a nucleic acid. In another embodiment, the targeting moiety may be a receptor, which binds to a cognate ligand of interest, or associated with a cell or molecule of interest, or in another embodiment, the targeting moiety may be a ligand which is used to attach to a cell via interaction with its cognate receptor.

In one embodiment, the term "immunoconjugate" refers to an antibody bound to a compound. In one embodiment, the conjugation of an antibody as described, with a polymer or encapsulated within a micelle of this invention represents the immunoconjugates comprising the invention. In another embodiment, the compound to which the antibody is bound, is conjugated to a polymer or encapsulated within a micelle of this invention, and is to be considered as part of this invention, or in another embodiment, the antibody, to which a compound is bound, is further conjugated to a polymer, or encapsulated within a micelle of this invention.

In one embodiment, the term "a labeling agent" refers to a molecule which renders readily detectable that which is contacted with a labeling agent. IN one embodiment, the labeling agent is a marker polypeptide. The marker polypeptide may comprise, for example, green fluorescent protein (GFP), DS-Red (red fluorescent protein), secreted alkaline phosphatase (SEAP), beta-galactosidase, luciferase, or any number of other reporter proteins known to one skilled in the art. In another embodiment, the labeling agent may be conjugated to another molecule which provides greater specificity for the target to be labeled. For example, and in one embodiment, the labeling agent is a fluorochrome conjugated to an antibody which specifically binds to a given target molecule, or in another embodiment, which specifically binds another antibody bound to a target molecule, such as will be readily appreciated by one skilled in the art.

In one embodiment, the polymer may be conjugated to a quantum dot. In one embodiment, the term "quantum dot" refers to a semiconductor nanocrystal with size-dependent optical and electronic properties. In particular, the band gap energy of a semiconductor nanocrystal varies with the diameter of the crystal. "Semiconductor nanocrystal" includes, for example, inorganic crystallites between about 1 nm and about 1000 nm in diameter, or in one embodiment, between about 2 nm and about 50 nm, or in another embodiment, between about 5 nm to about 20 nm (such as about 5. 6, 7, 8, 9, 10, 11, 12, 13, 14, 15, 16, 17, 18, 19, or 20 nm) that includes a "core" of one or more first semiconductor materials, and which can be surrounded by a "shell" of a second semiconductor material. A semiconductor nanocrystal core surrounded by a semiconductor shell is referred to as a "core/shell" semiconductor nanocrystal. The surrounding "shell" material may, in another embodiment, have a bandgap greater than the bandgap of the core material and can be chosen so to have an atomic spacing close to that of the "core" substrate. The core and/or the shell can be a semiconductor material including, but not limited to, those of the group II-VI (e.g., ZnS, ZnSe, ZnTe, CdS, CdSe, CdTe, HgS, HgSe, HgTe, MgTe and the like) and III-V (e.g., GaN, GaP, GaAs, GaSb, InN, InP, InAs, InSb, AlAs, AlP, AlSb, AlS, and the like) and IV (e.g., Ge, Si, Pb and the like) materials, and an alloy thereof, or a mixture, including ternary and quaternary mixtures, thereof.

In one embodiment, the term "toxin" refers to a molecule which results in toxic effects in cells and/or tissue exposed to the toxin. In one embodiment, the toxin results in cell death, or in another embodiment, cell damage. In one embodiment, the toxin is a natural product of cells, such as bacterial cells, wherein the toxin is used, in one embodiment, when specifically targeted to disease cells as a means of selective cell killing of diseased cells. In one embodiment, the toxin may comprise any known in the art, such as, for example that produced by cholera, tetanus, or any other appropriate species, as will be appreciated by one skilled in the art.

In another embodiment, this invention also comprises incorporation of any toxic substance for therapeutic purpose. In one embodiment, the polymers/micelles of this invention may incorporate an oligonucleotide encoding a suicide gene, which when in contact with diseased cells or tissue, is expressed within such cells. In one embodiment, the term "suicide gene" refers to a nucleic acid coding for a product, wherein the product causes cell death by itself or in the presence of other compounds. A representative example of a suicide gene is one, which codes for thymidine kinase of herpes simplex virus. Additional examples are thymidine kinase of varicella zoster virus and the bacterial gene cytosine deaminase, which can convert 5-fluorocytosine to the highly cytotoxic compound 5-fluorouracil.

Suicide genes may produce cytotoxicity by converting a prodrug to a product that is cytotoxic. In one embodiment, the term "prodrug" means any compound that can be converted to a toxic product for cells. Representative examples of such a prodrug is gancyclovir which is converted in vivo to a toxic compound by HSV-thymidine kinase. The gancyclovir derivative subsequently is toxic to cells. Other representative examples of prodrugs include acyclovir, FIAU [1-(2-deoxy-2-fluoro-β-D-arabinofuranosyl)-5-iodouracil], 6-methoxypurine arabinoside for VZV-TK, and 5-fluorocytosine for cytosine deaminase.

In another embodiment, the polymers/micelles or compositions of this invention may comprise at least one molecule, which in another embodiment, is a protein, which is immunogenic.

In one embodiment, the term "immunogenic", refers to an ability to elicit an immune response. Immune responses that are cell-mediated, or immune responses that are classically referred to as "humoral", referring to antibody-mediated responses, or both, may be elicited by the polymers/micelles or compositions of this invention of the present invention.

Polymers/micelles or compositions of this invention may, in one embodiment, be used for vaccine purposes, as a means of preventing infection.

In another embodiment, the polymers/micelles or compositions of this invention are utilized, to provide an immunogenic protein or polypeptide eliciting a "Th1" response, in a disease where a so-called "Th2" type response has developed, when the development of a so-called "Th1" type response is beneficial to the subject. Introduction of the immunogenic protein or polypeptide results in a shift toward a Th1 type response.

As used herein, the term "Th2 type response" refers to a pattern of cytokine expression, elicited by T Helper cells as part of the adaptive immune response, which support the development of a robust antibody response. Typically Th2 type responses are beneficial in helminth infections in a subject, for example. Typically Th2 type responses are recognized by the production of interleukin-4 or interleukin 10, for example.

As used herein, the term "Th1 type response" refers to a pattern of cytokine expression, elicited by T Helper cells as part of the adaptive immune response, which support the development of robust cell-mediated immunity. Typically Th1 type responses are beneficial in intracellular infections in a subject, for example. Typically Th1 type responses are recognized by the production of interleukin-2 or interferon y, for example.

In another embodiment, the reverse occurs, where a Th1 type response has developed, when Th2 type responses provide a more beneficial outcome to a subject, where introduction of the immunogenic protein or polypeptide via the polymers/micelles or compositions of this invention provides a shift to the more beneficial cytokine profile. One example would be in leprosy, where the polymers/micelles or compositions of the present invention express an antigen from *M. leprae*, where the antigen stimulates a Th1 cytokine shift, resulting in tuberculoid leprosy, as opposed to lepromatous leprosy, a much more severe form of the disease, associated with Th2 type responses.

It is to be understood that any use of the polymers/micelles or compositions of this invention comprising an immunogenic protein for purposes of immunizing a subject to prevent disease, and/or ameliorate disease, and/or alter disease progression are to be considered as part of this invention.

Examples of infectious virus to which stimulation of a protective immune response is desirable include: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g. influenza viruses); Bungaviridae (e.g., Hantaan viruses, bunga viruses, phleboviruses and Nairo viruses); Arena viridae (hemorrhagic fever viruses); Reoviridae (erg., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) I and 2, varicella zoster virus, cytomegalovirus (CMV), herpes viruses); Poxviridae (variola viruses, vaccinia viruses, pox viruses); and Iridoviridae (e.g. African swine fever virus); and unclassified viruses (e.g., the etiological agents of Spongiform encephalopathies, the agent of delta hepatites (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria to which stimulation of a protective immune response is desirable include: *Helicobacter pylori, Borellia burgdorferi, Legionella pneumophilia, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Chlamidia* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue*, Leptospira, *Actinomyces israeli* and *Francisella tularensis*.

Examples of infectious fungi to which stimulation of a protective immune response is desirable include: *Cryptococcus neoformans, Histoplasma capsulatum, Coccidioides immitis, Blastomyces dermatitidis,Chlamydia trachomatis, Candida albicans*. Other infectious organisms (i.e., protists) include: *Plasmodium* sp., *Leishmania* sp., *Schistosoma* sp. and *Toxoplasma* sp.

In another embodiment, the polymers/micelles or compositions of this invention comprising an immunogenic protein further comprise additional immunomodulating proteins.

Examples of useful immunomodulating proteins include cytokines, chemokines, complement components, immune system accessory and adhesion molecules and their receptors of human or non-human animal specificity. Useful examples include GM-CSF, IL-2, IL-12, OX40, OX40L (gp34), lymphotactin, CD40, and CD40L. Further useful examples include interleukins for example interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1a and MIP-1b, complement components and their receptors, or an accessory molecule such as B7.1, B7.2, TRAP, ICAM-1, 2 or 3 and cytokine receptors. OX40 and OX40-ligand (gp34) are further useful examples of immunomodulatory proteins.

In another embodiment, the immunomodulatory proteins may be of human or non-human animal specificity, and may comprise extracellular domains and/or other fragments with comparable binding activity to the naturally occurring proteins. Immunomodulatory proteins may, in another embodiment, comprise mutated versions of the embodiments listed, or comprise fusion proteins with polypeptide sequences, such as immunoglobulin heavy chain constant domains. Multiple immunomodulatory proteins may be incorporated within a single construct, and as such, represents an additional embodiment of the invention.

It is to be understood that the polymers/micelles or compositions of this invention may comprise multiple immunogenic proteins. In one embodiment, the immunogenic proteins or peptides are derived from the same or related species. Vaccine incorporation of multiple antigens has been shown to provide enhanced immunogenicity.

The polymers/micelles or compositions of this invention comprising an immunogenic protein or peptide fragment may generate immune responses of a variety of types that can be stimulated thus, including responses against the protein or peptide itself, other antigens that are now immunogenic via a "by-stander" effect, against host antigens, and others, and represent additional embodiments of the invention. It is envisioned that methods of the present invention can be used to prevent or treat bacterial, viral, parasitic or other disease states, including tumors, in a subject.

Combination vaccines have been shown to provide enhanced immunogenicity and protection, and, as such, in another embodiment, the immunogenic proteins or peptides are derived from different species.

In one embodiment, the incorporated groups described herein, which are to comprise the micelles, polymers and/or compositions of this invention, may be conjugated to the polymer, or in another embodiment, encapsulated within.

In another embodiment, this invention provides a composition or a micelle comprising a polymer of this invention.

This invention provides amphiphilic polymers, which in one embodiment, are terpolymers. In one embodiment, amphiphilic polymers allow for the formation of spherical nanoparticles, which, in another embodiment, self-assemble into nanospheres. The polymers of this invention, in some embodiments, offer a number of advantages as delivery systems, as compared to other such systems described in the art, as a result of the unique chemical structure of the polymers of this invention.

In one embodiment, the fundamental unit of the polymers of this invention comprises a hydrophilic segment, typically polyethylene glycol (PEG) coupled to a multifunctional, hydrophobic linker molecule. In one embodiment, the PEG ranges in size from 600-4,400 Daltons.

In one embodiment, the multifunctional hydrophobic linker molecule is a trifunctional linker molecule. In one embodiment, the linker is 5-amino dimethylphthalate or 5-hydroxydimethylphthalate. In one embodiment, a hydrophobic side chain is attached to one of the functional groups of the linker via an ether, ester, or amide bond, and the side chain is terminated by a hydrogen or by a functional group such as amino, hydroxyl, or carboxyl. This basic unit is, in another embodiment, further polymerized to yield a base polymer with a molecular size of 150-200,000 Da.

The polymers of this invention may assume any structural configuration, which will be a function of, in some embodiments, the chemical makeup of the polymers, and the environment to which the polymer is exposed. In some embodiments, the polymers of this invention may assume a particle configuration, comprising a core and shell, or in another embodiment, a micelle configuration.

In one embodiment, when the polymer is dissolved in water above the critical micelle concentration, about 8 to 12 polymeric units may self assemble into a spherical micelle consisting of a compact core of side chains covered by linkers with an external corona of deformable PEG loops.

Depending upon chemical composition, the micelles have, in some embodiments, a molecular weight of about 100-200, 000 Da and a diameter (twice the radius of gyration) of about 10 to 300 nm.

In other embodiments, additional agents can be encapsulated in the core by dissolving the polymer and agent in a solvent, evaporating the solvent, and dissolving the resulting viscous mixture in water, with appropriate choice of the side chain terminal group. According to this aspect, and in other embodiments of this invention, a wide variety of compounds, such as, for example, various drugs or therapeutic agents (such as, for example, aspirin, naproxen, celebrex, inulin, insulin, and others, as described herein, and as will be known by one skilled in the art) are encapsulated as cargo within the micelles. In one embodiment, incorporation of these compounds may increase micelle size up to 300 nm in diameter.

The micelle structure may be stabilized, in some embodiments, by the water-soluble PEG at the exterior surface and by hydrophobic interactions between the side chains and linkers. When agents with a hydrophilic character are to be encapsulated within the micelle, in some embodiments, the side chains are chosen to retain sufficient hydrophobic character, as to keep the micelle intact. The stability of the micelles to intracellular conditions, for example, in lysozymes, can be varied by selection of coupling between linker and side chain to obtain more or less resistance to low pH, esterases, and other enzymes, in other embodiments.

In other embodiments, the polymers and/or micelles of this invention may comprise a targeting agent. In one embodiment, the polymers and/or micelles of this invention may contain a therapeutic agent as described, and additionally comprise a targeting agent, such that the targeting agent serves to deliver the therapeutic agent to a desired location, for therapeutic applications. In another embodiment, the targeting agent serves for diagnostic and/or imaging purposes, where an agent is delivered to a particular site, where verification of delivery is desired. In another embodiment, the targeting agent serves to provide a sensitive means of detection of a particular molecule at a particular site, for example, the targeting agent directs a micelle or polymer of this invention to a tissue which expresses a preneoplastic marker, or a cancer associated antigen, wherein the molecule which is being detected is available in low concentration, and in some embodiments, is not detectable by existing methods in the art.

In some embodiments, the targeting agent may be coupled to a free PEG hydroxyl at an end of a base polymer chain.

In some embodiments, through the use of various PEG lengths, linkers, side chains, and side chain terminal groups, great flexibility in polymer/micelle chemical composition, size, structure, and function can be obtained. In some embodiments, such polymers/micelles may be constructed via multiple-step reaction pathways that involve synthesis of a suitable monomer with a protected functional group prior to the polymerization step, followed by deprotection. In other embodiments, the synthesis may be carried out with a chemical/enzymatic/chemo-enzymatic approach as exemplified and described further herein.

In one embodiment, the polymers/micelles of this invention incorporate a perfluorocarbon. In one embodiment, the perfluorocarbon is a linear, cyclic or branched fluoroalkyl, preferably perfluoroalkyl, radical optionally containing one or more oxygen, nitrogen, chlorine, phosphorous, hydrogen and/or sulfur atoms and/or one or more sulfonyl or carbonyl groups, or a sulfonyl or carbonyl-containing fluoropolymeric group.

In one embodiment, the perfluorocarbon may be derived from at least one fluorine-containing polymerizable monomer such as vinyl fluoride, hexafluoropropylene, vinylidene fluoride, trifluoroethylene, trifluorostyrene, chlorotrifluoroethylene, perfluoro(alkylvinyl ether), tetrafluoroethylene, or cyclic monomers such as $-CF=C(OCF_3)O(CF_2)_{20}-$ or $-CF=CFOC(CF_2)_{20}-$ or mixtures thereof.

In another embodiment, sulfonyl fluoride containing monomers are used, and may include, inter-alia, $CF_2=CFOCF_2CF_2SO_2F$, $CF_2=CFOCF_2CFOCF_2CF_2SO_2F$, $CF_2=CFOCF_2CFOCF_2CFOCF_2CF_2SO_2F$, $CF_2=CFCF_2CF_2SO_2F$, or $CF_2=CFOCF_2CFOCF_2CF_2SO_2F$. In other embodiments, fluorocarbon polymer precursors may comprise polymers containing one or more monomers lacking sulfonyl or carbonyl halide functional groups, but which can be modified to include sulfonyl or carbonyl halide groups before or after forming the polymer. Suitable monomers for such use may include trifluorostyrene, trifluorostyrenesulfonic acid or the like.

In one embodiment, fluorocarbon polymer precursors having pendant carbonyl-based functional groups can be prepared in any suitable conventional manner such as in accordance with U.S. Pat. No. 4,151,052 or Japanese patent application No. 52(1977)38486, which are incorporated herein by reference or polymerized from a carbonyl functional group containing a monomer derived from a sulfonyl group containing monomer by a method such as is shown in U.S. Pat. No. 4,151,051 which is incorporated herein by reference. Once prepared, such polymers may then be utilized to form the polymers of this invention, as will be appreciated by one skilled in the art.

A sulfonic acid form of the fluorocarbon polymer precursor can be converted to the sulfonyl or carbonyl halide form of the fluorocarbon polymer precursor by a process, such as described, for example, in U.S. Pat. No. 4,209,367 which is incorporated herein by reference Reaction of the fluorocarbon polymer precursors with amide or sulfonamide-containing reactants or salt thereof can be carried out with the fluorocarbon polymer precursor being in solid form, solvent-swollen form or in solution with the appropriate reactants in the solid, liquid or gas phase. When the fluorocarbon polymer precursor is in the solid form, the reaction is carried out under anhydrous conditions by contacting it with the substituted or unsubstituted amide or sulfonamide-containing reactant or salt thereof in a solvent that is non-reactive with the starting reactants. Representative suitable solvents include anhydrous polar aprotic solvents such as acetonitrile, tetrahydrofuran, dioxane, or the like, halogenated solvents such as chloroform, or the like. The reaction is carried out in the presence of an organic non-nucleophilic base in order to scavenge the halide-containing byproduct of the reaction. Representative suitable non-nucleophilic bases include alkylamines such as triethylamine, trimethylamine, or the like, pyridines, alkyl pyridines, alkyl piperidines, N-alkyl pyrrolidines, or the like, The reaction can be carried out in the absence of a solvent under conditions where there is enough mobility of the reactants to interact with each other such as when the non-nucleophilic base functions as a medium for the reaction. Other suitable halide-containing byproduct scavengers include KF, $Na_2CO_3$, Zn powder, CsF, or the like. Reaction is effected under anhydrous conditions such as under an inert atmosphere such as argon, nitrogen or the like in a vessel or a glove box at a temperature between about 0 and about 200° C., or in another embodiment, between about 25 and about 125° C. Reaction times may be, in other embodiments, between about 5 minutes and about 72 hours, in some embodiments, between about 1 hour and about 24 hours. The reaction can be effected while mixing.

When the fluorocarbon polymer precursor is in solution, it is contacted with the substituted or unsubstituted amide or sulfonamide-containing reactant or salt thereof under the conditions set forth above. The product is recovered as a solid such as by precipitation or by removing the solvent. Representative suitable solvents for the fluorocarbon polymer precursor include halogenated solvents such as polychlorotrifluoroethylene, for example Halocarbon oil, perfluoroalkylamines, for example Fluorinert FC-70, or the like.

In one embodiment, the perfluorocarbon comprises $^{19}F$. In one embodiment, polymers comprising $^{19}F$ are particularly useful in applications of this invention in imaging and diagnostics, and offer several advantages over traditionally used agents in such applications, in particular in magnetic resonance imaging (MRI). $^{19}F$ is a magnetically active nucleus with a relative intrinsic sensitivity 83% of $^{1}H$. The normal concentration of MRI-observable fluorine in tissue is extremely low. Most tissue fluorine is concentrated in bone mineral as ionic fluoride and therefore exhibits an NMR signal with solid state (broad line) characteristics (extremely short T2) that does not contribute to the image brightness using conventional MRI techniques. As a consequence, use of polymers/micelles of this invention, comprising $^{19}F$ in MRI will result in a contrast-to-noise ratio that is very high as compared to the gray-scale images typical of $^{1}H$-MRI, with the quality of $^{19}F$-MRI limited only by the signal-to-noise ratio of the acquired image.

Another useful property of $^{19}F$ for MRI imaging is the linear relationship between the $^{19}F$ spin-lattice relaxation rate ($R_1 1/T_1$) and local oxygen partial pressure, which provides a means for non-invasive $pO_2$ measurement using $^{19}F$-MRI. The increasing R1 with increasing pO2 also leads to an increase in pixel brightness in $T_1$-weighted $^{19}F$-MR images. This property may be exploited in various applications using the polymers/micelles of this invention, such as, for example, in assessing tumor growth and development (see, for example, Song, Y., et al., NIR spectoscopy. In: Dunn and Swartz (eds.), Oxygen Transport to Tissue XXIV, pp. 225-236: Kluwer Academic/Plenum Publishers, 2003), in evaluating respiratory function (see, for example, Thomas, S. R., et al. Investigative Radiology, 32: 29-38, 1997), in ventilation (see, for example, Laukemper-Ostendorf, S., et al. Magnetic Resonance in Medicine, 47: 82-89, 2002), and other applications (see, for example, Noth, U., et al., Magnetic Resonance in Medicine, 42: 1039-1047, 1999; Williams, S. N. O., et al., Biotechnology and Bioengineering, 56: 56-61, 1997). In another embodiment, the polymers/micelles of this invention may further find application in cancer imaging, wherein a subject may breathe oxygen-enriched air during $^{19}F$-MRI imaging of the perfluorocarbon-containing polymers/micelles of this invention, where increased $O_2$ inspiration leads to a local $pO_2$ enhancement, or find application in measuring gastric emptying and gastrointestinal transit time in by gavage, and/or imaging pulmonary pathways with fluorinated gases.

In other embodiments, the polymers/micelles of this invention and compositions comprising the same may find application in $^{19}F$-MR spectroscopy (MRS), imaging (MRI), and spectroscopic imaging (MRSI) for in vivo quantitative metabolic mapping, as a tool for pharmacokinetic studies, such as, for example, uptake with the chemotherapeutic agent 5-fluorouracil and the selective serotonin reuptake inhibitors fluvoxamine and fluoxetine and their metabolites.

In one embodiment, $^{19}$F MRI may have a conservative detection limit of about 20 µM with a 3T magnet (assuming a linear variation of signal to noise ratio with field strength and inversely with coil diameter), dropping to about 10 µM in a 7T magnet. Moreover, it is expected that the very short $^{19}$F T1 of 140 ms (which increases the signal to noise ratio achievable in a given scanning time) reported by Kimura, et al. (Magnetic Resonance Imaging, 22: 855-860, 2004) will not occur in vivo, in using the polymers/micelles of this invention. Further, in one embodiment of this invention, additional loading of $^{19}$F may be accomplished using the micelles and compositions of this invention, enhancing the signal.

In another embodiment, the sensitivity of MRI detection of the $^{19}$F containing polymers/micelles of this invention can potentially be increased several fold by other approaches. The large chemical shifts of fluorine generally result in perfluorocarbons having complex chemical shift spectra, yielding groups of widely separated resonances corresponding to the different chemical environments of fluorine in these molecules. Within the chemical shift bands, there are resolved or unresolved isotropic homonuclear J-coupling patterns. $^{19}$F images may be plagued with multiple, at times overlapping, ghost images that result from the convolution of the ideal images with the chemical shift spectra. The phase modulation due to the J-coupling, which is not refocused by 180 degree RF pulses, creates additional artifacts. Typically, this situation is addressed, by using chemical shift selective pulses to image only one resonance band, thereby wastefully discarding the bulk of the potentially usable fluorine signal.

In one embodiment, a means of overcoming the chemical shift artifact is to use weak imaging gradients such that the projections of different chemical shift lines do not overlap; the separate projections may then be combined to form a single image of full signal to noise ratio. In one embodiment, this technique is useful with very high field magnets where the chemical shift frequency differences are very large, or in another embodiment, in situations where the sensitivity is low and therefore weak gradients and low spatial resolution (which preserve the signal to noise ratio) are needed.

In another embodiment, a means of overcoming the chemical shift artifact is via deconvolving the chemical shift spectrum from raw image data, as described (Busse, L. J., et al. Medical Physics, 13: 518-524, 1986).

Advantages of optical imaging methods, as described herein, include the use of non-ionizing low energy radiation, high sensitivity with the possibility of detecting micron-sized objects, continuous data acquisition, and others. At the near infrared region between 700 and 900 nm, absorption by intrinsic photoactive biomolecules is low and allows light to penetrate several centimeters into the tissue. Moreover, imaging in the near-infrared (NIR) region has minimal tissue autofluorescence, which dramatically improves the target/background ratio. Optical imaging can be carried out at different resolutions and depth penetrations. Fluorescence-mediated tomography (FMT) can three-dimensionally localize and quantify fluorescent probes in deep tissues at high sensitivity, and NIR fluorochromes may be coupled to affinity molecules, which may serve, in other embodiments, as targeting agents (see, for example, Becker, A., et al. Nature Biotechnology, 19: 327-331, 2001; Folli, S., et al. Cancer Research, 54: 2643-2649, 1994).

In another embodiment, the polymers/micelles of this invention allow for the combination of different imaging modalities.

In another embodiment, the polymers, micelles, compositions, or combinations thereof of this invention may comprise halogens, as described herein, such as, for example, fluorine or iodine. In one embodiment, any isotope of the halogen may be used in the polymers, micelles, compositions, or combinations thereof of this invention, and according to the methods of this invention, and may find application in various imaging means, which make use of specific isotopes, as will be appreciated by one skilled in the art.

In one embodiment, this invention provides for the combination of two imaging modalities which enable MR imaging using $^{19}$F or iron oxide, for example, as a contrast agent and a fluorescent label, such as the Cy5.5 dye as a near-infrared fluorescent (NIRF) probe. Cy5.5 can be coupled to one functional group on the trifunctional linking molecule in place of a side chain. Combined MR/optical probes may be used, in some embodiments, for imaging enzymatic activity, such as for example, protease activity as described (Josephson, L., et al. Bioconjugate Chemistry, 13: 554-560, 2002; Kircher, M., et al. Molecular Imaging, 1: 89-95, 2002). In some embodiments, such combination polymers/micelles enable specific recognition of a desired tissue, for example, produce a high resolution signal on MR images, and allow for real-time continuous data acquisition by NIRF imaging.

In another embodiment, the polymers are synthesized enzymatically. In one embodiment, the enzymes used to synthesize the polymers or micelles of this invention comprise lipases, such as, for example *Candida antarctica* lipase, or in another embodiment, lipase A, or in another embodiment, lipase B. In another embodiment, the enzyme may comprise an esterase, or in another embodiment, a protease, such as, for example papain or chymotrypsin. In one embodiment, molecular weight of the hydrophilic units is chosen such that its ability to affect polymerization is considered. In one embodiment, the polymer is functionalized with for example, an alkyl group of varying chain length, comprising a polar functionality at the end of the chain.

Polymers obtained by methods as described herein can be characterized by methods well known in the art. For example, the molecular weight and molecular weight distributions can be determined by gel permeation chromatography (GPC), matrix assisted laser desorption ionization (MALDI), and static or dynamic light scattering. Physical and thermal properties of the polymer products can be evaluated by thermal gravemetric analysis (TGA), differential scanning calorimetry (DSC), or surface tensiometer; the chemical structures of the polymers can be determined by, e.g., NMR (1H, 13C NMR, 1H-1H correlation, or 1H-13C correlation), IR, UV, Gas Chromatography-Electron Impact Mass Spectroscopy (GC-EIMS), EIMS, or Liquid Chromatography Mass Spectroscopy (LCMS).

In another embodiment, incorporation of perfluorocarbons within the polymers, micelles and compositions of this invention allows for the following advantages, in applications of $^{19}$F-MRI imaging: such use facilitates much higher signal-to-noise ratio and greater sensitivity compared to protons because of the absence of 19F background signals; fluorine is prepared at high concentration in the form of a perfluorocarbon contained within a unique self-assembling polymeric micelle that is small enough to be taken up by cells; and if the micelle exterior is functionalized with a ligand that binds to a receptor found on most solid tumors but not on normal cells, the resulting receptor-mediated endocytosis greatly enhances selectivity for tumor tissue.

The structure of an embodiment of this invention, a self-assembling, alternating copolymer micelle, is shown schematically in FIG. 1. Each polymer, in this embodiment, consists of a hydrophilic polyethylene glycol (PEG) segment (molecular weight main chain 60-10,000) bound to a linker (aromatic or peptide bond) to which a hydrophobic side chain is bound (via ether or ester linkages) that is terminated by a hydrophobic or hydrophilic group. When dissolved in water above the critical micelle concentration, about 8 to 12 polymeric units self assemble into a spherical micelle consisting of a compact core surrounded by an outer envelope of PEG loops that provide biocompatibility. The micelles have a molecular weight of about 100-200,000 and a hydraulic radius ranging from about 10 to 30 nm. Additional agents can be encapsulated in the core. These micelles can be taken up intact by cells, as demonstrated by with micelles fluorescently labeled on the main chain and on the cargo. Micelle synthesis in which the side chain is a perfluorocarbon was accomplished, using perfluoroctyl bromide, and micelles were formed having a 30 nm radius, and containing 28% (w/v) fluorine. Additional perfluorocarbon cargo can be encapsulated inside each micelle, substantially increasing the fluorine content. Only $10^5$ of these micelles are estimated to be needed in a cell to achieve a concentration on the order of 1 mM, which is the minimum required for effective $^{19}F$ imaging. It has been shown that intravenously administered perfluorocarbon emulsions with diameters 3 to 4 times larger preferentially accumulate in the interstitial space of solid tumors and can be detected using $^{19}F$ NMR spectroscopy and imaging.

In another embodiment, the polymers form micelles or nanoparticles, which range in size from 5-1000 nm. In one embodiment, the size range is from 25-200 nm. In one embodiment, the size range is from 30-200 nm, or in another embodiment, the size range is from 35-200 nm, or in another embodiment, the size range is from 40-200 nm, or in another embodiment, the size range is from 45-200 nm, or in another embodiment, the size range is from 50-200 nm, or in another embodiment, the size range is from 75-200 nm, or in another embodiment, the size range is from 100-200 nm, or in another embodiment, the size range is from 125-200 nm, or in another embodiment, the size range is from 150-200 nm, or in another embodiment, the size range is from 175-200 nm, or in another embodiment, the size range is from 35-75 nm, or in another embodiment, the size range is from 50-100 nm, or in another embodiment, the size range is from 75-200 nm, or in another embodiment, the size range is from 75-150 nm, or in another embodiment, the size range is from 50-125 nm, or in another embodiment, the size range is from 20-100 nm, or in another embodiment, the size range is from 20-125 nm.

In another embodiment, the hydrophilic polymer molecular weight may be varied. In one embodiment, the molecular weight of the hydrophilic polymer may range from 150-200,000 Da.

In one embodiment, the compositions of this invention, which comprise a polymer and/or micelle of this invention is biocompatible, and in another embodiment, may comprise pharmaceutically acceptable carriers or excipients, such as disclosed in Remington's Pharmaceutical Sciences, Mack Publishing Company, Easton, Pa, USA, 1985. The polymers, micelles and/or compositions of this invention may be used in the treatment or diagnosis of certain conditions such as in tagging, detecting and/or removing cancer cells for example from a sample or tissue.

In another embodiment, this invention provides a process for producing an amphiphilic polymer comprising perfluorocarbons, the process comprising the steps of:

contacting a dialkyl 5-hydroxy-isophthalate, a dialkyl 5-alkoxy-isophthalate, a dialkyl 5-amino-isophthalate, any derivative thereof or any combination thereof with a polyethylene glycol to form an amphiphilic copolymer; and linking a perfluorocarbon to said amphiphilic copolymer, thereby being a process for producing amphiphilic polymers comprising perfluorocarbons.

In one embodiment, a chemo-enzymatic approach for the synthesis is used. In one embodiment, the processes of this invention may further comprise the step of protecting the amino group of dialkyl 5-amino-isophthalate with an amino protecting group.

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: New York, 1991).

In another embodiment, the processes of this invention may further comprise the step of protecting the hydroxy group of a dialkyl 5-hydroxy-isophthalate with an hydroxy protecting group.

In one embodiment, enzymatic polymerization of a hydrophilic with a multifunctional linking molecule to form the copolymer backbone is conducted initially. In one embodiment, the linking moiety is dissolved in the hydrophillic liquid without any additional solvent, enzyme is added, and polymerization is carried out at high temperature, for example at about 90° C., under vacuum.

In one embodiment, the process of this invention comprises synthesis of a polymer comprising a perfluorocarbon, wherein the perfluorocarbon is linked to a hydroxyl group, amino group, or combination thereof of the isophthalate, and in one embodiment, the attachment of perfluorocarbon to isophthalate is via an esteric bond, an amide bond, or a combination thereof.

In one embodiment, the synthesis of the basic polymer takes place in two steps, which comprise, inter-alia, attachment of a targeting agent and/or labeling agent subsequent to the basic polymer formation.

In one embodiment, the hydrophilic moiety is a PEG oligomer (n=10-34) and the multifunctional linker is dimethyl 5-hydroxyisophthalate.

According to this aspect, and in one embodiment, the reaction is a trans-esterification, and the methanol formed during the reaction is removed under vacuum. In one embodiment, the method employs the use of lipase B from *Candida antartica*, and takes advantage of the regioselectivity of the enzyme, such that the phenolic group does not take part in the polymerization, thereby giving a polymer with a reactive functional group. This reactive functional group, in turn, may be used for further chemical reactions, in this case attachment of a hydrophobic group with either an ether or ester linkage using standard group replacement chemistry, as will be appreciated by one skilled in the art.

In one embodiment, the enzyme may be immobilized within porous poly(methyl methacrylate) beads, such as, for example, that available as Novozyme 435 from Novozyme A/S).

In other embodiments, any number of multifunctional linkers may be used, such as, for example, those with hydroxy or amino functional group and a variety of hydrophobic moieties may be attached with and without an additional terminal functional group. For example, and in other embodiments, polymers comprising linkers such as dimethyl 5-amino isophthalate, amino malonic acid, aspartic and glutamic acid as linkers, have been attached to hydrocarbon chains which have a functionality of hydroxy, carboxy, amino, or guanidinyl groups at the end of the chain, by methods well known in the art [see for example, Kumar, R., et al. Journal of the American Chemical Society, 126: 10640-10644, 2004; Kumar, R., et al., Green Chemistry, 6: 516-520, 2004; Kumar, R., et al., Journal of Macromolecular Science: Pure and Applied Chemistry, A40: 1283, 2003; Tyagi, R., et al., Polymer Preprint, 44: 778, 2003; Sharma, S. K., et al. Polymer Preprint, 44: 791, 2003; Sharma, S. K., et al., Journal of Macromolecular Science: Pure and Applied Chemistry, A41: 1459, 2004, all of which are incorporated herein by reference].

In one embodiment, the linkage at the aromatic oxygen may be an ester or ether linkage. For example, if an aminophthalate is used, the connection of the side chain is an amide link.

In other embodiments, the length of the PEG or hydrophilic segment may be varied over a wide range, such as disclosed, for example in Kumar, R., et al. Journal of Macromolecular Science, A39: 1137-1149, 2002, such that the hydrophilicity/hydrophobicity ratio for the polymer may be controlled. In other embodiments, the polymerization conditions may be controlled, such that a structure is obtained in which hydroxyl groups of the PEG component are available on both ends of the polymer chain, which in other embodiments, may be used for subsequent chemical modification. These hydroxyl groups may be used, in other embodiments, to attach a targeting agent, such as for example, the peptide EPPT1, as exemplified herein, or, in another embodiment, a labeling agent, such as, for example, a fluorescent compound.

The polymers may form micelles, when in solution. Characterization of the polymers in aqueous solution with light scattering techniques, demonstrates formation of nanoparticles via a self-assembly process with a PEG external surface and a hydrophobic internal cavity. The ratio of the radius of gyration, Rg, (static light scattering) to the hydrodynamic radius, Rh, (dynamic light scattering) is about 1.75, indicating that the nanoparticles correspond to a hollow spheroidal structure. Attachment of functional groups at the end of the hydrophobic chains allows modification of the cavity of these nanospheres, which affects their size and stability as well as the nature of cargo that can be encapsulated. Static light scattering of the nanospheres gives Rg in the range of 10-80 nm. The size of the nanospheres and their stability are influenced by the length of the PEG oligomers and the nature of the hydrophobic group. The incorporation of hydrophobic side chains may add to the stability of the micelles.

In one embodiment, the polymers will have a molecular weight of around 200,000 Da and contain 10-12 copolymer chains per nanosphere, each about 20,000 Da in molecular weight.

A wide variety of small molecules including drugs may be encapsulated within the micelles of this invention. Larger molecules such as proteins (insulin) and polysaccharides (inulin) have also been encapsulated since the nanospheres may adjust to the size of the encapsulant molecule in the self assembly process. In order to encapsulate smaller molecules, a protocol as described (Kumar, R., et al., Journal of the American Chemical Society, 126: 10640-10644, 2004; Sharma, S. K., et al., Chemical Communication 23: 2689-2691 2004) may be used. The polymer and cargo are dissolved together in an organic solvent, such as chloroform, and then the solvent is evaporated to dryness. The residue is dissolved in water and any unencapsulated material removed by filtration. The aqueous solution is freeze-dried, kept until needed, and then reconstituted with water to give clear solutions of the encapsulated material. The amount of encapsulant as a fraction by weight may be determined by several methods. When the UV absorptivity of the encapsulant is sufficiently different from the polymer, UV spectroscopy may be used. In other cases, $^1$H-NMR may be used, as described in Sharma, supra. Typically, a ratio of 1:4 or 1:5 cargo to polymer weight ratios are used. As the ratio increases, the fractional mass of the cargo increases, and the nanoparticle size increases until a maximum is reached.

The choice of starting reagents used to construct the polymers of this invention may be tailored, for example, for the attachment of different types of pendant groups, for example to a hydroxyl group, including alkyl or alkenyl chains, aryl groups, carboxyl-containing groups, amino groups, ammonium groups, and/or additional hydroxyl groups. In another embodiment, appropriate choice of the pendant group functionalities, enables enhanced polymer interaction with incorporated molecules, such as therapeutic compounds, fluorochromes, perfluorocarbons, etc., for optimal conjugation of the various functional groups herein described.

For example, a carboxyl-containing functional pendant group can interact with nitrogen bases (e.g., primary, secondary, or heterocyclic amines), and can form Schiff bases under appropriate conditions. By choosing appropriate encapsulation conditions, the resulting structure can be formed in such a way that the drug is well held in the core of the micelle, protected from the physiological milieu. As another example, a carboxylic acid group on the drug can be ion-paired with a pendant amine (e.g., a secondary or tertiary amine). The resulting ion pair can be formed in such a fashion that it resides substantially within the core of the micelle. Such pendant groups can be incorporated into the polymer with relative ease, using well-known synthesis methods. Thus, the polymers can be readily tailored to create vehicles that meet the specific requirements of a given guest drug molecule, for example, and in one embodiment, or any other molecule for delivery, using the polymers and/or micelles of this invention.

Synthesis of Fluorine-containing Nanoparticles

Fluorine incorporation into the base copolymer may be via any number of standard methods of formation of ester or ether linkages to attach a perfluorinated chain. For example, and in one embodiment of this invention, the amphiphilic copolymer (with PEG, n=15) is mixed with perfluoro octanoyl chloride under basic conditions to attach an acyl perfluoro group to a phenolic moiety as the hydrophobic side chain. The attachment may be confirmed with IR spectroscopy and $^{19}$F-NMR. A fluorine-modified polymer thus formed demonstrated nanoparticles with an Rg of about 75 nm, as determined by static light scattering. It contained 28% (w/w) fluorine, corresponding to about 3,800 $^{19}$F atoms per nanoparticle.

The amphiphilic copolymers with perfluorocarbon side chains were then used to further encapsulate 1,1,2,2,-tetrahydro perfluorododecanol (20% w/w) using the same procedure as described above. The amount of perfluorocarbon cargo encapsulated by the fluorinated polymer was determined by integration of fluorine NMR spectra. The entire particle contained 42% (w/w) fluorine, corresponding to almost 6,000 $^{19}$F atoms per nanoparticle. Loading may be increased by at least a factor of two to 12,000 $^{19}$F atoms per nanoparticle. Assuming a cell volume of $10^3$ μm$^3$, uptake of $10^5$, $10^6$, or $10^7$ of the nanoparticles per cell is obtainable, and result in cellular fluorine concentrations of about 2, 20, or 200 mM, respectively, amounts sufficient for efficient imaging, in clinical settings.

The physical and chemical properties of the polymers/microspheres of this invention may readily be determined with standard techniques such as IR spectroscopy, NMR spectroscopy, gel permeation chromatography, and light scattering (dynamic and static).

In one embodiment, the targeting agent is a peptide, which in one embodiment binds to an underglycosylated mucin-1 protein, which in one embodiment is EPPT1, as described herein. In one embodiment, the EPPT1 peptide is based on the CDR 3 VH and framework regions of the idiotype of a murine antitumor monoclonal antibody ASM2 directed against the polymorphic epithelial human mucin epitope (Hussain, R., et al. *Peptides: Chemistry, Structure, and Biology*. Proceedings of the 14th American Peptide Symposium, England, 1996, pp. 808-809).

In one embodiment, synthesis of the polymer comprising the EPPT1 peptide will comprise polymerization with two linkers, one of which will be in a small amount (1-5%) to give the polymer as shown in FIG. 6. The synthesis is conducted such that PEG hydroxy groups are at the ends of the chain, and perfluorocarbon side chains are attached to the linker hydroxyls by standard acylation procedures to form the ester linkage with the polymer backbone. Numerous fluorine-containing polymers may be prepared via this route, including the formation of $(CF_2)_8CF_3$, $(CF_2)_6CF_3$, $(CF_2)_3CF_3$, $CH_2OCH_2(CF_2)_8CF_3$, $CH_2OCH_2(CF_2)_6CF_3$, $CH_2OCH_2(CF_2)_4CF_3$ or $CH_2OCH_2CH_2(CF_2)_{11}CF_3$. In other embodiments, the synthetic processes of this invention are highly flexible, enabling the variation of the chain length (from 5 to 13 carbons) and the relative number of fluorine atoms to alter the hydrophobicity of the side chain.

The effect of any of the parameters on polymer/micelle-loading and stability may be evaluated, by any number of methods known to one skilled in the art, and a number of encapsulating materials may be evaluated concurrently, including perfluorodecalin, bromo-perfluoroheptane, and perfluoro-crown ether. Cy5.5 may be attached to the polymers to enable NIRF determination, EPPT1 peptides for targeting, and radioiodine for cell binding and biodistribution studies.

In one embodiment, the process of this invention comprises linking a perfluorocarbon to the amphiphilic copolymer via, inter-alia, converting the amino group (—NH2) of the isophthalate to —NH—R1, wherein R1 is as defined herein.

In one embodiment, the process of this invention comprises linking a perfluorocarbon to an amphiphilic copolymer via, inter-alia, alkylating the hydroxy group (—OH) of the isophthalate to produce —$(CH_2)_q$CO—$R_2$, wherein $R_2$ is as defined herein.

In another embodiment, this invention provides a polymer or micelle, or composition comprising a product of a process of this invention.

In another embodiment, this invention provides a method of imaging a cell, the method comprising the steps of contacting a cell with an amphiphilic polymer of this invention and imaging said cell, whereby said polymer enables the imaging of said cell.

Attachment of Fluorescent Probe

Fluorochromes may readily be attached to a polymer of this invention, and represent an embodiment thereof. As exemplified herein, Rhodamine B was converted to its acid chloride using oxalyl chloride. Treatment of the polymer (substituted with a decane chain as the hydrophobic group) with the acid chloride and base formed an ester linkage with the $CH_2OH$ groups at the ends of the polymer chains, binding it covalently to the polymer, and attachment did not interfere with nanosphere formation as determined by light scattering.

Neuroblastoma cells incubated with nanospheres with Rhodamine B attached to the polymer, and brilliant green loaded within the spheres, showed nanosphere polymer and cargo penetrated cells, as evidenced by colocalization of the two fluorescent signals, indicating that the nanoparticles entered the cell with its cargo intact.

In one embodiment, a fluorescent molecule is attached to a polymer of this invention. In one embodiment, the fluorescent molecule is Cy5.5. In one embodiment, Cy5.5 is attached to amine groups of the base polymer and non-reacted dye may be removed by any number of conventional means, such as, for example, via column chromatography.

In another embodiment, the fluorescent molecule may be introduced within a targeting moiety which is coupled to a polymer of this invention. For example, an EPPT1 peptide (YCAREPPTRTFAYWG-SEQ ID NO: 1) is modified to introduce a FITC label, to produce a final peptide with the following sequence: Y-C(ACM)-A-R-E-P-P-T-R-T-F-A-Y-W-G-K(FITC)K (SEQ ID NO: 2).

In one embodiment, peptides of this invention may be purified from appropriate sources, or in other embodiments, may be synthesized, by means well known in the art. In one embodiment, peptides may be synthesized on an automatic synthesizer using Fmoc chemistry with HBTU and HOBT. They may be further purified by C18 reverse phase HPLC. Molecular weight may be determined by MALDI mass spectroscopy.

In one embodiment, both the targeting moiety and the polymer may be labeled with fluorescent markers, or, in another embodiment, any other agent, as described. In one embodiment, such conjugation may be accomplished by any number of methods known in the art, such as, for example, that of Zalipsky, et. al. (Advanced Drug Delivery Reviews, 54: 459-476, 2002), or Roberts, M. J. et al. Advanced Drug Delivery Reviews, 54: 459-476, 2002).

In one embodiment, polymers or micelles of this invention may be radiolabeled. For example, incorporation of Na $^{125}$I may be accomplished using the Iodogen method (Pierce, Rockford, Ill.) using available Tyr within the peptide sequence, in conjugated polymers. In another embodiment, the basic polymer backbone may be radiolabeled with the same procedure via substitution of the isophthalate ring similar to that of the tyrosine aromatic ring, in peptide or protein-conjugated polymers.

In another embodiment, the methods of this invention are directed to the imaging of individual cells, a group of cells, a tissue, an organ or a combination thereof.

In one embodiment, imaging is accomplished with computed tomography, computed radiography, magnetic resonance imaging, fluorescence microscopy, angiography, arteriography, or a combination thereof. In one embodiment, a cell is contacted with a polymer of this invention, ex-vivo, and is subsequently implanted in a subject. In one embodiment, the cell is inter-alia, labeled with a labeling agent as described herein, and may further comprise a therapeutic compound, and/or in another embodiment, the theraepeutic compound is labeled with a labeling agent, and in one embodiment, the delivery of the cell and/or therapeutic compound may be verified by imaging the labeling agent.

In one embodiment, the imaging methods of this invention are conducted on a subject. In another embodiment, the imaging methods are conducted on a sample taken from a subject. In one embodiment, the subject has or is suspected of having cancer, or in another embodiment, atherosclerotic lesions, or in another embodiment, is infected, or in another embodiment, has ischemica.

In one embodiment, the imaging methods as described herein may comprise near infrared fluorescence imaging. In one embodiment, an advantages of such optical imaging methods may include the use of non-ionizing low energy radiation, high sensitivity with the possibility of detecting micron-sized objects, continuous data acquisition, and the development of potentially cost-effective equipment. Optical imaging can be carried out at different resolutions and depth penetrations. Fluorescence-mediated tomography (FMT) can three-dimensionally localize and quantify fluorescent probes in deep tissues at high sensitivity. Several NIR fluorochromes have recently been coupled to affinity molecules (Becker, A., et al. Nature Biotechnology, 19: 327-331, 2001; Folli, S., et al Cancer Research, 54: 2643-2649, 1994, and can be adapted to comprise the polymers or micelles of this invention, as will be appreciated by one skilled in the art.

In one embodiment, the imaging methods as described herein may comprise nuclear imaging methods. Nuclear imaging is based on labeling molecules with a radioactive atom before their release in the system under study. Since photons of relatively high energy (>80 keV) can escape from the human body, it is possible to follow over time the 3D spatial distribution of the radioactive tracer through detection of the emitted radiation. A large variety of isotopes can be imaged. Their broadest classification is perhaps that in gamma and positron emitters: the former family is at the basis of single photon emission methods (such as planar scintigraphy and tomography, or SPECT), and the latter is used in Positron Emission Tomography (PET). Unlike in MRI or computed tomography (CT), the signal detected in nuclear imaging techniques is the radioactive emission of a single atom. Because these emissions are specific to the radioisotope used, and because it is possible with standard physics instrumentation to detect the emission of a single atom, nuclear imaging enjoys the advantages of both high specificity and sensitivity. Structural information, however, may be obtained only as far as the radiotracer redistributes following anatomical structures. Resolution of clinical scanners may be limited to about 5-6 mm for PET and ~1 cm for SPECT, thus, nuclear imaging methods are often used to complement the information provided by CT and/or MRI scans in the context of multimodality imaging, and may be applied in this manner herein, representing an embodiment of this invention. In one embodiment, nuclear imaging is used in particular because of its sensitivity to extremely small quantities of matter. For example, it has recently been estimated that PET can detect as few as a cluster of 250 cells each bearing 30 Bq of $^{18}$F, which corresponds to 2.1 fg.

While PET techniques achieve good resolution with high sensitivity (2-4%), common positron emitters such as $^{18}$F has a relatively short half-life, which may affect it's widespread applicability. In one embodiment, however, nanoparticle encapsulation as described herein, may lengthen this half-life and enhance it's applicability.

In another embodiment, different iodine isotopes can be chosen for radioactive labeling of compounds. In one embodiment, $^{123}$I, $^{125}$I and $^{131}$I can be used to obtain molecules with the same chemical and biological characteristics but different imaging and dosimetric properties. 131I In one embodiment, the isotope for imaging is 123I (159 keV), or in another embodiment, 37 MBq of $^{123}$I-MIBG, which results in an exposure to a radiation dose no higher than 1.8 MBq of $^{131}$I-MIBG.

In radioimmunotherapy (RIT), cytotoxic radiation from therapeutic radioisotopes is delivered to tumors via antibodies or peptides that bind to tumor-specific or tumor-associated antigens (116). Radioactive metal ions can be attached to an antibody through a metal chelating agent (117). One advantage for RIT over other immunotherapies, such as immunotoxins, is that there is no need to target every tumor cell to cause an antitumor effect at the cellular level because nontargeted cells can be irradiated and often killed by radiation from targeted neighboring cells. With immunotoxins, each tumor cell must be targeted for the antitumor effect to occur at the cellular level (116).

In another embodiment, some of the radioisotopes may serve a dual purpose, such as, in one embodiment, for imaging the sites to which the radioisotope is delivered, and in another embodiment, as part of radiotherapy, including radioimmunotherapy. In one embodiment, $^{131}$I and $^{90}$Y are used. $^{131}$I, in one embodiment, may be attached to an antibody or peptide by simple techniques (such as the IODOGEN or chloramine-T methods), and may be imaged by instrumentation which detects γ-emission, while β-emission serves for therapeutic application in the subject.

Delivery of Therapeutic Compounds

The micelles of this invention may be used to encapsulate any number of therapeutic agents, individually or in combination. Some examples of thereapuetic compounds are described herein, such as, for example, non-steroidal anti-inflammatory drugs such as aspirin and naproxen, or others as described hereinabove. In one embodiment, the terms "drugs" and "therapeutic compound" are interchangeable, and refer, in some embodiments to compounds producing symptom palliative effects, delay in severity of symptoms or disease progression, inhibition of disease, or any positive effect attributable to the therapy, or a combination thereof.

Delivery to a subject through various routes, for example, intravenously, intramuscularly, topically, etc., which may vary, in some embodiments, as a function of the desired site of delivery, or timing, or combination thereof.

Any number of assays may be utilized in order to verify that the drugs are delivered to the appropriate site, and are functional, and such assays will be tailored for the particular drug utilized As an example, a human cell line such as OM10.1 (Butera et al., AIDS Res. Hum. Retroviruses, 8:991-995, 1992), which is chronically infected with HIV-1, may be used to test antiviral activities of polymer encapsulated anti-HIV drugs, which is one embodiment of this invention. Such an assay may be conducted as described, in for example, Critchfield et al., AIDS Res. Hum. Retroviruses, 12:39-46, 1996). Anti-viral effects can be determined through a variety of assays, including measuring HIV-1 p24 antigen levels, for example, using a commercially available ELISA kit (Coulter), and for reverse transcriptase (RT) activity, using a commercially available chemiluminescent ELISA RT assay such as that sold by Boehringer Mannheim, each according to the manufacturer's instructions. Inhibition of viral cell-to-cell spread may be measured, in another embodiment, serving as an indicator of anti-viral efficacy, using a model system, for example, as described (Rabin et al, 1996; Sato et al., 1992).

It is to be understood that any assay for measuring a particular activity which is modulated by the therapeutic compound may be employed, as a means of determining the efficacy of the compound, in one embodiment, optimal loading of the compound, in another embodiment, timing and dosage, in another embodiment, or a combination thereof.

Targeting of Specific Agents Using the Polymers and Micelles of this Invention

FITC-labeled EPPT1 peptide-conjugated micelles were exemplified herein. Any number of cells or cell lines may be incubated with the tagged molecules and targeting of desired cells and/or uptake may be demonstrated by conventional means, including microscopy, FACS analysis, western blot analysis, and others.

In vivo imaging can be readily performed on subjects exposed to labeled polymers/micelles. MR-imaging or NIRF analysis may be used, as well as fluorescence microscopy of excised target tissue, the images of which may be compared to those obtained by MIR or NIRF.

In another embodiment, this invention provides a method of targeted delivery of at least one agent in a subject comprising the steps of administering to said subject an amphiphilic polymer of this invention, wherein said polymer comprises said agent and a targeting agent.

In another embodiment, this invention provides a method for detecting neoplastic cells in a subject, comprising contacting a cell in, or a cell derived from said subject with an effective tumor-detecting amount of an amphiphilic polymer of this invention, wherein said polymer comprises a targeting moiety specific for neoplastic cells; and detecting any of said polymer associated with neoplastic cells present in said subject.

In another embodiment, this invention provides a method of imaging a cell, the method comprising the steps of contacting a cell with an amphiphilic polymer of this invention and imaging said cell, whereby said polymer enables the imaging of said cell.

In another embodiment, this invention provides a method of targeted delivery of at least one agent in a subject comprising the steps of administering to said subject an amphiphilic polymer of this invention, wherein said polymer comprises said agent and a targeting agent.

In one embodiment, multiple targeting moieties, may be incorporated in the polymers or micelles of this invention. In one embodiment, multiples of the same targeting moiety will be incorporated, or in another embodiment, multiple targeting moieties, which target the same cell or tissue, may be incorporated.

In another embodiment, this invention provides a method for detecting neoplastic cells in a subject, comprising contacting a cell in, or a cell derived from said subject with an effective tumor-detecting amount of an amphiphilic polymer of this invention, wherein said polymer comprises a targeting moiety specific for neoplastic cells; and detecting any of said polymer associated with neoplastic cells present in said subject.

As used herein, the term "contacting a target cell" refers to both direct and indirect exposure of the target cell to a polymer, micelle or composition of this invention. In one embodiment, contacting a cell may comprise direct injection of the cell through any means well known in the art, such as microinjection. It is also envisaged, in another embodiment, that supply to the cell is indirect, such as via provision in a culture medium that surrounds the cell.

Protocols for introducing the polymers, micelles or compositions of the invention to cells and subject may comprise, for example: direct uptake techniques, injection, receptor-mediated uptake (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals), and others, as will be appreciated by one skilled in the art. It is to be understood that any direct means or indirect means of intracellular access of polymers, micelles or compositions of the invention is contemplated herein, and represents an embodiment thereof.

In one embodiment, the cell which is targeted for uptake of a polymer, micelle or composition of this invention may include any epithelial cell, muscle cell, nerve cell, lung cell, kidney cell, liver cell, astrocyte, glial cell, prostate cell, professional antigen presenting cell, lymphocyte, M cell, or any other cell in the body, where the polymers or micelles or compositions of this invention may be useful.

In one embodiment, the polymers or micelles or compositions of this invention may be administered in any effective, convenient manner including, for instance, administration by intravascular (i.v.), intramuscular (i.m.), intranasal (i.n.), subcutaneous (s.c.), oral, rectal, intravaginal delivery, or by any means in which the polymers or micelles or compositions of this invention can be delivered to tissue (e.g., needle or catheter). Alternatively, topical administration may be desired for insertion into epithelial cells. Another method of administration is via aspiration or aerosol formulation.

For administration to mammals, and particularly humans, it is expected that the physician will determine the actual dosage and duration of treatment, which will be most suitable for an individual and can vary with the age, weight and response of the particular individual.

According to this aspect of the invention, the disease for which the subject is thus treated may comprise, but is not limited to: muscular dystrophy, cancer, cardiovascular disease, hypertension, infection, renal disease, neurodegenerative disease, such as alzheimer's disease, parkinson's disease, huntington's chorea, Creuztfeld-Jacob disease, autoimmune disease, such as lupus, rheumatoid arthritis, endocarditis, Graves' disease or ALD, respiratory disease such as asthma or cystic fibrosis, bone disease, such as osteoporosis, joint disease, liver disease, disease of the skin, such as psoriasis or eczema, ophthalmic disease, otolaryngeal disease, other neurological disease such as Turret syndrome, schizophrenia, depression, autism, or stoke, or metabolic disease such as a glycogen storage disease or diabetes. It is to be understood that any disease whereby expression of a particular protein, provision of a therapeutic protein, provision of a drug, inhibition of expression of a particular protein, etc., which can be accomplished via the use of the polymers, micelles or compositions of this invention is sought, is to be considered as part of this invention.

The following examples are presented in order to more fully illustrate some embodiments of the invention. They should, in no way be construed, however, as limiting the scope of the invention.

EXAMPLES

Example 1

Synthesis and Characterization of Novel Multi-modal Micelle Nanoparticle

A chemo-enzymatic approach (Kumar, R., et al. Journal of Macromolecular Science, A39: 1137-1149, 2002; Kumar, R., et al. Journal of the American Chemical Society, 126: 10640-10644, 2004) was developed for the design and synthesis of a complex polymer structure that forms nanospheres, which in one embodiment possesses targeted multi-modal imaging capability. The polymer self-assembles into spherical nanoparticles. Synthesis of the basic polymer takes place in two steps, following which, in one embodiment of the invention, attachment of a targeting peptide and fluorescent moiety may occur subsequent to the basic polymer formation.

Enzymatic polymerization of a PEG oligomer (n=10-34) with a trifunctional linking molecule (dimethyl 5-hydroxy-isophthalate) is conducted and results in the formation of a copolymer backbone (FIG. 1). The phthalate is dissolved in liquid PEG without any additional solvent, enzyme is added, and the polymerization is carried out at 90° C. under vacuum, as described (Kumar, R., et al. Journal of Macromolecular Science, A39: 1137-1149, 2002; Kumar, R., et al. Journal of the American Chemical Society, 126: 10640-10644, 2004). The reaction is a transesterification, with the methanol formed removed under vacuum. The method takes advantage of the regioselectivity of the enzyme (lipase B from *Candida antartica* immobilized within porous poly(methyl methacrylate) beads, available as Novozyme 435 from Novozyme A/S) such that the phenolic group does not take part in the polymerization, thereby giving a polymer with a reactive functional group. This reactive functional group may be used for further chemical reactions, in this case, attachment of a hydrophobic group with either an ether or ester linkage using standard group replacement chemistry.

The generality of the method enables utilization of a number of trifunctional linkers with hydroxy or amino groups as the remaining functional group and attaching a variety of hydrophobic moieties with and without an additional terminal functional group. Specifically, dimethyl 5-amino isophthalate (Kumar, R., et al. Biocatalytic "Green" synthesis of PEG-based aromatic polyesters: optimization of the substrate and reaction conditions. Green Chemistry, 6: 516-520, 2004), amino malonic acid (Kumar, R., et al. Journal of Macromolecular Science: Pure and Applied Chemistry, A40: 1283, 2003), and aspartatic and glutamic acid (Tyagi, R., et al. Polymer Preprint, 44: 778, 2003) have been used as linkers, and hydrocarbon chains which have a functionality of hydroxy (Kumar, R., et al. Journal of the American Chemical Society, 126: 10640-10644, 2004), carboxy (Kumar, R., et al. Journal of the American Chemical Society, 126: 10640-10644, 2004), amino (Sharma, S. K., et al. Polymer Preprint, 44: 791, 2003), or guanidinyl (Sharma, S. K., et al. Journal of Macromolecular Science: Pure and Applied Chemistry, A41: 1459, 2004) groups have been attached at the end of the chain. The linkage at the aromatic oxygen may be an ester or ether. If the aminophthalate is used, the connection of the side chain would be an amide link. The length of the PEG or hydrophilic segment may be varied over a wide range (Kumar, R., et al. Journal of Macromolecular Science, A39: 1137-1149, 2002), thus providing control of the hydrophilicity/hydrophobicity ratio as well as functionality. The polymerization conditions can be controlled such as to obtain a structure with the hydroxyl group of the PEG component available on both ends of the polymer chain for subsequent chemical modification. These hydroxyl groups are used to attach the peptide EPPT1 or to attach a fluorescent moiety if the peptide is absent.

Characterization of these polymers in aqueous solution with light scattering techniques (Chen, M. H., et al. Polymer Preprints, 44: 1199-1200, 2003) has shown that they form nanoparticles via a self-assembly process with a PEG external surface and a hydrophobic internal cavity (FIG. 2). The ratio of the radius of gyration, Rg, (static light scattering) to the hydrodynamic radius, Rh, (dynamic light scattering) is about 1.75, which indicates that the nanoparticles correspond to a spheroidal structure. Attachment of functional groups at the end of the hydrophobic chains allows modification of the cavity of these nanospheres, which affects their size and stability as well as the nature of cargo that can be encapsulated. Static light scattering of these nanospheres gives Rg in the range of 10-80 nm. The size of the nanospheres and their stability are influenced by the length of the PEG oligomers and the nature of the hydrophobic group. The nanospheres are quite stable as long as the side chains have significant hydrophobic character. They have a molecular weight around 200,000 Da and contain 10-12 copolymer chains per nanosphere, each about 20,000 Da in molecular weight.

Example 2

Encapsulation of Cargo Materials

A wide variety of small molecules including drugs may be encapsulated by the self-assembly process described in Example 1. Larger molecules such as proteins (insulin) and polysaccharides (inulin) have been encapsulated, since the nanospheres may adjust to the size of the encapsulant molecule in the self-assembly process. In order to encapsulate smaller molecules, a simple protocol is used (Kumar, R., et al. Journal of the American Chemical Society, 126: 10640-10644, 2004, Sharma, S. K., et al. Chemical Communication 23: 2689-2691, 2004). The polymer and cargo are dissolved together in an organic solvent, such as chloroform, and then the solvent is evaporated to dryness. The residue is dissolved in water and any unencapsulated material removed by filtration. The aqueous solution is freeze-dried, kept until needed, and then reconstituted with water to give clear solutions of the encapsulated material. The amount of encapsulant as a fraction by weight has been determined by several methods. When the UV absorptivity of the encapsulant is sufficiently different from the polymer, UV spectroscopy is used. In other cases, $^1$H-NMR (Sharma, S. K., et al., supra) is used. Typically, a ratio of 1:4 or 1:5 cargo to polymer weight ratios has been used. As the ratio increases, the fractional mass of the cargo increases, and the nanoparticle size increases until a maximum is reached.

The attachment of targeting peptides was also evaluated. The chemistry of attachment of peptides was straight forward with peptides/proteins attached at one at the ends of the polymeric chains which, upon choosing the proper polymerization procedure, have the PEG chain at both ends. Since in one embodiment, nanospheres have 8-10 chains per particle, this should give 16-20 peptide units per particle.

A monomethoxy PEG chain was used to simulate the chemistry at the end of a long PEG chain. The terminal hydroxy group was activated by a succinimidyl ester according to the method of Miron and Wilchek (Miron, T. and Wilchek, M. Bioconjugate Chemistry, 4, 1993) as shown in the first scheme, FIG. 2B, which demonstrates the attachment of amino acids to Monomethoxy PEG 2000.

In each of the amino acid attachments, the same peaks in the NMR spectra changed. The peaks on the proton NMR spectra for the methylene protons (x) of PEG at 4.45 ppm and the succinimidyl ester at 2.56 ppm disappeared over a period of 60 hours. The same PEG methylene protons (x) appeared at 4.1 ppm in the final amino acid attachment product. All of the amino acids, arginine, alanine, glycine and 2-fluorophenyl glycine, exhibited the same changes in the NMR (data not shown).

Figure 2A:
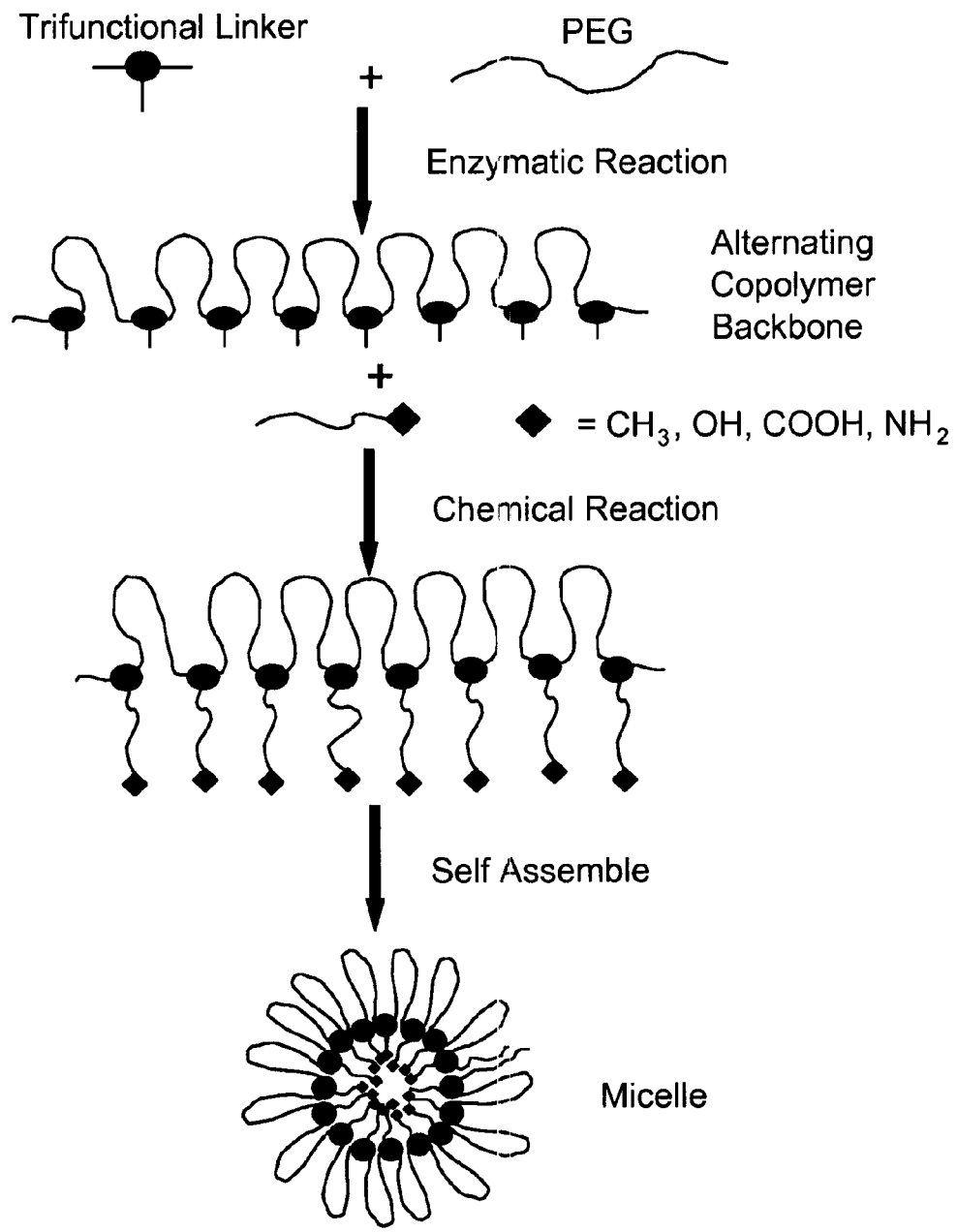
FIGS. 2a and 2b depict schemes for the formation of self-assembling alternating copolymer micelles.
Figure 2B:
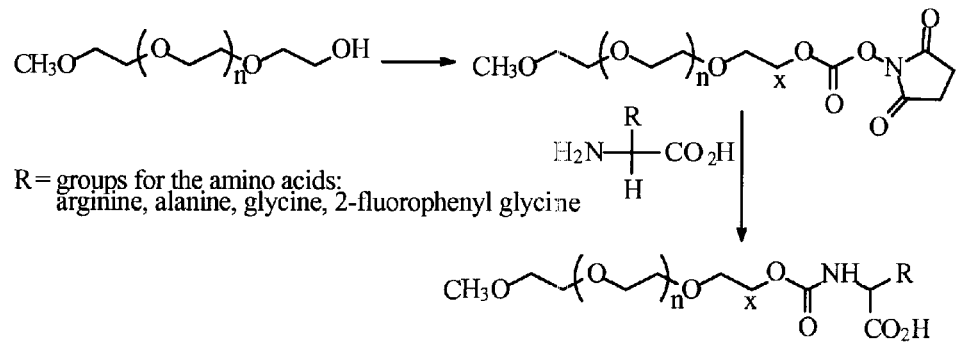
Figure 2B:
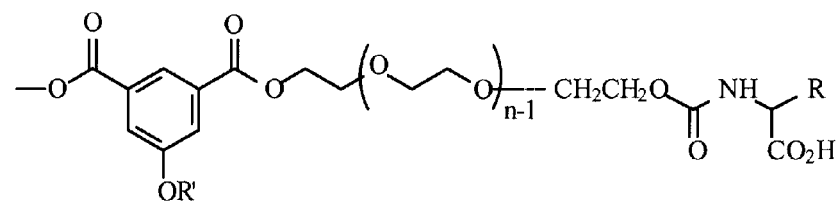
Figure 2B:
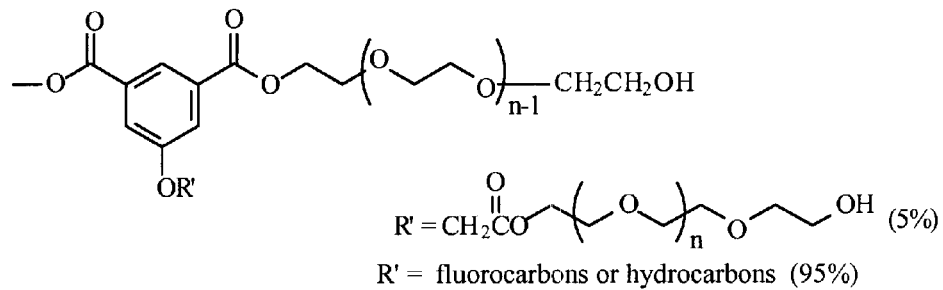

The same reactions were carried out with the basic polymer and the same amino acids, which provided the same results yielding the structures shown in Scheme 2, of FIG. 2B. The attachment of the EPPT1 peptide to the polymer using the same chemistry, was then conducted.

An alternative attachment for increasing the percentage of targeting peptides is to utilize the same chemistry and attach a small percentage (5%) of PEG units to the linker via a selective process to give additional reactive PEG hydroxy end groups. The structure of this selective process is shown in FIG. 2B, third scheme. The PEG units are located on the outside of the particle since they are highly hydrophilic. This would give a much greater number of peptide units per particle and yet would not disrupt the particle formation.

Example 3

Synthesis of Fluorine-containing Nanoparticles

Fluorine incorporation into the base copolymer was accomplished using standard methods of formation of ester or ether linkages to attach a perfluorinated chain. Each polymer consists of a hydrophilic polyethylene glycol (PEG) segment (molecular weight main chain 600-1500) bound to a linker (aromatic or peptide bond) to which a hydrophobic side chain is bound (via ether or ester linkages) that is terminated by a hydrophobic or hydrophilic group. When dissolved in water above the critical micelle concentration, about 8 to 12 polymeric units self assemble into a spherical micelle consisting of a compact core surrounded by an outer envelope of PEG loops that provide biocompatibility. The micelles have a molecular weight of about 100-200,000 and a hydraulic radius ranging from about 10 to 30 nm.

Figure 3A:
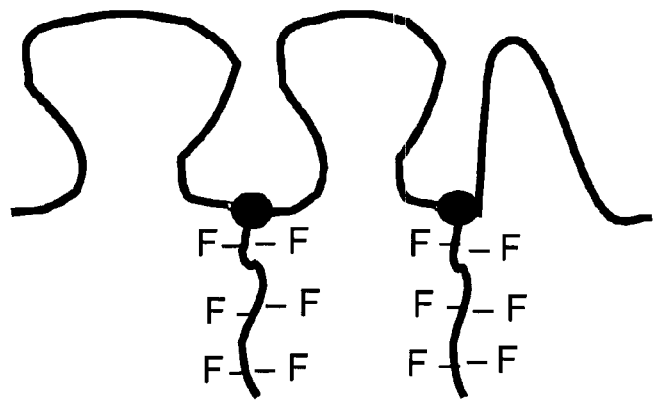
FIG. 3 depicts micelle nanoparticles with perfluorocarbon side chains and cargo and $^{19}F$ Spectra from perflurocarbon encapsulated 1,1, 2,2-tetrahydro perfluorodecanol particles.
Figure 3A:
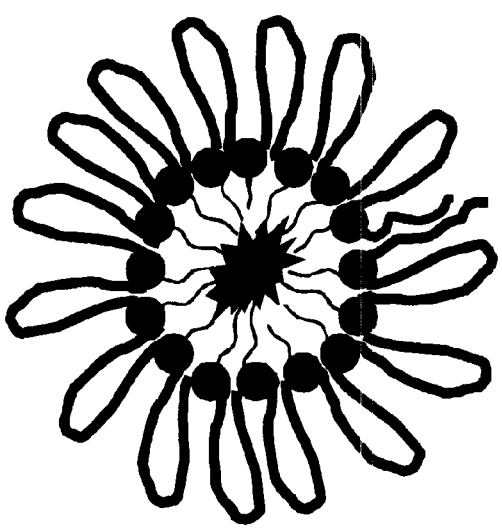

The amphiphilic copolymer (with PEG, n=15) was mixed with perfluoro octanoyl chloride under basic conditions to attach the acyl perfluoro group to the phenolic moiety as the hydrophobic side chain (FIG. 3A). The attachment was confirmed with IR spectroscopy and $^{19}$F-NMR. This fluorine-modified polymer formed nanoparticles with Rg about 75 nm as determined by static light scattering. It contained 28% (w/w) fluorine, corresponding to about 3,800 $^{19}$F atoms per nanoparticle.

Additional agents can be encapsulated in the core. Micelles, in which the side chain is a perfluorocarbon synthesized from perfluoroctyl bromide that forms a micelle with 30 nm radius containing 28% (w/v) fluorine has been synthesized. Additional perfluorocarbon cargo can be encapsulated inside each micelle to substantially increase fluorine content.

ticles per cell would lead to cellular fluorine concentrations of about 2, 20, 200, or 2,000 mM, respectively. The lower level would be adequate for $^{19}$F-MRI in the mouse; the upper levels would be more than enough for imaging humans.

Figure 3B:
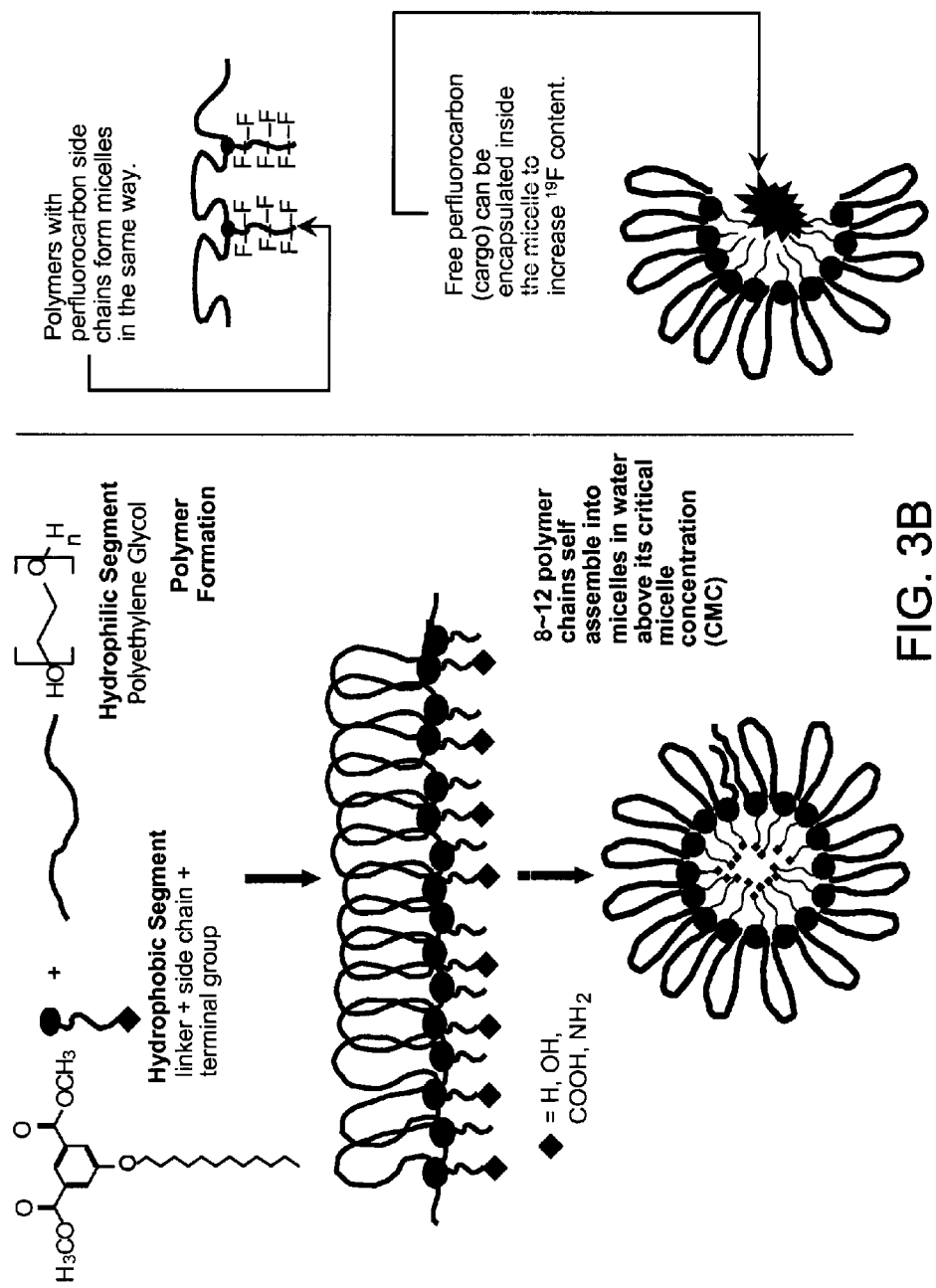
Figure 3C:
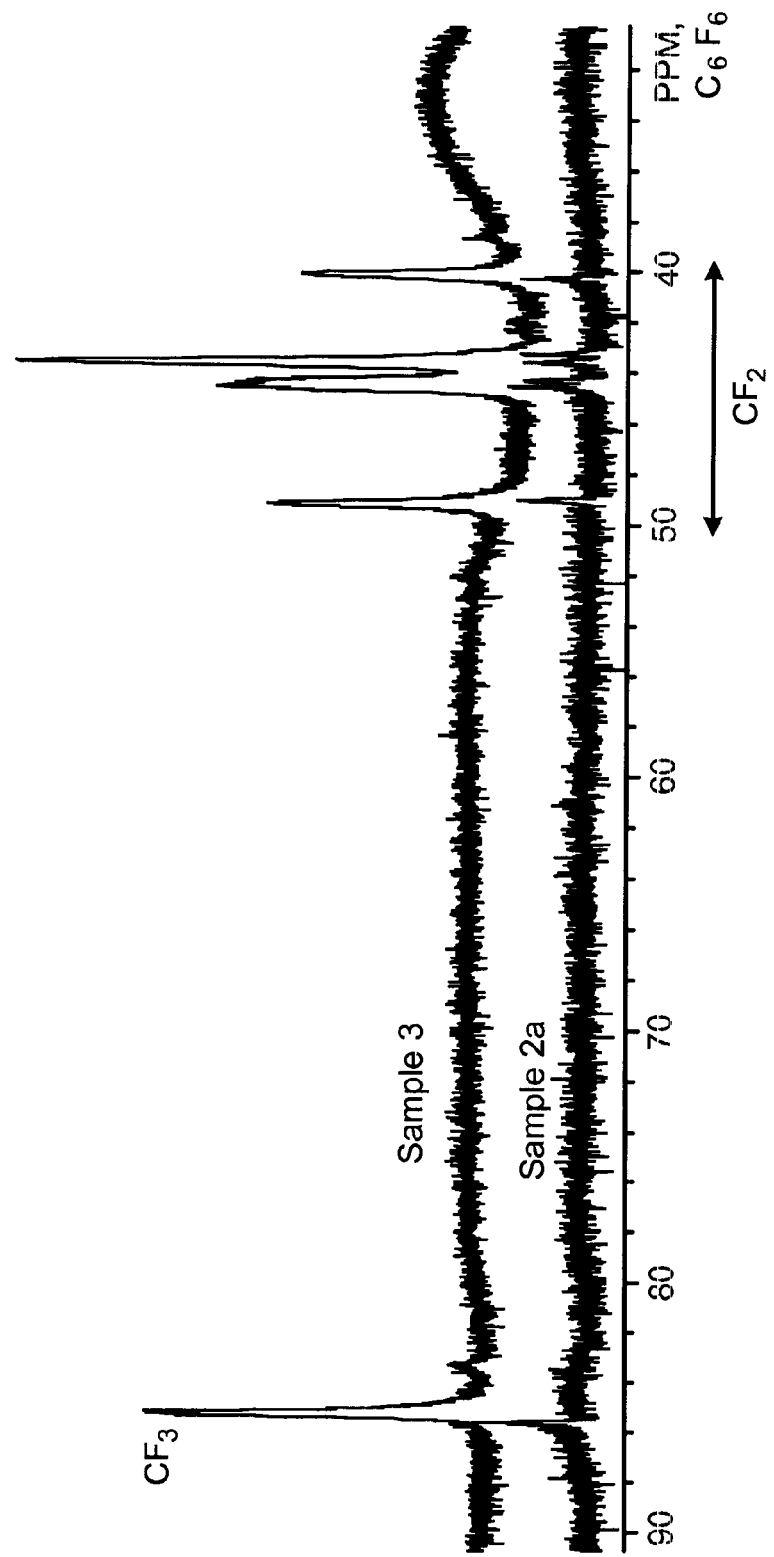

FIG. 3C shows the $^{19}$F Spectra from perflurocarbon encapsulated by 1,1, 2,2-tetrahydro perfluorodecanol (referred to herein as base polymer), as an example of data obtained with one embodiment of an amphiphillic copolymer of this invention. A Bruker/Magnex 600 MHz spectrometer (Martinos Center), with microimaging probe (not spinning) was used. Sample 2a was that of a failed covalent synthesis while sample 3 represents encapsulated 20% (w/w) 1,1, 2,2-tetrahydro perfluorodecanol, with $^{19}$F=15% (w/w) and [19F] in solution=17.3 mg polymer/mL water=140 mM

Example 4

Biological Characterization of Nanospheres

Attachment of Fluorescent Probe

Rhodamine B was converted to its acid chloride using oxalyl chloride. Treatment of the polymer (substituted with a decane chain as the hydrophobic group) with this acid chloride and base gave a reaction to form an ester linkage with the $CH_2OH$ groups at the ends of the polymer chains, binding it covalently to the polymer. This attachment did not interfere with nanosphere formation as shown by light scattering. Cy5.5 and the targeting peptide attachment may be accomplished as well, as described hereinbelow.

Size Measurement of Nanoparticles

Multi-angle dynamic light scattering (MADLS) (in addition to 90° DLS) was conducted, together with cryo transmission electron microscopy (cryo-TEM) measurements to characterize the size of the probes. Two types of formulations, as shown in Table 1, were conducted. Formulation (1) is the base polymer producing unmodified nanoparticles. Formulation (2) is the fluorine-loaded nanoparticles containing 43% (w/w) fluorine.

TABLE 1

Polymer Components for MADLS and cryo-TEM

| Formulation | Main Chain | Linker | Side Chain | Side Chain-Linker Linkage | Cargo | Cargo:Polymer by weight |
|---|---|---|---|---|---|---|
| (1) | PEG-600 | Isophthalate | Decane | Ether | None | NA |
| (2) | PEG-600 | Isophthalate | Perflurocdane | Ester | 1H,1H,2H,2H-Perfluorododecanol | 1:4 |

This proof of concept confirmed that fluorine-containing polymers can be produced, and that they form nanospheres.

Other syntheses attaching fluorine groups are possible. The amphiphilic copolymers with perfluorocarbon side chains were used to further encapsulate 1,1,2,2,-tetrahydro perfluorododecanol (20% w/w) (Schmatized also in FIG. 3B) using the same procedure. The amount of perfluorocarbon cargo encapsulated by the fluorinated polymer was determined by integration of fluorine NMR spectra. The entire particle contained 42% (w/w) fluorine, corresponding to almost 6,000 $^{19}$F atoms per nanoparticle. We anticipate that we can increase the loading by at least a factor of two to 12,000 $^{19}$F atoms per nanoparticle. By assuming a cell volume of $10^3$ μm$^3$, we estimate that uptake of $10^5$, $10^6$, $10^7$ or $10^8$ of these nanopar- Dynamic light scattering data were collected using a BI-200SM Brookhaven laser light scattering instrument (equipped with a Brookhaven BI 9000 AT digital correlator) at seven different angles (45°, 60°, 75°, 90°, 105°, 120°, and 135°) with multiple runs at each angle per sample (3~6 runs). Both samples were measured at 25° C. at a concentration of 2.0 mg/mL. The autocorrelation function and the sampling time produced by the BI 9000 AT digital correlator were used to fit into an exponential decay function so that the characteristic decay time (Γ) was obtained for each run at each angle per sample (Brookhaven Website. http://www.bic.comI/DLSBasics.html, 2005). Then the characteristic decay times at each angle were averaged, and the average decay times were plotted as a function of the square of the scattering vector q, where $q=[4\pi n \sin(\theta/2)]/\lambda$, n =the refractive index of the solution, $\theta$=scattering angle, $\lambda$=the laser wavelength. The slope of the $\Gamma$-q2 plot (R2>0.97) gave the diffusion coefficient (D) of the particles in the solution, and the hydrodynamic particle diameter d was evaluated from Stokes' equation $D=kBT/(3\pi\eta d)$, where is kB=Boltzmann constant, T=temperature in Kelvin, and $\eta$=liquid viscosity. By this method (Cipelletti, L. and Weitz, D. A. Review of Scientific Instruments, 70: 3214-3221, 1999. Kirsch, S., et al. Journal of Chemical Physics, 104: 1758-1761, 1996), the particle diameter of formulation (1) was 10.2±1.0 nm, of formulation (2) was 34.3±1.4 nm.

Figure 4A:
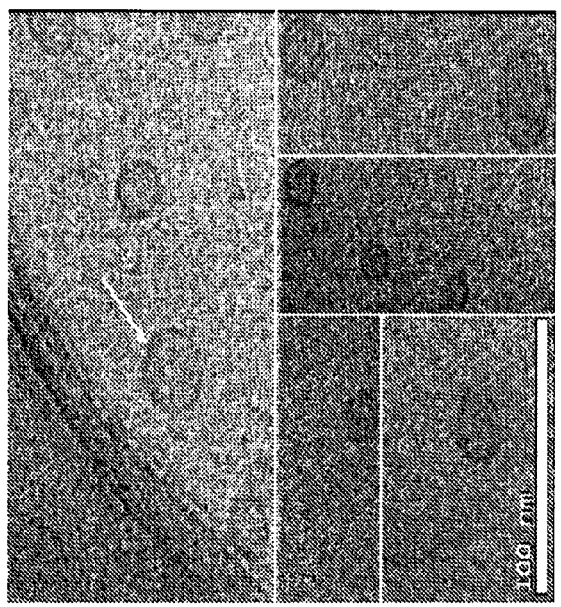
FIG. 4 shows cellular uptake of the particles. Cryo transmission electron microscopy (FIG. 4A) and confocal microscopy (FIGS. 4D and 4E) were used to qualitatively evaluate cellular uptake. Cellular uptake was also evaluated quantitatively (FIGS. 4B, 4C and 4F). INS-1 cells were incubated at 37° C., with the compound (1 mg/mL), and the uptake was measured.
Figure 4B:
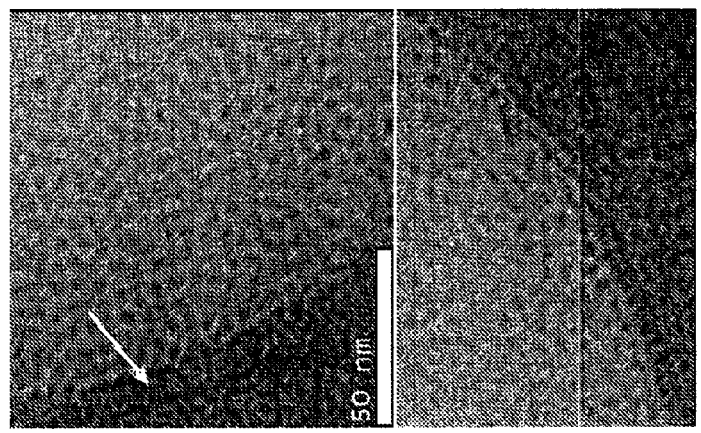
Figure 4C:
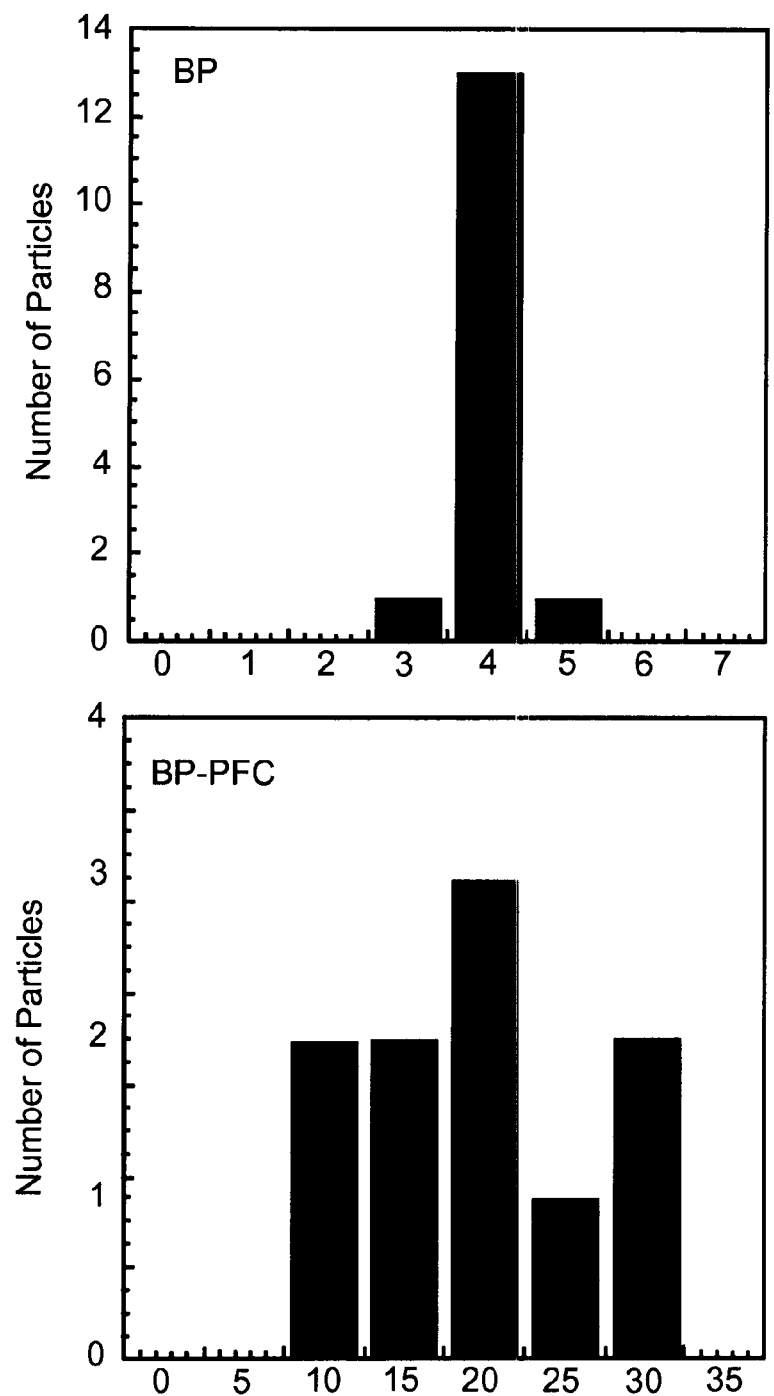

Cryo-transmission electron microscopy (TEM) images were collected by a JEOL JEM-2200FS Field Emission Electron Microscope. A 2.5 μL aliquot of sample solution was dropped on a holey carbon film coated copper-carbon grid using a micro pipette. The grid was then blotted with filter paper for five seconds and immediately dipped into liquid ethane. Then the grid was transferred into the electron microscope for image collection using liquid nitrogen to maintain the temperature. Examples of images are shown in FIGS. 4 for formulation 1 (A) at a concentration of 44.5 mg/mL and formulation 2 (B) at 48.5 mg/mL, respectively. The nanoparticles accumulate at the interface of the ice and the carbon substrate. The fine-grained light gray background is the amorphous ice crystal. The dark gray background is the carbon substrate. FIG. 4B shows values obtained for the base polymer alone, and that with encapsulated fluorocarbon.

Uptake of Fluorescently Labeled Nanoparticles

Figure 4D:
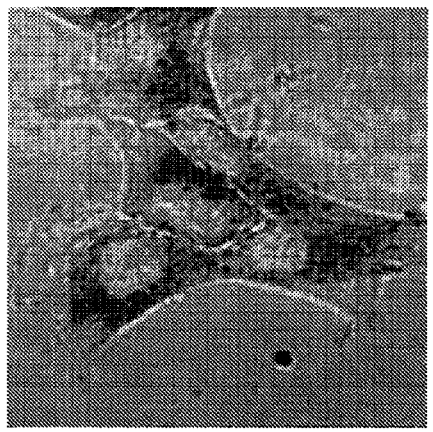
Figure 4E:
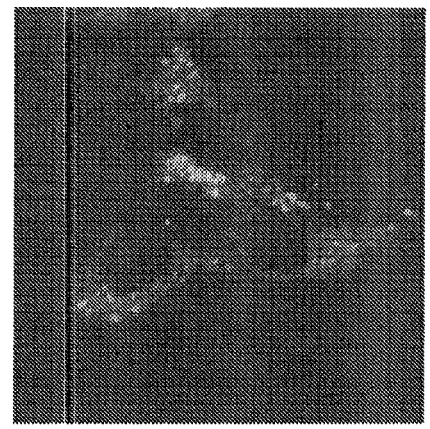
Figure 4F:
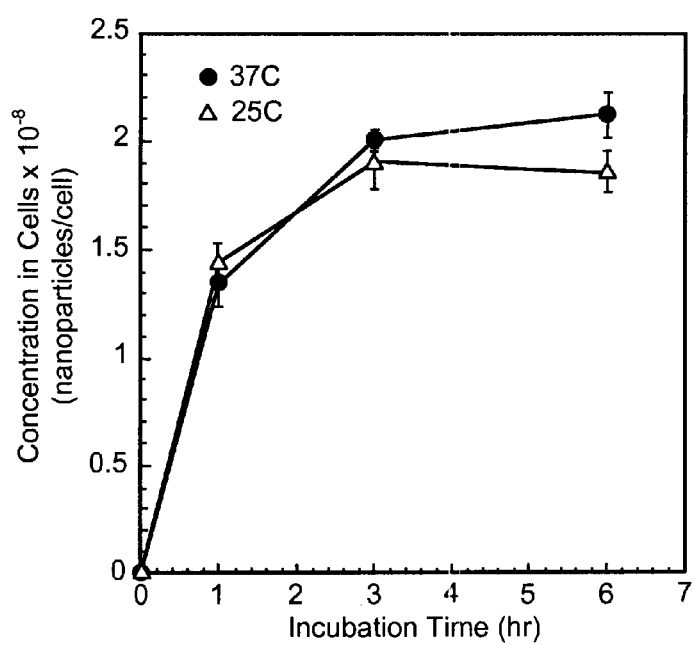

To demonstrate the ability of the nanoparticles to carry a cargo into cells, INS-1 cells were incubated in vitro with labeled nanospheres, containing Rhodamine B chemically attached to the amphiphilic copolymer at the free ends of the PEG chains, at 37° C. for 35 minutes, washed, and fixed. The cells were then examined with a Zeiss LSM 510 Meta high resolution laser scanning confocal microscope equipped with a 100× oil emersion objective lens. Data was gathered using both the appropriate laser for imaging Rhodamine B and transmitted light for imaging the cells, and the images were merged into one picture (FIGS. 4D and 4E). Staining may represent localization of the polymer/nanoparticles within endosomes of the cell. Uptake was quantitated and is presented graphically in FIG. 4C and 4F. INS-1 cells were incubated at 37° C., with the compound (1 mg/mL), and the uptake was found to be temperature-independent, with a maximum non-selective uptake of $2\times10^8$ nanoparticles/cell seen.

Drug Delivery with Nanoparticles

In order to determine the capability of the nanospheres to carry drug cargo into a cell, in vivo studies were conducted which demonstrated the efficacy of encapsulated non-steroidal anti-inflammatory drugs such as aspirin and naproxen (Kurnar, R., et al. Journal of the American Chemical Society, 126: 10640-10644, 2004), in a transdermal application, indicating that the nanospheres were able to carry cargo through the skin.

Acute Systemic Toxicity

Acute oral toxicity testing of intact nanospheres and individual components was carried out to determine the LD50 (median lethal dose) with C57Bl/6 (Table 2). For all but one case, the LD50 was far above 2 g/Kg, the limit for essentially non-toxic substances (Botham, P. A. Toxicology in Vitro, 18: 227-230, 2004; NIH Guidance Document on Using In Vitro Data to Estimate In Vivo Starting Doses for Acute Systemic Toxicity, NIH Publ 01-4500. pp. 48. Research Triangle Park, N.C., USA: NIEHS, 2001). Even the most toxic nanospheres in this study, (isophthalate linker, ether linkage), gave an LD50 of 1 g/Kg, which is higher than that for many food additives on the list of those generally regarded as safe (GRAS) (NIH Guidance Document, supra; EAFUS: A Food Additive Database. FDA/Center for Food Safety & Applied Nutrition, 2004).

TABLE 2

Acute oral toxicity tests

| Hydrophilic Group | Linker | Linkage Bond | Side Chain | LD50 (g/Kg) |
|---|---|---|---|---|
| PEG 600 | | | | 38 |
| | Aspartic Acid | | | 20 |
| PEG 600 | Aspartic Acid | Amide | Nonyl | 60 |
| PEG 600 | Isophthalate | Ester | Decane | 60 |
| PEG 600 | Isophthalate | Ether | Nonyl | 1 |

Figure 5:
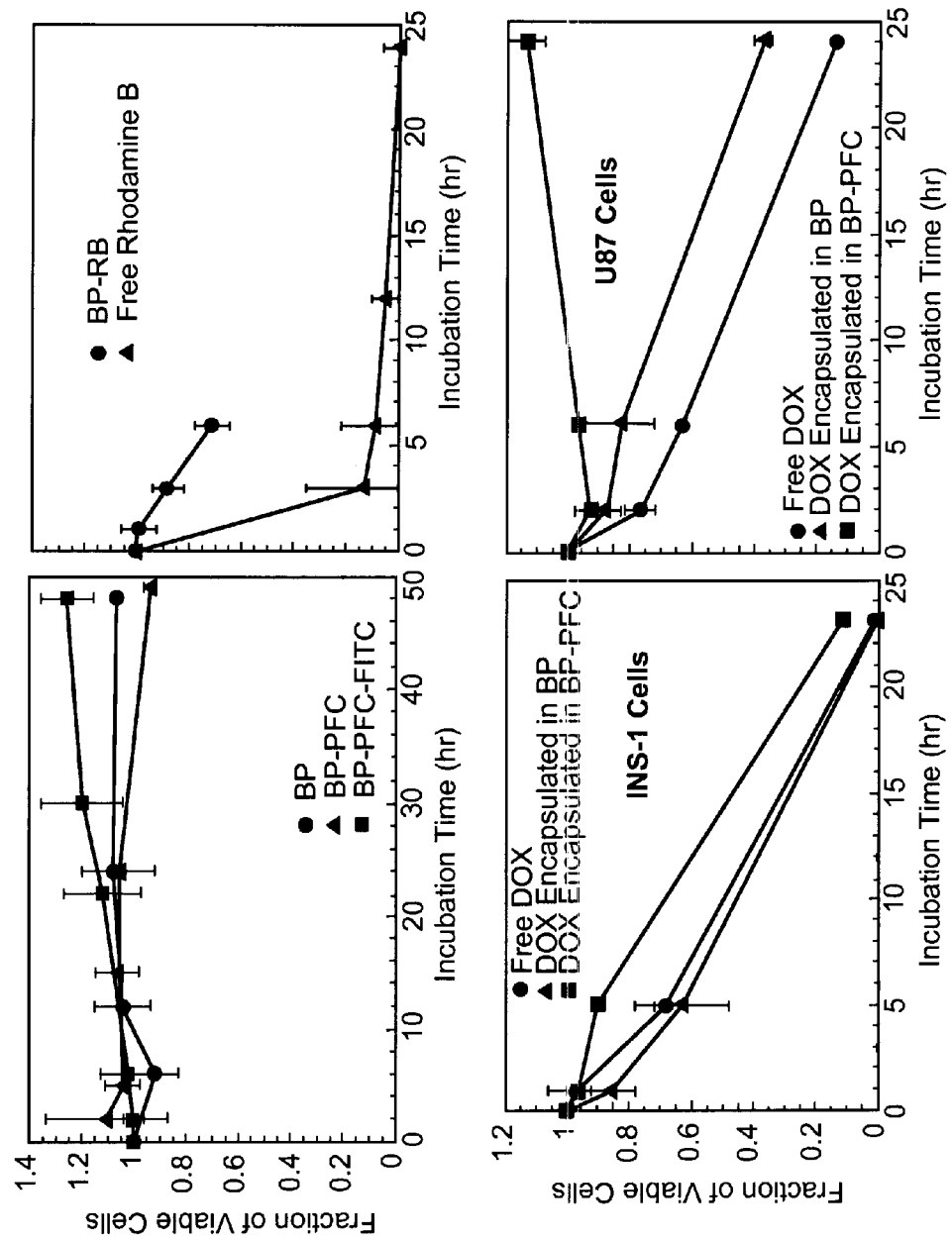
FIG. 5 shows cellular cytotoxicity, following exposure of the cells to some polymers of the invention.

Cellular cytotoxicity following exposure to the polymers and reagents: INS-1 cells were incubated with the polymers and/or reagents (1 mg/mL polymer or 0.05 mg/mL dye) at 37° C., and cellular viability was determined by MTS (FIG. 5). Base polymer or encapsulated rhodamine exposure did not induce any observable cytotoxicity, up to 48 hours post-exposure, though cytotoxic effects were readily observed even 3 hours following exposure to Rhodamine alone.

INS cells incubated with 0.2 mg/mL free or encapsulated doxorubicin at 37° C., showed a comparable rate of cell death, with the death rate decreasing with the presence of PFC side chains, as measured by MTS. Encapsulation of doxorubicin resulted in reduced cytotoxicity in U87 cells, with BP, but not PFC side chains.

Figure 6A:
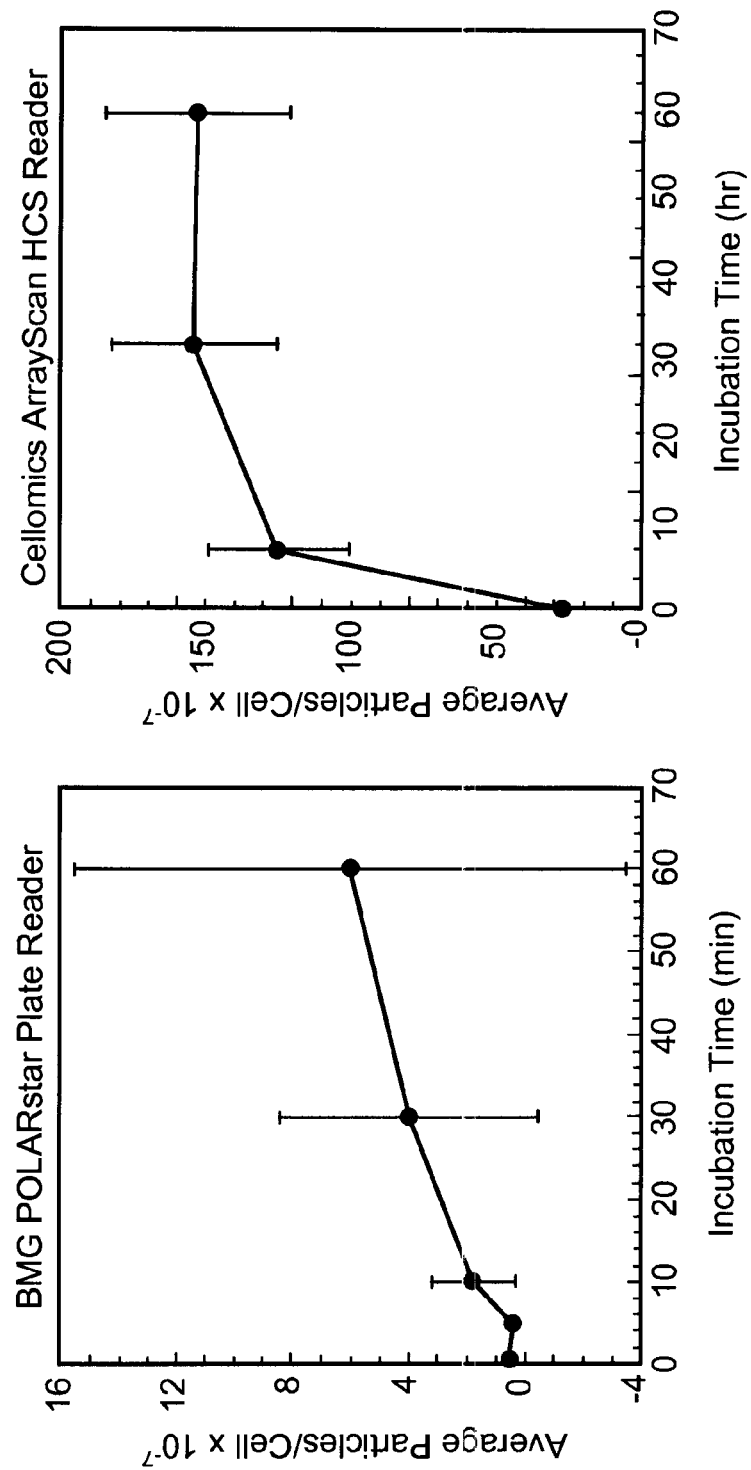
FIG. 6 describes the kinetics of cellular uptake and intracellular localization of some polymers of the invention.
Figure 6B:
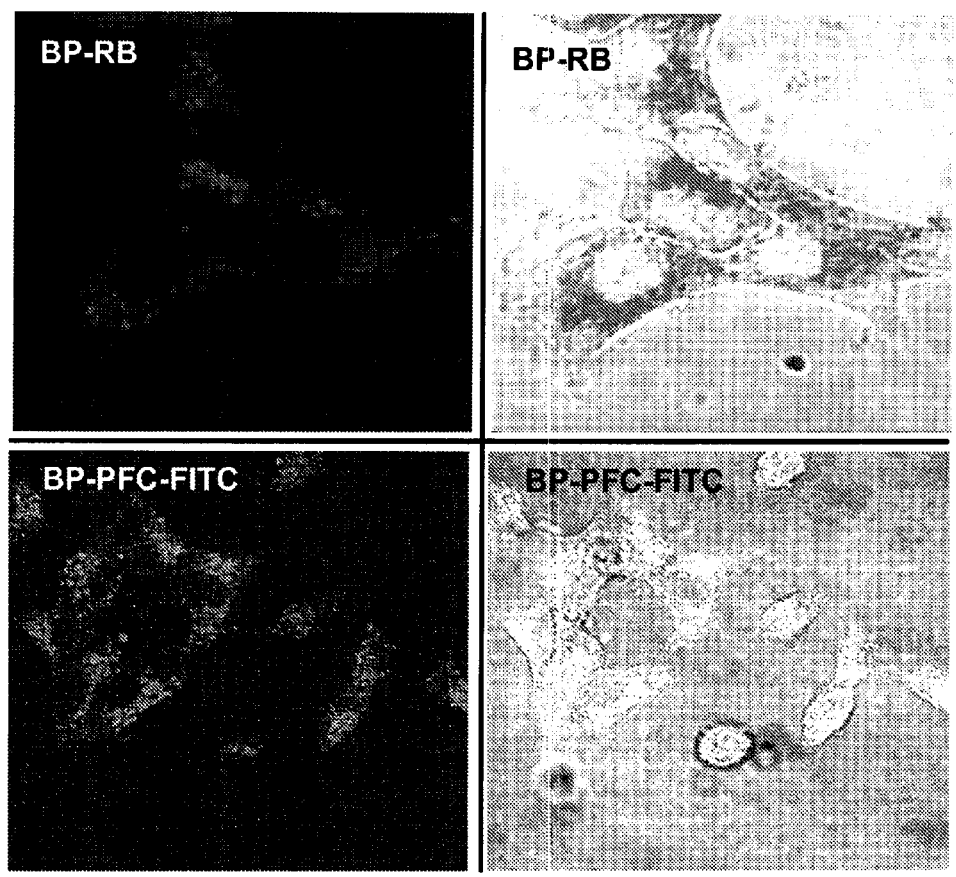

The kinetics and sensitivity of detection of cellular uptake were evaluated as well (FIG. 6). INS-1 cells were incubated with I mg/mL polymer at 37° C. and evaluated by the indicated reader. The sensitivity of the plate reader was low as the background created too much noise. Data obtained using Cellomics ArrayScan was less sensitive to background noise and allowed for quantification of cellular uptake, which increased rapidly, then levelled out after 4 hours (FIG. 6A). Confocal microscopic evaluation of INS-1 cells incubated with 0.2 mg/mL BP-RB for 30 min or I mg/mL BP-PFC-FITC for 14 hr, washed 3× (2 min), and fixed (20 min) (FIG. 6B), showed that the fluorescent polymer was essentially confined to cytoplasmic vesicles and not the nucleus.

Figure 6C:
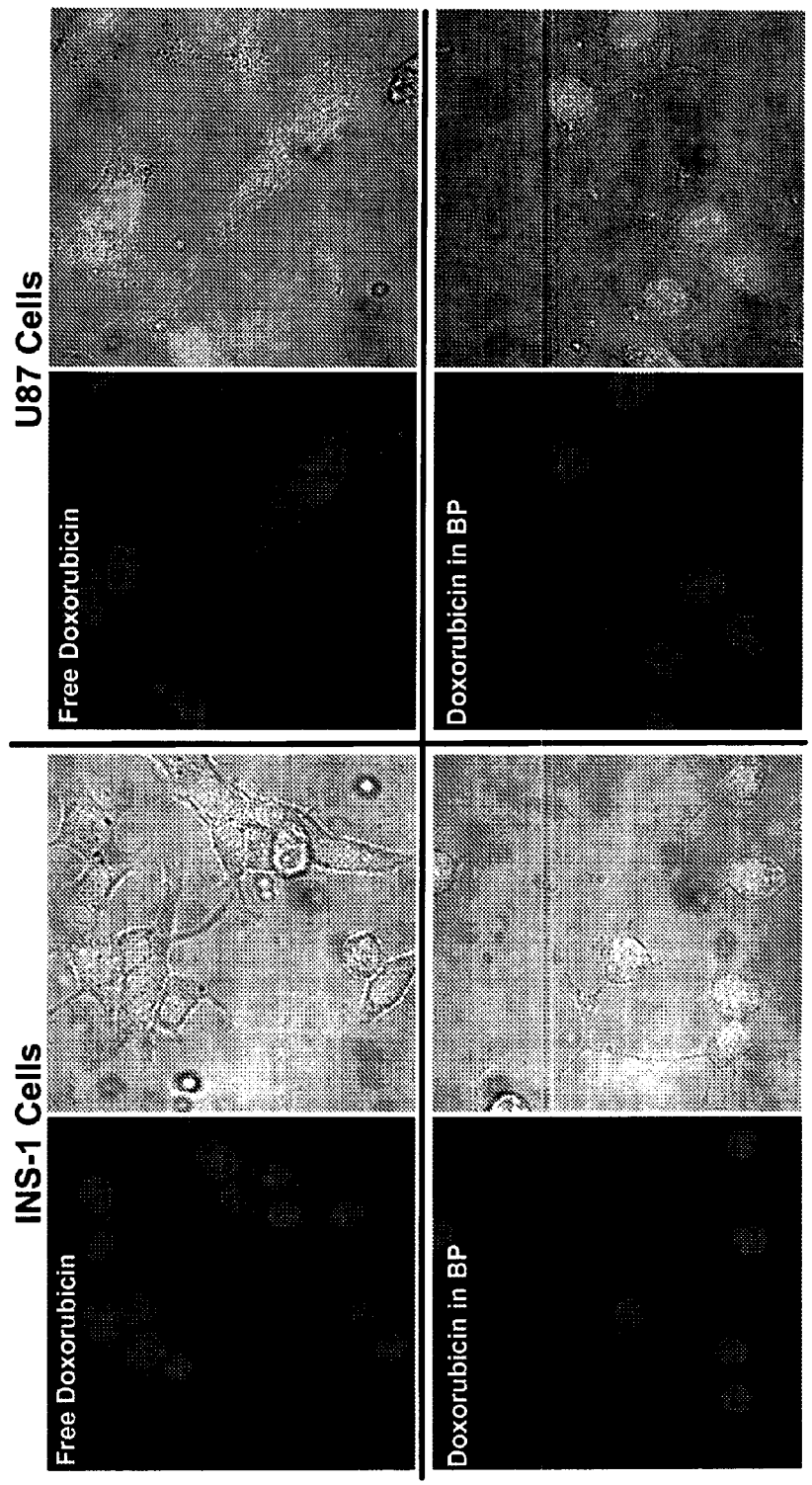

Uptake of free and encapsulated Doxorubicin was evaluated by confocal microscopy as well (FIG. 6C). Cells were incubated with 0.2 mg/mL free or encapsulated doxorubicin for 5 hr at 37° C., washed 3× (2 min), and fixed (20 min). Doxorubicin was largely confined to the nucleus. Therefore, doxorubicin must be released from the polymer, since the polymer is too large to enter the nucleus.

Example 5

Targeting of uMUC-1 Antigen with a Multi-modal Imaging Probe

Nanoparticles are more easily taken up by a tumor as compared to normal tissue, because of the generally greater vascularization and interstitial volume of a tumor. However, in order to determine whether it is possible to greatly enhance selectivity, a ligand may be coupled to the free ends (16-24 per micelle) of the PEG-linker segments and, in another embodiment, to functional groups introduced into the PEG chains.

The ligand initially chosen was a 15-amino acid synthetic peptide designated EPPT1 that is derived from the binding site of a monoclonal antibody raised against human epithelial cancer cells displaying the underglycosylated mucin-1 antigen (uMUC-1). MUC-1 is a transmembrane molecule expressed over the cell surface and in internal compartments by most glandular epithelial cells. It is overexpressed on almost all human epithelial cell adenocarcinomas as well as some nonepithelial and hematological malignancies (altogether accounting for more than 70% of all newly diagnosed cancer cases) in an underglycosylated form, which exposes an immunogenic epitope that is normally masked. The synthetic peptide EPPT1 has a reasonably high binding constant ($K_d$=20 µM), and nanoparticles bound to the epitope would either remain bound to the cell surface or be internalized by receptor-mediated endocytosis. In this way, selectivity is determined primarily by the specific ligand-receptor interaction rather than by the ease of perfusion through the tumor.

A multi-modal imaging probe targeting uMUC-1 tumor antigen was synthesized and tested both in vitro and in vivo (Moore, A., et al. Cancer Research, 64: 1821-1827, 2004). The probe consisted of cross-linked iron oxide as an MR-imaging contrast agent that carried Cy5.5 dye as a NIRF optical probe and EPPT1 peptides produced by solid-phase synthesis, both attached to amino groups linked to the CLIO dextran coat. A FITC label was added to the $NH_2$ terminus of the peptide for subsequent fluorescence microscopy analysis, and the probe was radioiodinated by attachment to the peptide tyrosines by the Iodogen method for cell binding analysis and biodistribution studies (FIG. 7).

A terpolymer (FIG. 7, Series 1) was obtained via enzymatic polymerization using novozyme-435, 5-amino dimethylphthalate, 5-hydroxy dimethylphthalate and polyethylene glycol. FITC and Cy5.5 were attached to the polymer by stirring separately in dimethylformamide for four hours at room temperature with the terpolymer. The resultant polymer was dialysed and used for partial o-alkylation using alpha bromo acetyl triethyleneglycol in $K_2CO_3$ and acetonitrile on refluxing them together. The free hydroxyl group at the end of the triethyleneglycol unit of the partially alkylated polymer was activated by stirring disuccinimidyl carbonate in acetonitrile with DMAP and used for peptide attachment. The activated hydroxyl polymer was stirred with peptide in phosphate buffer (pH-7.2) for 12 hours to obtain the desired polymer. A hydrocarbon chain was then introduced by stirring the halogenated hydrocarbon chain with polymer in triethyl amine to make the carrier molecule suitable for micelle formation.

To attach FITC to the Terpolymer, FITC was added to a three necked round bottom flask containing terpolymer dissolved in anhydrous DMF under the environment of nitrogen. The resulting mixture was stirred at room temperature for four hours, after which DMF was washed out using an excess of hexane. The remaining residue was dried under vacuum. Residue was then subjected to dialysis (6000-8000 Mw dialysis bag) to remove unreacted FITC in the product. The resultant product was characterized from its $^1$HNMR and UV spectra.

To attach Cy5.5 to the Terpolymer, Cy5.5 was added to a three necked round bottom flask containing terpolymer dissolved in anhydrous DMF under the environment of nitrogen. The resulting mixture was stirred at room temperature for four hours. After the completion of the reaction DMF was removed by washing several times with an excess of hexane. The residue was further dried under vacuum. Residue was then subjected to dialysis (6000-8000Mw) to get rid of unreacted Cy5.5 in the obtained product. The resultant product was characterized from its $^1$HNMR and UV spectra.

For the esterification of free hydroxyl on the terpolymer, nonanoyl chloride dissolved in dichloromethane was added dropwise in reaction mixture containing dye-attached terpolymer and triethylamine, under nitrogen with constant stirring at room temperature. The resulting mixture was stirred for six hours. After completion of the reaction, solvent was removed under vacuum and THF was added and then filtered to remove salt formed in the reaction. Unreacted nananoyl chloride was removed by washing with hexane. Obtained product was dried under vacuum and was characterized on the basis of its $^1$HNMR and UV spectrum. A similar method was used for polymers with FITC and polymers with Cy5.5.

For O-alkylation, the polymer was dissolved in anhydrous acetonitrile and added to three neck round bottom flask under nitrogen with constant stirring containing fused $K_2CO_3$, followed by dropwise addition of bromoester of TEG dissolved in acetonitrile. The resulting mixture was refluxed for eight hours. After completion of the reaction $K_2CO_3$ was filtered off and filtrate obtained was concentrated under vacuum to get the desired product.

For activation of the free hydroxyl group, disuccinimidyl carbonate and the polymer dissolved in acetonitrile in the presence of DMAP were stirred in a nitrogen environment, and the resulting mixture was stirred for 12 hours. Solvent was then removed under vacuum at room temperature. Separated salts and N-hydroxyl succinamides were removed by repeated precipitation with diethyl ether in acetonitrile. The thus obtained pure compound was vacuum dried, characterized, and used for peptide attachment.

For peptide attachment, an activated hydroxyl polymer was stirred with peptide in phosphate buffer (pH-7.2) for 12 hours to get the desired peptide attached polymer. The product was characterized by NMR, IR and UV spectroscopy. After the peptide was attached, the hydrocarbon chain was attached in order to make the polymer suitable for micelle formation. This was achieved by stirring the halogenated hydrocarbon chain with polymer in triethylamine.

To extend these studies using perfluoro labeled polymer, the same FITC-labeled EPPT1 peptide was used. The crosslinked iron oxide (CLIO)-EPPT probes had a hydrodynamic diameter measured by dynamic light scattering of about 36 nm, slightly smaller than fluorine-containing micelle nanoparticles, and contained 14 peptides and 5 Cy5.5 molecules per particle, comparable to what is anticipated with the micelles. The study with the CLIO-EPPT nanoparticles established test procedures which will be used.

EPPT1 peptides were attached to the free PEG terminal hydroxyls using carbodiimide chemistry: a stoichiometric excess of N-hydroxysuccinimide and carbodiimide are added to the micelles in water, reacted for 15~30 minutes at room temperature, and purified by dialysis. The EPPT1 peptides were added to the modified polymer and reacted overnight at room temperature. The reaction occurs between —OH on the PEG unit and the N terminus (—$NH_2$) on the peptide. Purification of the probe is accomplished by dialysis or column separation.

Cell binding assays (FIG. 7D) were carried out with a variety of human uMUC-1-positive tumor cell lines: ZR-75-1 (breast), BT-20 (breast), HT29 (colon), CAPAN-2 (pancreas), LS174T (colon), and ChaGo-K-1 (lung) as well as human control uMUC-1-negative tumor and normal cell lines. Cell lines were incubated with varying amount of $^{125}$I-labeled CLIO-EPPT for 1 hour. uMUC-1-negative and normal cell lines had much lower nanoparticle uptake than that of the uMUC-1-positive tumor cell lines, which bound on the order of $10^7$-$10^8$ CLIO-EPPT nanoparticles per cell.

The same lines and protocols will be used for determining fluorine-loaded micelle nanoparticle uptake, with 10-1000 or higher mM fluorine concentration uptake in the uMUC-1-positive cells being the concentration sought. Similar binding assays will be conducted, and binding as a function of both concentration and time will be determined, in order to explore conditions that provide maximum selectivity between uMUC-1-positive tumors and normal cells.

Figure 7A:
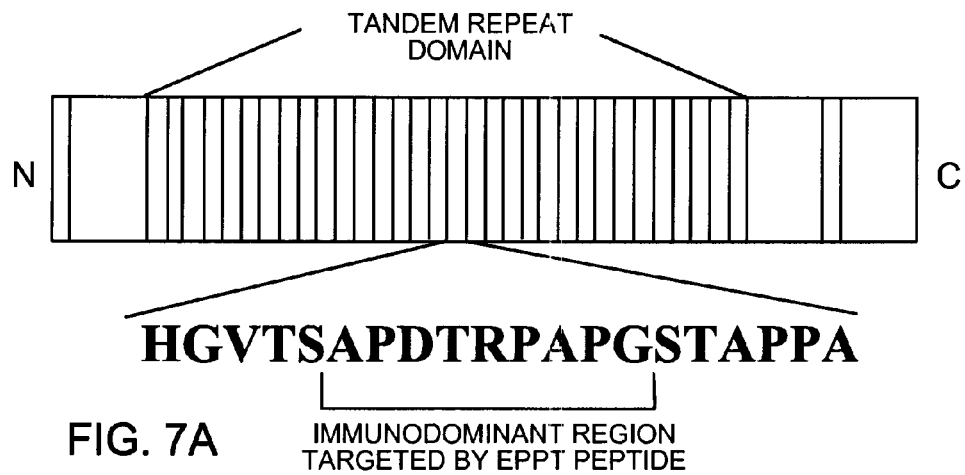
FIG. 7 depicts a crosslinked iron oxide (CLIO)-EPPT multi-modal imaging probe. (A) The core protein of the MUC-1 tumor antigen. The immunodominant region of the tandem repeat is recognized by the EPPT1 peptide derived from an ASM2 monoclonal antibody (45). (B) Synthesis (left) and scheme of the probe (right). (C) The absorption spectrum of CLIO-EPPT showed the presence of three peaks corresponding to FITC, Cy5.5, and iron oxide nanoparticles. (D) Cell binding assay: cells expressing underglycosylated mucin-1 accumulate significantly more CLIO-EPPT (P<0.05) than uMUC-1-negative tumor or normal cells. (E) Fluorescence-activated cell sorting analysis of the set of underglycosylated mucin-1 antigen (uMUC-1)-positive tumor cell lines (BT-20, CAPAN-2, ChaGo-K-1, HT-29, LS174T) showed a shift in fluorescence in the FL1 and FL4 channels and no shift in the control uMUC-1-negative cell line U87. Fluorescence microscopy showed colocalization of the FITC and Cy5.5 signal within the set of the same cell lines after incubation with the CLIO-EPPT probe. Left, overlay of the bright field and FITC channel; middle, overlay of the bright field and Cy5.5 channel; right, overlay of the FITC and Cy5.5 channels. Note that no fluorescence was observed in FITC or Cy5.5 channels in the U87 cell line. Magnification bars=10 μm.
Figure 7B:
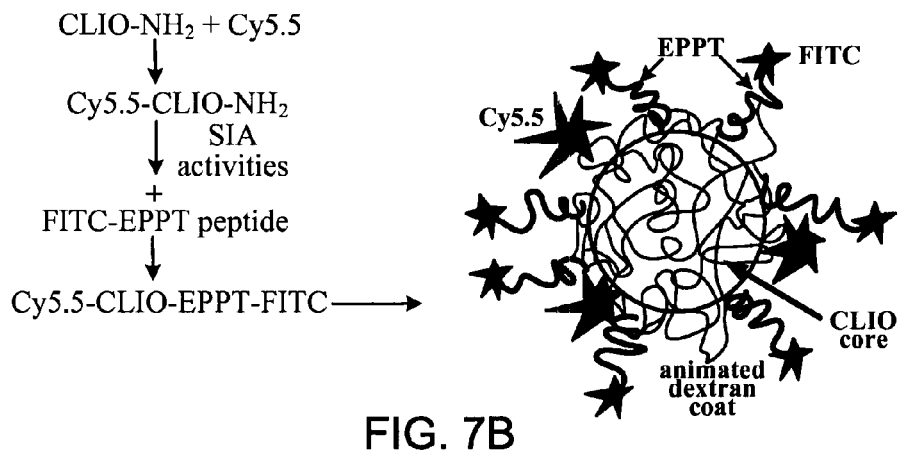
Figure 7C:
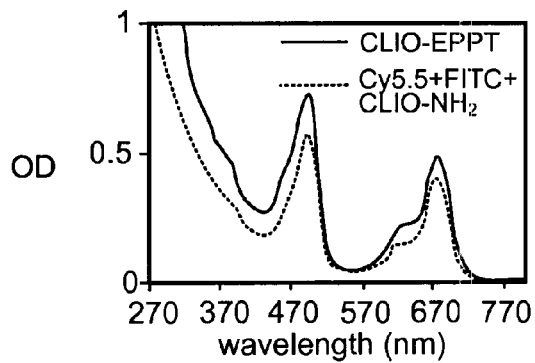
Figure 7D:
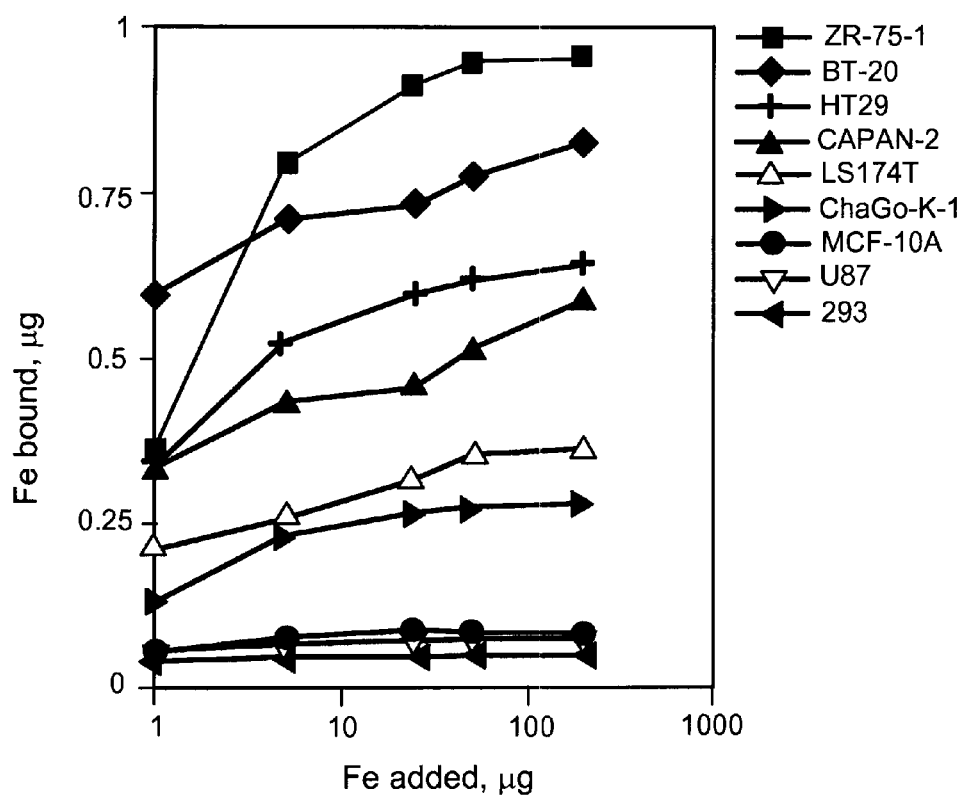
Figure 7E:
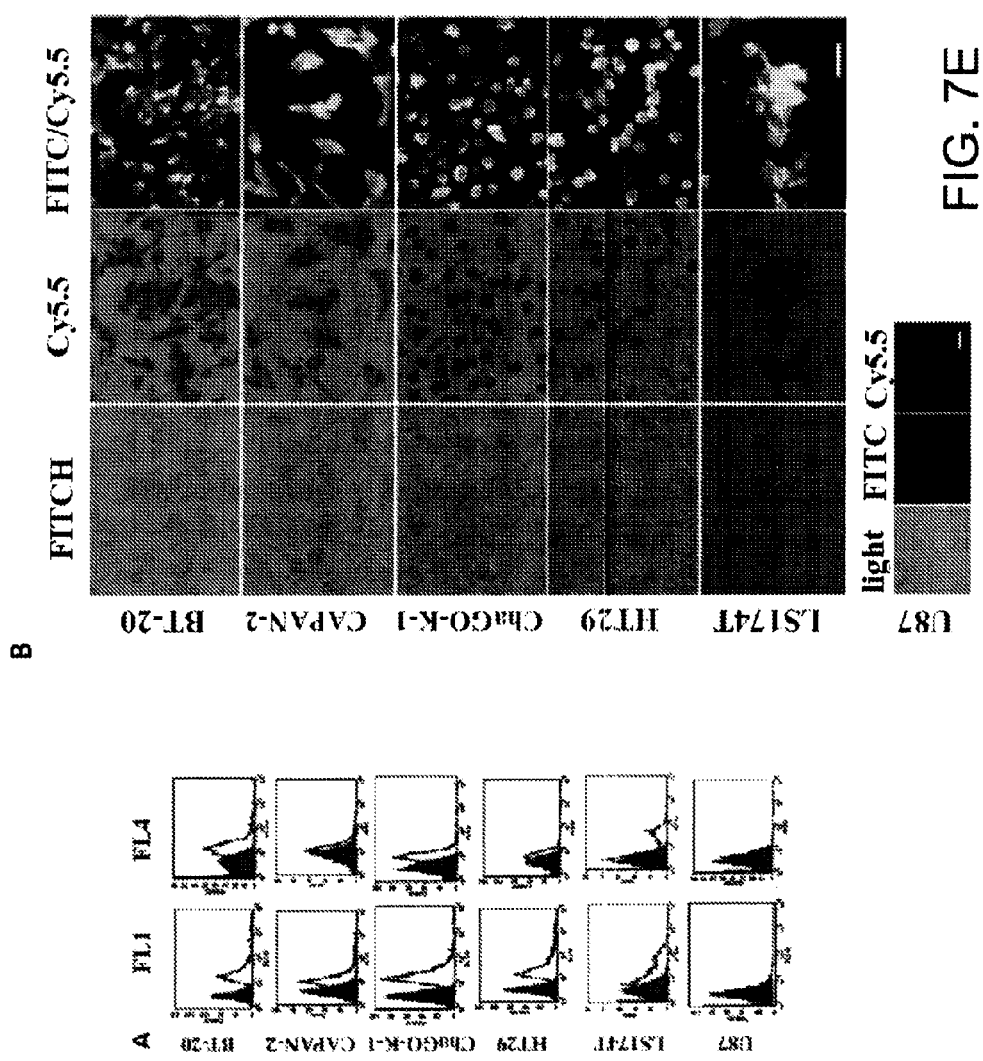

In vitro specificity of CLIO-EPPT for adenocarcinomas was further characterized by flow cytometric analysis of probe binding to selected adenocarcinoma and control cell lines (FIG. 7E). A control cell line showed no cell binding, whereas adenocarcinoma cell lines bound the probe and displayed diverse staining intensities, consistent with variable glycosylation. Fluorescence microscopy experiments, in which adenocarcinoma and control cells were incubated with the probe, confirmed the fluorescence-activated cell sorting data. All of the adenocarcinoma cell lines stained strongly and showed colocalization of the FITC and Cy5.5 signals.

Figure 8A:
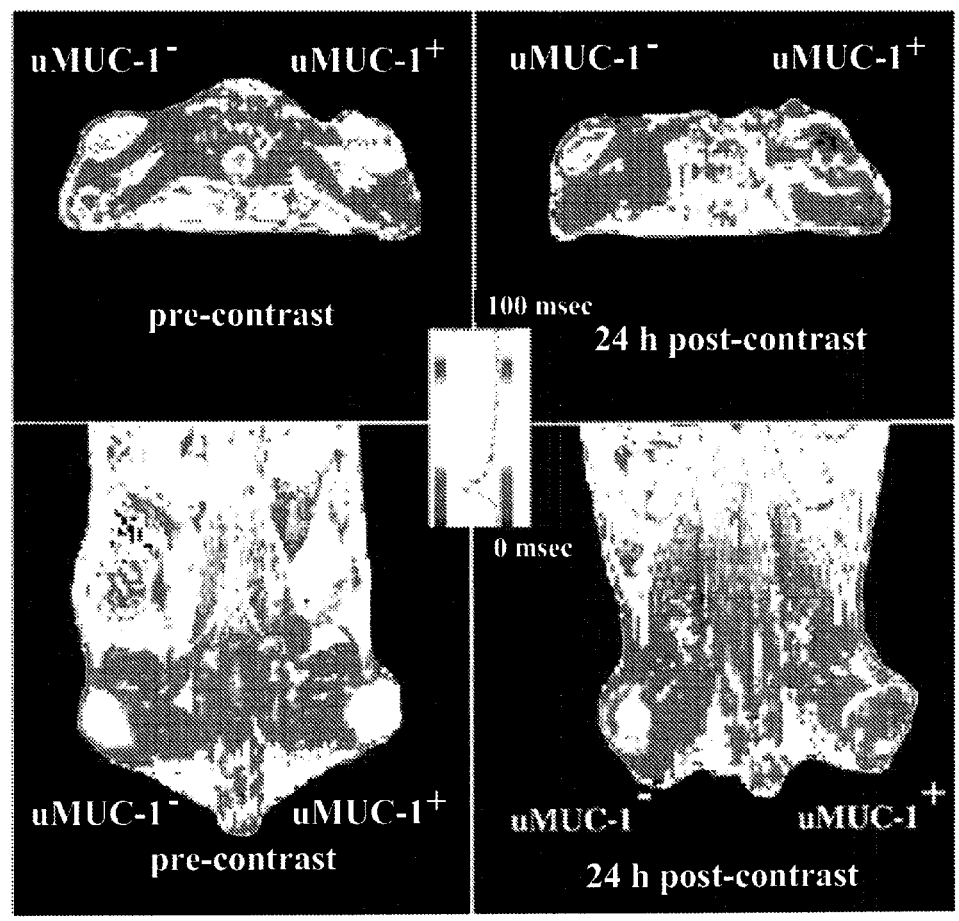
FIG. 8 demonstrates results of imaging of the animals bearing underglycosylated mucin-1 antigen (uMUC-1)-negative (U87) and uMUC-1-positive (LS174T) tumors. (A) Transverse (top) and coronal (bottom) images showed a significant (52%; P<0.0001) decrease in signal intensity in uMUC-1-positive tumors 24 h after administration of the CLIO-EPPT probe. (B) White light (left), near-infrared fluorescent (NIRF) (middle) images, and a color-coded map (right) of mice bearing bilateral underglycosylated mucin-1 antigen uMUC-1-negative (U87) and uMUC-1-positive (LS174T) tumors. NIRF imaging was performed immediately after the MRI session. (C) White light (top) and NIRF (bottom) images of LS174T- and U87-excised tumors and muscle tissue. uMUC-1-positive LS174T tumor produced a strong NIRF signal. (D) Dual channel fluorescence microscopy of the frozen LS 174T tumor section. Green channel fluorescence from the FITC-labeled EPPT peptide (left) colocalized with Cy5.5 fluorescence derived from Cy5.5-labeled cross-linked iron oxides (middle). The combination image shows colocalization of two signals (right). Magnification bar=10 μm.

In vivo $^1$H-MR imaging was performed on animals bearing bilateral uMUC-1-positive and uMUC-1-negative tumors before and 24 hours after probe injection. No significant change in signal intensity of T2-weighted images was observed in uMUC-1-negative tumors, whereas significant signal reduction was observed in some regions of uMUC-1-positive tumors (a 52% decrease for LS174T tumors versus a 13-18% decrease in control tumors, FIG. 8A). The same animals were subjected to optical imaging immediately after the MR-imaging session. A high intensity NIRF signal was obtained from the uMUC-1-positive tumors, whereas no significant signal was observed from the control tumors (FIGS. 8B and 8C). Fluorescence microscopy of excised tumors and muscle tissue gave results consistent with NIRF images. From biodistribution studies with $^{125}$I-CLIO-EPPT, on average uMUC-1-positive tumors accumulated 3.4 times more of the probe than uMUC-1-negative tumors. Correlative dual channel fluorescence microscopy of excised tumors showed colocalization of FITC and Cy5.5 signals in uMUC-1-positive tumors but no signal in control tumors (FIG. 8D).

A multi-modal probe for MR and NIRF imaging was herein characterized and tested in vitro and in vivo in animal models of human cancer, indicating specific accumulation in uMUC-1-expressing tumors and providing in vivo imaging results.

Similarly, nanoparticles carrying perfluorocarbons will be used for $^{19}$F-MR imaging, which has some advantages over $^1$H-MR imaging. Cell-associated fluorine concentrations necessary to make use of these advantages are obtainable, and versatile imaging probes can be developed according to the methods and processes of this invention, that may be used for the detection of cancer, inter-alia, and, in other embodiments, monitoring the progression of intervention in afflicted subjects.

Example 6

Synthesis and Characterization of Multi-Modal Probes for In Vivo Cancer Imaging

Probes comprising a perfluorinated polymer with Cy5.5 attached for NIR study as well as attachment of the targeting peptide EPPT1 to the hydroxyl groups at the free ends of the PEG chains may be synthesized as described herein.

Figure 9:
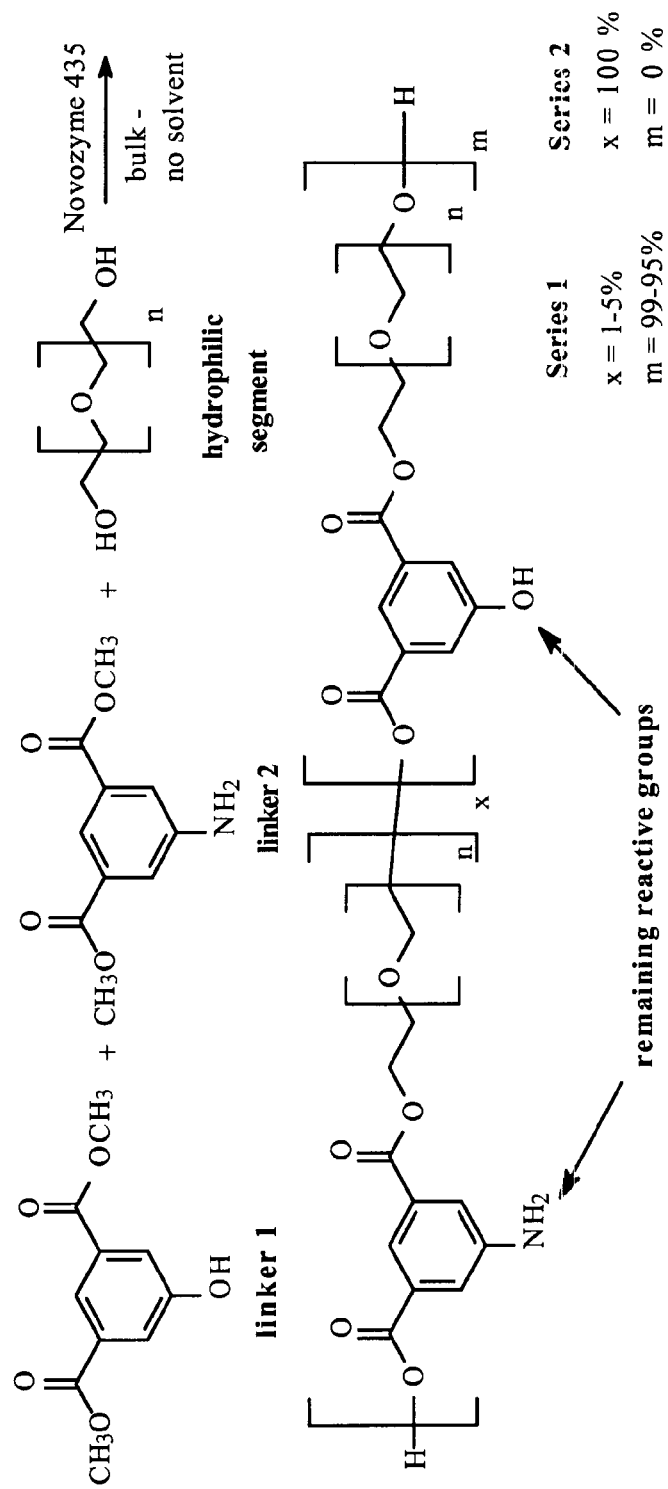
FIG. 9 schematically depicts a first stage of synthesis of the amphiphillic polymer I, accomplished via enzymatic polymerization.

Synthesis of the polymer backbone will be carried out using a well-established enzymatic method (Kumar, R., et al., Journal of Macromolecular Science, 2002, supra; Kumar, R., et al. Journal of the American Chemical Society, 2004, supra). The synthetic scheme is shown in FIG. 9. Polymerization involves two linkers with linker 2 present in small amounts (1-5%) to produce the polymer shown. The synthesis is conducted such that PEG hydroxy groups are present at the ends of the chain.

Perfluorocarbon side chains are then attached to the linker hydroxyls using standard acylation procedures to form ester linkages with the polymer backbone. Other linkers, such as, for example, ether amide, may similarly be utilized.

Figure 10:
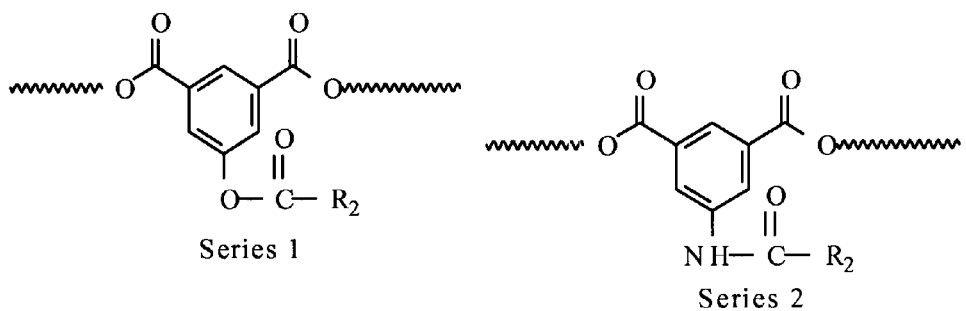
FIG. 10 depicts some embodiments of the alternations for perfluorocarbon side chains that may be synthesized or used according to this invention.

A variety of fluorine-containing polymers may be prepared via this scheme, as exemplified in FIG. 10. The synthetic schemes may be conducted using amine-modified base polymer, while the inclusion of small amounts of the amine moiety should not interfere with nanosphere formation.

In addition, chain length may be varied (from 5 to 13 carbons), and the relative number of fluorine atoms may be varied, which may alter the hydrophobicity of the side chain.

The synthesis and in vitro characterization studies described hereinabove may be used for optimization of nanoparticle formulation. The effect of synthesis parameters on loading and stability may also be studied, and a number of encapsulating materials may be investigated, including perfluorodecalin, bromo-perfluoroheptane, and perfluoro-crown ether. Cy5.5 may be attached, in order to perform NIRF determination, EPPT1 peptides may be used for targeting, and radioiodine may be incorporated for cell binding and biodistribution studies. A number of formulations may be tested to determine specificity and cellular uptake.

Synthesis of the polymer labeled with Cy5.5 dye may be conducted as described (Josephson, L., et al. Bioconjugate Chemistry, 10: 186-191, 1999), using aminated CLIO nanoparticles, or partially aminated basic polymer. The attachment of the Cy5.5 monofunctional dye to amine groups of the base polymer is performed by adding 100 mg of polymer in 0.5 M sodium bicarbonate with the pH adjusted to 9.6 to 1 mg of Cy5.5 dye (Amersham-Pharmacia, Cat.#Q15408). The mixture is incubated on a rotator overnight at room temperature. After incubation, the mixture is purified from non-reacted dye on a G-25 Sephadex column equilibrated with 20 mM sodium citrate buffer with 0.15 M NaCl, pH 8.0. Incubation times are varied to achieve different polymer:Cy5.5 ratios.

The EPPT1 peptide, YCAREPPTRTFAYWG (SEQ ID NO: 1) may be modified to introduce a FITC label for subsequent fluorescence microscopy/FACS analysis. The FITC label will be introduced by adding FITC-labeled Lys on the C-terminus followed by a second unlabeled lysine to serve as an attachment point. The Cys thiol group will be protected with an acetoxy methyl group. The final peptide will have the following sequence: Y-C(ACM)-A-R-E-P-P-T-R-T-F-A-Y-W-G-K(FITC)K (SEQ ID NO: 2) (Italic font indicates the original sequence). The peptide is synthesized on an automatic synthesizer (PS3, Rainin, Woburn, Mass.) using Fmoc chemistry with HBTU and HOBT. Peptides are cleaved from the Rink amide HBHA resin (Novabiochem, San Diego, Calif.) with 5 ml of TFA/thioanisole/ethanedithiol/anisole (90/5/3/2) and purified by C18 reverse phase HPLC. Molecular weight is determined by MALDI mass spectroscopy.

The synthesis of Cy5.5-EPPT1 nanoparticles is accomplished via the attachment of the FITC-labeled peptides to the Cy5.5-modified basic polymer, via the procedure of Zalipsky, et. al. (Zalipsky, S., et al. Biotechnology and Applied Biochemistry, 15: 100-114, 1992), which attaches proteins through succinimidyl activation of the PEG hydroxy group to react with the N-terminus of the peptide, in this case, the added lysine group.

A number of other methods for attaching the peptide are also envisioned (see, for example, Roberts, et. al. (Roberts, M. J., et al. Advanced Drug Delivery Reviews, 54: 459-476, 2002).

Figure 11C:
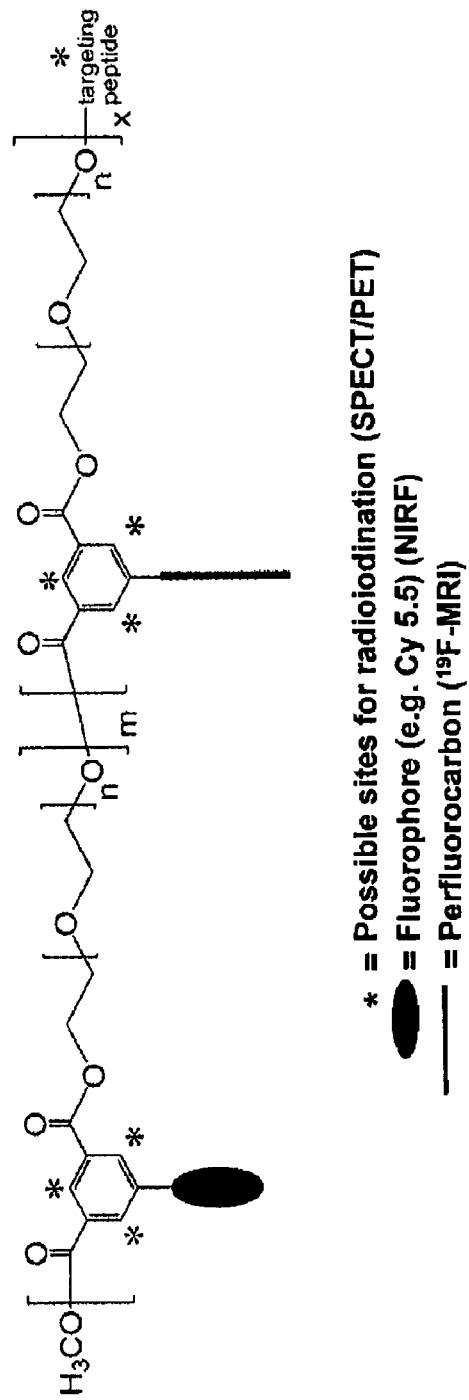
Figure 12:
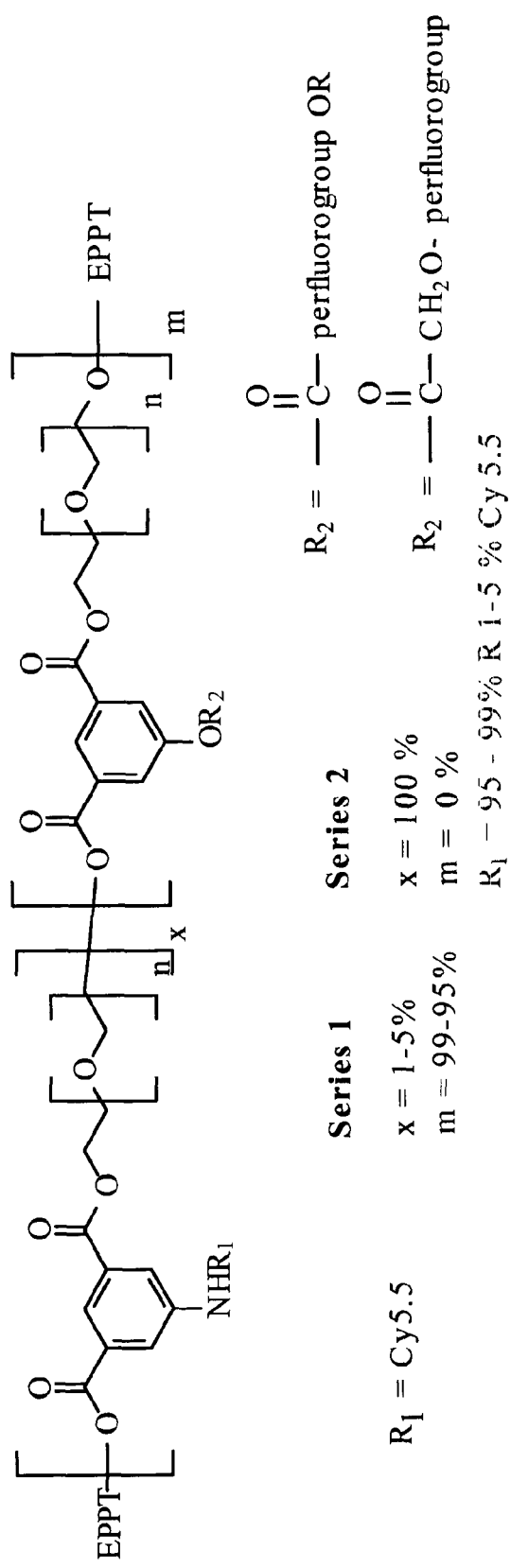
FIG. 12 schematically depicts some embodiments of polymer structures which may be prepared according to the methods of this invention, which may find application as probes for multi-modal imaging.

In order to determine cell binding and biodistribution, the probe may be radiolabeled with Na $^{125}$I with the Iodogen method (Pierce, Rockford, Ill.) using available Tyr within the peptide sequence. The basic polymer backbone itself may be radiolabeled with the same procedure because the isophthalate ring is substitutable in the same manner as the tyrosine aromatic ring. Nanospheres may have a substituted phenolic aromatic ring as the linker in polymeric backbone which has the positions ortho and para to the substituted hydroxy group available for substitution, as shown in FIG. 11A. The positions indicated by the arrows would be available to substitute radiolabeled iodine. Utilization of commercially available kits would give single or multiple substitutions on these aromatic rings. The EPPT1 peptide also has a tyrosine moiety which would also be susceptible to iodine substitution via the same procedures. The number of iodines bound per polymer chain (i.e. specific activity) is controlled by the radioiodine concentration and reaction time. Substitution at many of these active sites would provide a relatively "hot" sample which could be utilized for in vivo imaging or RIT studies in mice, if desired.

It is also possible to encapsulate chelated yttrium and indium by appropriately modifying the nanospheres. These radionuclides may be utilized with the nanospheres containing the targeting peptides to further enhance the sensitivity of the imaging with radioactive nuclei. Technetium may also be similarly used.

In order to track the encapsulated cargo of the nanoparticles, fluorescent labeling of perfluorocarbon is desirable. In one embodiment, Rhodamine B is converted to its acid chloride form and treated with 1,1,2,2 tetrahydro perfluorododecanol to form the esterified perfluoro compound. This will then be encapsulated with the perfluorinated basic polymer. This modification will allow tracking of the cargo by fluorescence microscopy.

It is also possible to synthesize polymers with labeled perfluorinated side chains as shown in FIG. 11B. The synthesis of Rhodamine B-labeled perfluorinated bromo compounds utilizes enzymatic synthesis involving the lipase Novozyme-435. It is possible to selectively monoacylate a number of compounds with bromoacetic acid. Alkylation of the phenolic hydroxyl group of the polymer with the Rhodamine B-labeled perflurorinated bromo compound results in the desired polymer with labeled perfluorinated side chains. This sequence represents another embodiment for a method of attaching the fluorinated groups to the polymer backbone.

The final polymer structure(s) is, in one embodiment, the sum of the above syntheses as shown in FIG. 11.

The final structures may then be analyzed for (1) elemental analysis (Galbraith, Knoxville, Tenn.) of loaded and not-loaded nanoparticles to determine fluorine content, (2) number of Cy5.5 molecules, (3) number of peptides, (4) particle size (N4-MD, Coulter), and (5) isotope binding yield. Absorption spectra of the probe will be taken using a Hitachi 3500 spectrophotometer (Amax for Cy5.5 is at 675 nm). The syntheses described may be adjusted in order to optimize these parameters.

The morphology of the micelles and the size of the corona and core may be visualized by cryogenic transmission electron microscopy according to the method described (Lam, Y. M., et al. Molecular Simulation, 30: 239-247, 2004). In order to form a monolayer of micelles, which is optimal for observation under a transmission electron microscope, aqueous solutions of varying concentrations is vitrified. Approximately 2 μL of solution is applied to a carbon grid while the system is maintained at 40° C. in a high humidity freezing apparatus for 30 s. The grid is blotted with a double layer of filter paper for 5-10 seconds and then plunged into liquid ethane. The vitrified sample is placed in a cryotransfer holder maintained at liquid nitrogen temperature ~170° C. TEM images of the sample will then be recorded on a high resolution cryo-electon microscope (JEOL 2200 FS) available at the Whitehead-MIT Bioimaging Center. The size and shape of the micelles are observed and qualitative and quantitative assessments made.

Example 7

Specificity and Cellular Uptake of the Candidate Probes by uMUC-1-positive and uMUC-1-negative Tumor Cell Lines For targeted multi-modal imaging probes labeling of tumor cells to be "visible" for the imaging systems using $^{19}$F-MR imaging, it is necessary to attain a sufficiently high cell-associated probe concentration, a large number of binding sites for the EPPT1 peptide, a rapid rate of accumulation, high specificity, etc.

In order to measure the amount of cell-associated nanoparticle probes (and by inference the amount of fluorine) as a function of the probe solution concentration and incubation time, cell lines having different disseminating potential may be used, since the probe should accumulate not only in primary tumors but also in metastatic sites. Probe specificity may be determined by comparing probe accumulation results for normal cells, uMUC-1-positive and uMUC-1-negative tumor cells. Cell viability assays may be performed with cells having maximal cellular accumulation of probes to investigate effects on cell viability.

The probe is radiolabelled with Na$^{125}$I using the Iodogen method (Pierce, Rockford, Ill.) using available Tyr within the EPPT1 peptide. Cell lines used may be, for example, those listed in Table 3.

TABLE 3

Cell lines used for measurement of cellular accumulation of probes

| Cell line | Tissue | MUC-1 expression |
| --- | --- | --- |
| CAPAN-2 | pancreas | + |
| LS174T | colon | + |
| ChaGo-K-1 | lung | + |
| NCI-H661 | lung; metastatic site: lymph node | − |
| ZR-75-1 | breast | + |
| BT-20 | breast | + |
| MCF10-A | normal breast; fibrocystic disease | − |
| RF-1 | stomach | + |
| RF-48 | stomach; metastatic site: ascites | − |
| OVCAR-3 | ovary | + |
| DU-145 | prostate | + |
| LNCaP | prostate | − |
| U87 | glioma | − |
| 293 | primary embryonic kidney | − |
| primary; macrophage | peritoneum | − |

Cells are incubated with increasing concentrations of $^{125}$I-labeled probe for different time periods at 37° C. in a humidified CO₂ atmosphere, followed by extensive washing with HBSS. After the final wash, cells are lysed with 0.1% Triton X, and cell lysates are counted in a gamma counter (1289 Compugamma LS; Wallac, Turku, Finland). The relationship between $^{125}$I radioactivity and probe are measured using solutions with known probe concentrations. Cell number or cell concentration are estimated by flow cytometry to calculate the amount of probes associated per cell after each measurement Once the amount of fluorine accumulation in 10 million cells is within the detection limit of MRI, then $^{19}$F-MRI phantoms are prepared using cell pellets. Selected cells may be subjected to cell viability assays with MTT (mitochondrial function), caspase activation (apoptosis), and 7-AAD (membrane integrity).

Differential binding of targeted nanoparticles to adenocarcinoma (CAPAN-2, HT-29, LS174T, BT-20, and ChaGo-K-1) versus control (MCF10A, 293, and U87) cell lines may also evaluated using fluorescence microscopy. Cells are grown overnight on coverslips, fixed in 4% paraformaldehyde, incubated with targeted probes, and washed. Cells are identified under a bright-field microscope and then subjected to correlative dual-channel fluorescence microscopy in the green (for FITC detection) and NIR (for Cy5.5 detection) channels, using an inverted fluorescent microscope (Zeiss Axiovert 100TV, Zeiss, Wetzlar, Germany). Images are collected using a cooled charge-coupled device (Photometrics, Tucson, AZ) with appropriate excitation and emission filters (Omega Optical, Brattleboro, Vt.).

The Cy5.5 and FITC fluorescence intensity in cell lysates and in known samples containing known probe concentrations are measured, for example, with a plate reader (BMG PolarStar, BMG Labtech, Offenburg, Germany). Scatchard plot analysis is used to estimate RT, the number of receptors per cell, and $K_{D,eff}$, the effective affinity of the probe for the cell. Optimization of these procedures such that probe accumulation is sufficient for MR and/or NIRF imaging, with the Scatchard plot analysis providing an estimate of the effective affinity of the multivalent probe for the cell (Schwartz, A. L., et al. Journal of Biological Chemistry, 257: 4230-4237, 1982).

Example 8

Temporal Cellular Distribution of the Candidate Probes

In order to optimize nanoparticle uptake, retaining their high specificity, fluorescently labeled perfluorocarbon-containing nanoparticles are evaluated for nanoparticle distribution and nanoparticle disintegration in UMUC-1-positive and uMUC-1-negative tumor cell lines and normal cells. Cells are seeded in 35 mm cell culture dishes and six-well plates containing 22 mm-diameter glass cover slips at a density of 1.5×10⁵ cell/mL and incubated with nanoparticle concentrations that give maximal uptake, as described in Example 7. Laser scanning confocal micrographs will be recorded using, for example, a Zeiss LSM 510 Meta high-resolution laser scanning confocal microscope (Carl Zeiss AG). Scanning speed and laser intensity will be adjusted to avoid photobleaching of the fluorescent probes and damage or morphological changes of the cells. The microscope will be equipped with a microcultivation system (Incubator S, CTI controller 3700 digital, Zeiss) to control temperature, humidity and CO² for maintaining physiological conditions during experiments. Image analysis and fluorescence signal quantification will be performed using, for example, Zeiss LSM software.

In order to investigate subcellular probe distribution, selective labeling of different cellular organelles will be conducted as described (Savic, R., et al. Science, 300: 615-618, 2003): (1) plasma membrane with 5-dodecanoylaminofluorescein (DAF, green), (2) nuclei with Hoechst 33342 (blue), (3) lysosomes with lysotracker DND-26 (green), (4) mitochondria with Mito-Tracker Green FM (green), (5) Golgi apparatus and endoplasmic reticulum (ER) with Brefeldin A BODIPY FL conjugate (green), and (6) mitochondria and ER with 3,3'-dihexyloxacarbocyanine iodide (green). When using green dyes for labeling organelles, it will be necessary to remove FITC from the EPPT1 peptide. Probes with no peptides will serve as controls for all experiments.

A spinning-disk confocal microscope, such as, for example, the Perkin Elmer PE Ultraview RS100, equipped with a high speed digital cooled CCD camera with a 1.5 s scan time for 3-D images that is suitable for producing time-lapse video of rapid events may similarly be used.

Example 9

Biological Characterization of Multi-modal Imaging Probes

In order to determine the accumulation of the probe in different organs, and/or the signal to noise ratio for MR imaging of the tumors a bi-lateral tumor propagation method (Weissleder, R., et al. Nature Medicine, 6: 351-354, 2000; Moore, A., et al. Radiology, 221: 751-758, 2001) will be used, where uMUC-1-positive tumor will be injected in one flank of the mouse and uMUC-1-negative tumor will be injected in the opposite flank, and include tumors with different metastatic potential. The accumulation of the probe at primary and metastatic sites is evaluated.

Animals are anesthetized with an intraperitoneal injection of ketamine/xylazine (80 mg/kg/12 mg/kg, Parke-Davis. Morris Plains, N.J./Miles Inc., Shawnee Mission, Kans.). Tumor cells (uMUC-1+ and uMUC-1-) are injected in the flanks of nu/nu mice (n=5/pair; approximately 5×10⁶ cells/flank depending on the tumor doubling time). Tumors are allowed to grow to 0.5 cm in size, and animals are injected intravenously with $^{125}$I-labeled $^{19}$F nanoparticle probes. Animals are sacrificed, for example, 24, 48 and 72 hours later by lethal IV injection of sodium pentobarbital (200 mg/kg). Tumors, tumor metastasis, the pancreas, spleen, liver, heart, intestine, lung, lymph nodes, thymus, blood, bone, muscle, brain and fat are excised, weighed and radioactivity is measured in a gamma counter. Aliquots of the probes are counted simultaneously to correct for radioactive decay and to calculate the dose in each organ. Biodistribution results are expressed as the percentage of the injected dose per gram of tissue (% ID/g).

$^{125}$I-labeled probe in tumor bearing animals (n=5) is assessed. Blood half-life of the probe is determined after intravenous injection of 50 µCi/animal of the $^{125}$I-labeled $^{19}$F nanoparticles. Blood samples are withdrawn over several time points from the tail vein, weighed, and radioactivity in the blood is counted in a gamma-counter. Blood half-life is calculated as described (Ritschel, W. Handbook on Basic Pharmacokinetics, 3d edition, p. 168-190. Hamilton, Ill.: Drug Intelligence Publications, Inc., 1986). The preparation of Cy5.5-labeled 19F nanoparticles with no peptides attached and/or with nonsense peptide serve as controls for all studies.

Results with acute oral toxicity testing indicated that the nanospheres with a hydrocarbon side chain have little or no toxicity. The nanoparticles for $^{19}$F-MR imaging contain perfluorocarbons, which have been used extensively in artificial blood applications, and most are generally viewed as biologically inert. An acute lethality (LD50) test may be used to determine if the greater concentrations used in the applications of this invention result in toxicity.

A basal cytotoxicity test may be initially conducted to predict a starting dose for an in vivo lethality test. The neutral red uptake (NRU) test may be undertaken with BALB/c 3T3 cells (NIH Guidance Document on Using In Vitro Data to Estimate In Vivo Starting Doses for Acute Systemic Toxicity, NIH Publ 01-4500. pp. 48. Research Triangle Park, N.C., USA: NIEHS, 2001). NR is a weak cationic dye that readily penetrates cell membranes by non-ionic diffusion and accumulates intracellularly in lysosomes. Alterations of the cell surface or the sensitive lysosomal membrane lead to lysosomal fragility and other changes that gradually become irreversible, leading to a decreased uptake and binding of NR. It is thus possible to distinguish between viable, damaged, or dead cells, which is the basis of this assay. Healthy BALB/c 3T3 cells, when maintained in culture, continuously divide and multiply over time. A toxic chemical, regardless of site or mechanism of action, will interfere with this process and result in a reduction of the growth rate as reflected by cell number. Cytotoxicity is expressed as a concentration dependent reduction of the uptake of the vital dye, NR, after one day (one cell cycle) of chemical exposure, thus providing a sensitive, integrated signal of both cell integrity and growth inhibition.

BALB/c 3T3 cells are seeded into 96-well plates and maintained in culture for 24 hours to form a semi-confluent monolayer. Cells are exposed to the nanoparticles over a range of concentrations. After 24 hours exposure, NRU is determined for each treatment concentration and compared to that of control cultures. For each concentration of the test chemical, the percent inhibition of growth is calculated. The $IC_{50}$ (the concentration producing 50% reduction of NR uptake) is calculated from the concentration-response and used to estimate the starting dose for lethality test.

In one embodiment, an acute lethality test may comprise targeted nanoparticle administration into the tail vein of 20-25 gram ICR mice. Different dose levels are used, and a number of animals are given each dose. The animals are observed for, for example, 14 days, with the $LD_{50}$ determined by the Reed-Muench method (Reed, L. J. and Muench, H. Am J Hyg, 27: 493-494, 1938), and the safety factor calculated as the ratio of $LD_{50}$ to the effective dose.

Example 10

In Vivo Imaging of uMUC-1-Expressing Human Tumors $^{19}$F MR spectral characteristics of nanoparticles taken up in cells such that optimal imaging is achieved, may nonetheless be influenced by changes in the $^{19}$F MR spectrum, which negatively affect image formation (for example, resonance line-widths must not be substantially broadened on binding such that the T2* becomes too short for imaging).

Toward this end, uMUC-1-positive tumors are grown in animals as described hereinabove, after which animals are injected intravenously with non-radiolabeled $^{19}$F nanoparticle probes and sacrificed. Tumors and metastases are harvested and analyzed ex vivo by $^{19}$F NMR spectroscopy at 14T field strength, 37° C. For each specimen, single pulse static (non-spinning) and 2.5 kHz magic angle spinning (MAS) spectra are obtained. T1 is measured by inversion recovery and T2 measured by CPMG in MAS spectra. The static spectra yields the best estimate of the appearance of the in vivo spectrum, and is used to calculate T2* (=1/π° FWHH) for each resolved chemical shift band.

By tabulating T2, T2* and T1, an early predictor for the performance of the nanoparticles under in vivo imaging conditions is obtained. The T2* (a measure of the inverse linewidth) of any resonance must not be below the order of a few ms in order for imaging to be successful based on that resonance. The T2* will be affected by the degree of molecular motion, with nanoparticle binding potentially creating T2* values which are too short for particular resonances to be used for image creation. Shortening of T1 on binding or aggregation, improves image signal to noise ratio, making it useful to identify resonances with advantageously short T1s. Although chemical shift selective pulses have been used in $^{19}$F MRI in order to select out of a complicated chemical shift spectrum just a single resonance that is used for image creation, this results in much (or most) of the potentially available fluorine signal to be discarded.

The determination of T2, T2* and T1 for each resonance band enables an assessment of which resonances in the chemical shift spectrum can be profitably used in image creation.

The magic angle spinning spectra of the tissue specimens yield the highest spectral resolution and lowest detection limits because the spinning eliminates isotropic magnetic susceptibility broadening effects (Cheng, L. L., et al. Magnetic Resonance in Medicine, 36: 653-658, 1996). MAS spectroscopy has become the standard for measurement of proton NMR spectra of tissue specimens. Each resonance in the PFC chain is resolvable with this technique, and hence amenable to assessment for its contribution to image creation. Interestingly, despite the availability of this technique in tissue NMR spectroscopy for almost a decade, there have been no reports of its use for $^{19}$F spectroscopy of tissue specimens. Although $^{19}$F generally has much larger chemical shifts than protons, making the elimination of susceptibility broadening potentially less important for most applications of 1$^{9}$F tissue spectroscopy, the severe crowding and complexity of the CF2 resonances in the nanoparticle spectra may accrue substantial benefits from MAS spectroscopy.

In order to determine whether the nanoparticle molecular probes of the invention can successfully label tumors for detection by $^{19}$F-MRI, in vivo imaging is conducted. uMUC-1-positive tumors grown in animals to 0.5 cm in size, are injected intravenously with nonradiolabeled $^{19}$F nanoparticle probes and scanned by $^{1}$H and $^{19}$F-MRI, at, for example, 24, 48 and 72 hours post injection. Scanning is performed with, for example, a multinuclear Bruker (Karlsruhe, Germany and Billerica, Mass.) Avance NMR console interfaced to a 14 T (600 MHz proton frequency) Magnex (Oxford, UK) actively shielded 89 mm vertical superconducting magnet. Animals are physiologically supported (if necessitated by the vertical positioning and long exam time) with a ventilation system and monitored for respiration, core temperature, and ECG. The animals are suspended head-up (by a bite bar arrangement) in a Bruker Micro 2.5 microimaging probe. A Teflon-free dedicated Bruker 19F 30 mm cylindrical RF resonator is used for excitation and detection of both $^{1}$H and $^{19}$F images. This resonator, although optimized for $^{19}$F MRI, will also tune to $^{1}$H without removal of the animal from the magnet and performs proton MRI.

The anesthetized animal is positioned in the magnet, stabilized, with a triplane proton scout image used to roughly locate the tumor area. Multi-slice proton T1-weighted spin echo and T2-weighted gradient echo images (256×256 matrix size, 0.5 mm slice thickness) are obtained to delineate the tumor and surrounding area. The resonator is tuned to the $^{19}$F frequency (564 MHz) and imaged by $^{19}$F MRI as described below. The $^{19}$F images (showing the nanoparticle distribution) are overlaid on the $^1$H images (which delineate detailed anatomy).

Because of the lower signal to noise ratio of the $^{19}$F signal and the broad chemical shift range, all $^{19}$F images are non-slice selective (projective). Several MRI techniques are explored. In order to capture as much of the available $^{19}$F signal as possible, chemical shift selective pulses may not be used. The most direct method for total-$^{19}$F MRI is to use small magnetic field gradients, which do not cause overlap of projections from different chemical shift bands. In the case of the nanoparticle probe spectra obtained at 14T under in vivo-like conditions (using the imaging probe and a low resolution sample holder), the linewidths of the CF3 and CF2 bands are about 0.5 ppm (based on spectra we obtained with the nanoparticles). This linewidth arises primarily from unresolved J-couplings in the CF3 band and the bands from CF2 adjacent to either CF3 or the polymer linkage (at 85, 40 and 49 ppm from C6F6 respectively). The remaining CF2 band centered at 44 ppm contains -multiple chemical shifts as well as the couplings. A 5 ppm projection width will just barely avoid overlap of these bands, and will provide 10 pixels of linear image resolution across the subject, a spatial resolution comparable to the true resolution obtained in other in vivo $^{19}$F applications in the literature. Use of a larger gradient results in higher spatial resolution, but lower signal to noise ratio. This method can be applied to both projection (radial) reconstruction and phase encoded approaches toward building a 2D image.

A second approach may use mathematical deconvolution to remove the resolution-degrading effects of the chemical shift spectrum from the image. It requires that the chemical shift spectrum be constant in shape (although it may vary in intensity) at every position in the field of view, which is applicable for the nanoparticles of this invention. An approximate reconstruction is possible, and a high quality reconstruction can be obtained. Sharp, high quality projection reconstruction $^{19}$F images may be obtained from perfluorocarbon systems by deconvolving the spectrum from the projections prior to reconstruction (Busse, L. J., et al. Medical Physics, 13: 518-524, 1986). The deconvolution is most efficiently carried out in the time/k-space domain. A complex reference FID (if the spatial reconstruction is performed on FIDs) corresponding to the spectrum (with no gradients applied) is inverted, and then multiplied by a window function to avoid the blowup at long times where the FID is small in magnitude. The window function is constructed as a Weiner filter to maintain an optimal adaptive approach that takes into account the instantaneous relative magnitudes of signal and noise power in the FID so that random noise is not unduly amplified. The method is equally applicable to both FID and echo based reconstructions. Because the chemical shift and J-coupling have different behavior as a function of field strength, it is essential that the reference data be obtained at the field at which imaging is carried out. Both FID and gradient echo imaging require an FID reference function, whereas spin echo imaging requires a spin echo reference function. The projection (or frequency encoded) data are multiplied by the inverted/windowed reference on a pixel by pixel basis to yield the deconvolved projections which may then be used in a conventional reconstruction.

Although most imaging today employs spin echoes, there is an advantage to using FIDs for the input to the reconstruction. Because perfluorocarbons exhibit significant J-coupling (which is not refocused by a 180 degree RF pulse), in the creation of a spin echo (by means of an RF pulse) the chemical shift and other resonance offset interactions (e.g., static magnetic susceptibility) are refocused at the echo, whereas the J-coupling is not. Therefore, significant oscillatory dephasing still occurs at the echo, and this J-modulation varies strongly with the echo time TE. The optimum approach to eliminating this source of artifact and signal loss is to use reconstruction from projections (radial imaging), such as is done for solid state MRI (Wu, Y., et al. Calcified Tissue International, 62: 512-518, 1998; Wu, Y., et al. Proceedings of the National Academy of Sciences of the United States of America, 96: 1574-1578, 1999; Wu, Y., et al. Magnetic Resonance in Medicine, 50: 59-68, 2003; Ramanathan, C. and Ackerman, J. L. Magnetic Resonance in Medicine, 41: 1214-1220, 1999). We have extensive experience with projection reconstruction in two and three dimensions, and can use software developed in house for this work.

Images obtained are analyzed for spatial resolution (in phantoms), for signal to noise ratio and contrast to noise ratio. These results may be correlated with NIRF, immunohistochemical, and histological image data aquired from the same animals.

In vivo NIRF imaging of uMUC-1-expressing tumors in mouse models of human cancer may also be performed. Tumor bearing mice injected with the probe above are used. Near-infrared reflectance optical imaging is performed using a whole mouse imaging system as described in (Mahmood, U., et al. Radiology, 213: 866-870, 1999). Cy5.5 fluorescence is measured with the appropriate filters, and mice are monitored for a period of 3 to 4 weeks post injection, with probe assessed as a function of NIRF signal intensity. As the tumors grows, signal intensity is plotted as a function of tumor volume, which is obtained from caliper measurements and an indirect calculation of tumor volume based on the doubling time for the particular tumor. Animals are sacrificed after the completion of MR and NIRF imaging sessions; tumors are excised and subjected to NIRF imaging as described.

$^{125}$I nuclear imaging may also be used, for example for imaging of uMUC-1-expressing tumors in mouse models of human cancer. The uptake ratio and the time course of the probe accumulation may be collected, with imaging at successive time points.

Probes are prepared to inject approximately 3.7 GBq of activity in each experiment. Measurements may be performed using a low-energy high-resolution collimator on a large field of view Isocam II (Isocam Technologies Inc., Castana, Iowa) gamma camera. Subjects are placed flat on the surface of the collimator and imaged. Subsequently, pinhole SPECT may be performed using the same camera. Subjects are placed in a vertical position in front of a pinhole collimator mounted on one of the heads of the Isocam II (Isocam Technologies Inc., Castana, Iowa) gamma camera available at the MIT Nuclear Science and Engineering Department. The subject may be positioned at a distance from the pinhole sufficient for the acquisition of a whole body 2D image, and 2d images will be corrected for parallax. The subject is then moved axially to the height of the lesion. Fiducial markers will be placed next to the subject, to aid the estimate of the axial shift if necessary. The support is moved closer to the pinhole (~3 cm radius of rotation) and rotated in a step and shoot protocol for the acquisition of 60 to 180 angular projections. Literature methods will be used for a careful registration of the imaging parameters, notably the center of rotation. All these techniques are well-established and proven in the nuclear imaging field. For examples of pinhole SPECT see (Acton, P. D., et al. European Journal of Nuclear Medicine, 29: 691-698, 2002; Schramm, N. U., et al. IEEE Transactions on Nuclear Science, 50: 315-320, 2003; Moore, R. H., et al. Cancer, 32: 987, 1991; Strand, S.-E. et al. Cancer, 73: 981-984, 1994; Weber, D. A. et al. Journal of Nuclear Medicine, 35: 342-348, 1994; Jaszczak, R. J., et al. Physics in Medicine and Biology, 39: 425-437, 1994; Ishizu, k. et al. Journal of Nuclear Medicine, 36: 2282-2287, 1995; Booij, J., et al. European Journal of Nuclear Medicine, 29: 1221-1224, 2002; Acton, P. D. and Kung, H. F. Nucl Med Biol, 30: 889-895, 2003. ).

Alternatives/Data analysis. In the very unlikely event that 2D and 3D pinhole imaging should fail, parallel hole collimator images will be acquired to obtain low-resolution estimates of the biodistribution of the radiotracer. Given the large Fov of the camera, several animals can be evaluated at the same time. Pinholes of different diameters (e.g. 0.25, 0.5, 1 and 2 mm) will be designed and fabricated. The availability of several pinholes will allow the optimization of the resolution-sensitivity trade-off for image quality. The best pinhole diameter will be chosen in preliminary phantom experiments with phantoms representative of the expected uptake ratios. Phantom images will be evaluated for resolution and contrast recovery via region of interest analysis. Projection data will be reconstructed with an Ordered Subset Expectation Maximization (OSEM) iterative algorithm. Regions of interest will be drawn in the reconstructed image to evaluate uptake ratios from the ratio of counts in a target and in a background region. To increase sensitivity, data can be acquired on opposite sides of the animal by using the second head of the camera, for which a second set of pinholes will be fabricated.

In order to follow intra-tumoral probe distribution at the microscopic level, immunohistochemistry and histologic evaluation of the tumors will be correlated with results of MR, NI and NIRF studies.

Colocalization of the MR, NI and NIRF signals with staining for uMUC-1, FITC, and Cy5.5 fluorescence may be assessed. After imaging sessions, tumors are excised and snap frozen in liquid nitrogen. Immunohistochemistry probing sections with mouse monoclonal antibodies B423 (VU4H5) against uMUC-1 60-mer tandem repeat (Biomeda, Foster City, Calif.) is followed by incubation with PE-labeled rabbit anti-mouse antibody (Pharmingen, San Diego, Calif.). Dual channel fluorescence microscopy is performed on consecutive sections.

Microscopic sections are digitized using, for example, a Polaroid SprintScan 35-mm scanner (Polaroid Corporation, Cambridge, Mass.) and a PathScan Enabler System (Meyer Instruments, Inc., Houston, Tex.). MR and NIRF images and corresponding digitized histological sections are displayed in a graphics package, such as, for example, Photoshop™ and matching structures are identified, as described (Benveniste, H., et al. Proceedings of the National Academy of Sciences of the United States of America, 96: 14079-14084, 1999). The shape and arrangement of blood vessels within the tissue may be used as landmarks. Approximation between histological sections and MR images may be further improved by modifying the imaging plane in the volumetric MR data. The volumes of individual hypointense spots on the 3D MR images are measured and correlated to corresponding staining/fluorescence microscopy.

Example 11

Correlating In Vivo Imaging Data with Biological Function

The in vitro cytotoxicity of therapeutic probes in uMUC-1-positive cell lines and normal cells may also be examined. Incubating the target uMUC-1-positive and uMUC-1-negative tumor cells and normal cells with empty nanoparticles and nanoparticles containing the anti-cancer agent, with and without targeting peptide, may be assessed for effects on cell death, which may be determined by various assays.

To determine cell death, methods may include incubating uMUC-1-positive, uMUC-1-negative, and normal cells with increasing concentrations and various nanoparticle types for time periods ranging from 6 hours to 3 days at 37° C. in a humidified $CO_2$ atmosphere, followed by extensive washing with media. Cell samples at each time point and for each particle concentration may be subjected to cell viability assays with MTT (mitochondrial function), caspase activity (apoptosis), and 7-AAD (membrane integrity). The MTT Assay (Molecular Probes, Vybrant® MTT Cell Proliferation Assay Kit V-13154) is a measure of the reducing environment in cells. The MTT reagent is a water soluble tetrazolium compound (3-(4,5-dimethylthiazol-2-yl)-2,5-diphenyltetrazolium bromide) that is reduced to an insoluble formazan product. A known concentration of cells, for example, is resuspended in DPBS containing 20 mM glucose. 20 µl of MTT reagent (5 mg/mL) and 100 ml of cell suspension will be added to each well and the microplate will be placed in an incubator at 37° C. for 4 hours. A 100 µl aliquot of a 10% (w/v) SDS and 0.01 M HCl solution is added to each well and incubated at 37° C. for 4-18 hours. The absorbance at 570 nm is determined on an ELISA plate reader and compared with controls. Caspase activity is measured, for example, with the Guava MultiCaspase Kit, which determines the fractions of a cell population that are live, early apoptotic, late apoptotic, and dead. This assay measures caspase activity as well as membrane integrity. The assay kit contains SR-VAD-FMK (sulforhodamine-valyl-alanyl-aspartyl-fluoromethylketone), a fluorochrome-conjugated inhibitor of caspases which binds to apoptotic cells, and 7-AAD, a membrane integrity dye which stains late apoptotic and dead cells. SR-VAD-FMK penetrates all cells but only binds to active caspases and can be washed away from non-apoptotic cells. 100 ml of cell suspension in Apoptosis Wash Buffer will be stained with SR-VAD-FMK and incubated for 1 hour at 37° C. The cells are washed three times with Apoptosis Wash Buffer, after which 5 ml of 7-AAD reagent is added to each sample and incubated for 10 minutes at room temperature. The samples are analyzed using the Guava Personal Cell Analysis System (Guava Technologies), a novel flow cytometer.

Other methods may be used to assess cytotoxic effects of specific agents, for example as outlined herein, when doxorubicin and $^{131}I$ are incorporated. Once internalized by the cell $^{131}I$ remains attached to the polymer to which it is covalently bound, thus $^{131}I$ may be conjugated to the polymer. Since the antitumor activity of doxorubicin requires direct interactions with DNA or DNA topoisomerase, doxorubicin should be released from polymer, in order to gain access to the nucleus of the cell. Nanoparticles/micelles loaded with radiolabel and doxorubicin may be diluted in PBS (1:1 by volume), loaded in a dialysis cassette (molecular weight cutoff of 10,000 Da), and dialyzed against 50% PBS at 37° C. At different time points, aliquots may be measured for doxorubicin concentration. The results will be expressed as $t_{1/2}$ (time in which 50% of drug exits the nanoparticle/micelle).

Pharmacokinetic data (biodistribution, blood half-life) in terms of drug affinity and accumulation in uMUC-1-positive primary tumors and metastasis in vivo may be assessed.

In vivo cytotoxicity studies in for example, a mouse model of human cancer may be conducted as well. Survival time and tumor volume following administration of targeted therapeutic probes containing doxorubicin may be evaluated. For example, nu/nu mice injected subcutaneously with uMUC-1- positive and uMUC-1-negative tumor cell suspensions are assessed for tumor volume via calipers (0.5 cm in diameter). Single- and multiple-dose treatment studies may be conducted with the drug, given intravenously. Tumor growth may be assessed twice a week by caliper measurements. Tumor volume may be calculated using the equation for the volume of a prolate ellipsoid: $(a \times b^2) \times \pi/6$, where a is the larger and b is the smaller dimension of the tumor. The results may be expressed as relative tumor volume, Vt/Vo, where Vo is the tumor volume at the start of the treatment and Vt is the tumor volume at any given time point.

Results from in vivo cytotoxicity experiments may be correlated with in vivo $^{19}$F MR, NIRF, and/or nuclear imaging. The time course of nanoparticle/micelle accumulation by imaging during treatment may be evaluated. In addition, histology of excised tumors may be correlated with apoptosis and/or differential uMUC-1 expression in vivo in response to therapy. For the latter, quantitative RT-PCR may be used to determine changes in uMUC-1 expression. The following primers and probes specific for the MUC-1 5' non-repeat region may be used:

Forward primer, 5'-ACAGGTTCTGGTCATGCAAGC-3' (SEQ ID NO: 3);
Reverse primer, 5'-CTCACAGCATTCTTCTCAGTA-GAGCT-3' (SEQ ID NO: 4)
TaqMan Probe, 5'-FAM-TGGAGAAAAGGAGACTTCG-GCTACCCAGA-TAMRA-3' (SEQ ID NO: 5).

Although the invention has been described in conjunction with specific embodiments thereof, it is evident that many alternatives, modifications and variations will be apparent to those skilled in the art, any of which are to be considered as part of this invention.

What is claimed is:

1. An amphiphilic polymer, characterized by the structure of the general formula I:

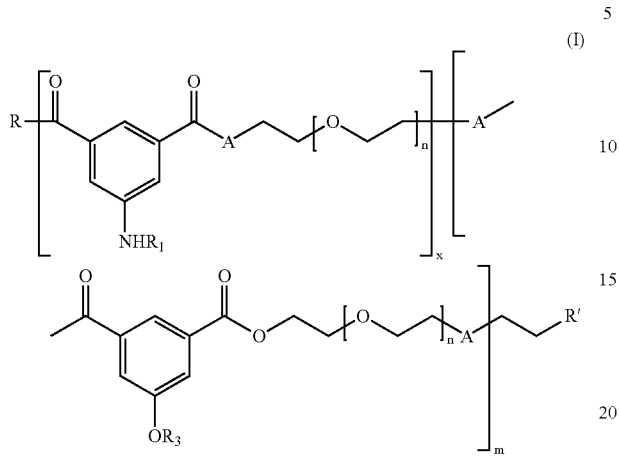

wherein

R is a hydroxyl, O-alkyl, O-Acyl, O-Activating group, SH, S-alkyl, an acid activating group comprising halogen, O-vinyl, O-allyl, O-aryl, OCOalkyl, OCOaryl, OCH$_2$CF$_3$, or NH$_2$;

R' is OH, NH$_2$, or SH;

each R$_1$ group is, independently,

a perfluorocarbon, a perfluorocarbon-R$_4$, a perfluorocarbon-OR$_4$, or

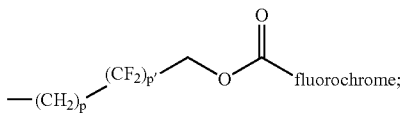

each R$_2$ group is, independently, perfluorocarbon, a perfluorocarbon-R$_4$, a perfluorocarbon-OR$_4$, or

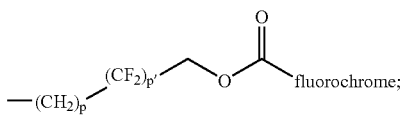

each R$_3$ group is, independently,

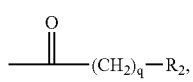

a drug, a labeling agent, or a targeting moiety; or OR$_3$ is a fluorinated ether group;

each R$_4$ group is, independently, an alkyl group, an alkylene group, a carboxylate group, a carboxylic acid group, an amino group, an ammonium group, an alkoxyl group, a hydroxyl group, or another nitrogen, oxygen, or sulfur-containing group;

each A group is, independently, O, NH, S,

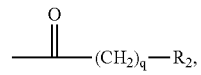

an acyl group, an aryl group, a linear or branched alkenyl group, or a linear or branched alkyl group, t, n, m, p, p' and x are integers, such that the weight of a fraction of the polymer ranges between 0-5% or 6-99% or 50-100% of the weight of said polymer, wherein said fraction is represented by the structure:

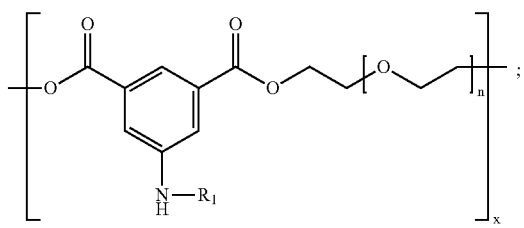

and q is an integer between 0-10;

wherein

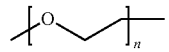

comprises a molecular weight of from 60 to 10,000 Daltons; and wherein:

x is greater than 0 and the R$_1$ or R$_2$ group consists of a perfluorocarbon, a perfluorocarbon-R$_4$ or a perfluorocarbon-OR$_4$, wherein any of said perfluorocarbons is further selected from the group consisting of (CF$_2$)$_z$CF$_3$ wherein z is an integer, CH$_2$OCH$_2$(CF$_2$)$_8$CF$_3$, CH$_2$OCH$_2$(CF$_2$)$_6$CF$_3$, CH$_2$OCH$_2$(CF$_2$)$_4$CF$_3$, and CH$_2$OCH$_2$CH$_2$(CF$_2$)$_{11}$CF$_3$; or m is greater than 0 and the OR$_3$ group consists of a fluorinated ether group, wherein said fluorinated ether group is further selected from the group consisting of CH$_2$OCH$_2$(CF$_2$)$_8$CF$_3$, CH$_2$OCH$_2$(CF$_2$)$_6$CF$_3$, CH$_2$OCH$_2$(CF$_2$)$_4$CF$_3$, and CH$_2$OCH$_2$CH$_2$(CF$_2$)$_{11}$CF$_3$, or the R$_2$ group consists of a perfluorocarbon, a perfluorocarbon-R$_4$ or a perfluorocarbon-OR$_4$ wherein any of said perfluorocarbons is further selected from the group consisting of (CF$_2$)$_z$CF$_3$ wherein z is an integer, CH$_2$OCH$_2$(CF$_2$)$_8$CF$_3$, CH$_2$OCH$_2$(CF$_2$)$_6$CF$_3$, CH$_2$OCH$_2$(CF$_2$)$_4$CF$_3$, and CH$_2$OCH$_2$CH$_2$(CF$_2$)$_{11}$CF$_3$; or both x and m are greater than 0 and the R$_1$ or R$_2$ group consists of a perfluorocarbon, a perfluorocarbon-R$_4$ or a perfluorocarbon-OR$_4$ wherein any of said perfluorocarbons is further selected from the group consisting of (CF$_2$)$_z$CF$_3$ wherein z is an integer, CH$_2$OCH$_2$(CF$_2$)$_8$CF$_3$, CH$_2$OCH$_2$(CF$_2$)$_6$CF$_3$, CH$_2$OCH$_2$(CF$_2$)$_4$CF$_3$, and CH$_2$OCH$_2$CH$_2$(CF$_2$)$_{11}$CF$_3$, the OR$_3$ group consists of a fluorinated ether group, wherein said fluorinated ether group is further selected from the group consisting of CH$_2$OCH$_2$(CF$_2$)$_8$CF$_3$, CH$_2$OCH$_2$(CF$_2$)$_6$CF$_3$, CH$_2$OCH$_2$(CF$_2$)$_4$CF$_3$, and CH$_2$OCH$_2$CH$_2$(CF$_2$)$_{11}$CF$_3$.

2. The polymer of claim 1, wherein any of said perfluorocarbons is $(CF_2)_zCF_3$, wherein z is an integer.

3. The polymer of claim 2, wherein any of said perfluorocarbons is $(CF_2)_8CF_3$, $(CF_2)_6CF_3$, or $(CF_2)_3CF_3$.

4. The polymer of claim 1, wherein any of said perfluorocarbon-$OR_4$— groups is $CH_2OCH_2(CF_2)_8CF_3$, $CH_2OCH_2(CF_2)_6CF_3$, $CH_2OCH_2(CF_2)_4CF_3$ or $CH_2OCH_2CH_2(CF_2)_{11}CF_3$.

5. The polymer of claim 1, wherein if m is 0, then $R_1$ is

and $R_2$ is a perfluorocarbon, a perfluorocarbon-$OR_4$, or a derivative thereof.

6. The polymer of claim 1, wherein any of said targeting moieties is a peptide, an antibody, an antibody fragment, a receptor, Protein A, Protein G, biotin, avidin, streptavidin, a metal ion chelate, an enzyme cofactor, a nucleic acid or a ligand.

7. The polymer of claim 6, wherein said peptide binds to an underglycosylated mucin-1.

8. The polymer of claim 7, wherein said peptide is an EPPT1 peptide (SEQ ID NO: 1).

9. The amphiphilic polymer of claim 1 wherein m is 0 and x is greater than 0.

10. The amphiphilic polymer of claim 1 wherein x is 0 and m is greater than 0.

11. The amphiphilic polymer of claim 1, wherein the polymer comprises a drug.

12. The amphiphilic polymer of claim 1, wherein the polymer comprises a targeting moiety.

13. The amphiphilic polymer of claim 1, wherein the polymer comprises a labeling agent.

14. The amphiphilic polymer of claim 1, wherein the polymer comprises two or more of a drug, a targeting moiety, and a labeling agent.

15. The amphiphilic polymer of claim 1, wherein the polymer comprises a drug, a targeting moiety, and a labeling agent.

16. The polymer of claim 1, wherein said polymer is characterized by the structure of the general formula II:

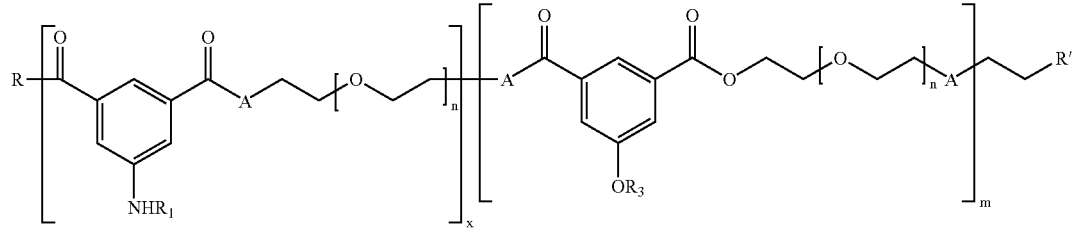

(II)

wherein R'=OH, $NH_2$, or SH;
R=OH, O-Alkyl, O-aryl, O-acyl, or O-activating group;
$R_1$ is, independently,

a perfluorocarbon, a perfluorocarbon-$R_4$, a perfluorocarbon-$OR_4$, or

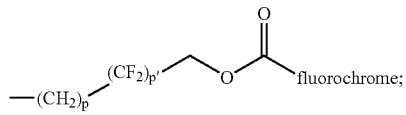

each $R_3$ group is, independently,

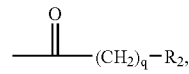

a drug, a labeling agent or a targeting moiety; or
$OR_3$ is a fluorinated ether group; wherein
each $R_2$ is, independently, a perfluorocarbon, a perfluorocarbon-$R_4$, a perfluorocarbon-$OR_4$, or

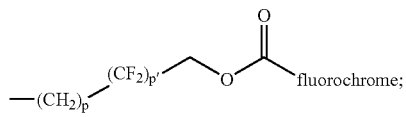

and
A=O, NH, or S.

17. The polymer of claim 16, wherein the weight of a fraction of said polymer ranges between 6-99% of the weight of said polymer, said fraction represented by the structure:

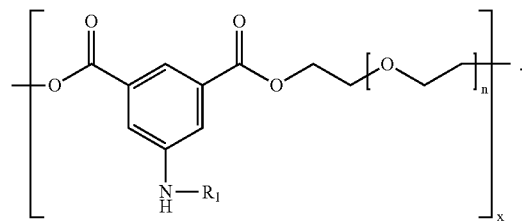

18. The polymer of claim 16, wherein the weight of a fraction of said polymer ranges between 1-94% of the weight of said polymer, said fraction represented by the structure:

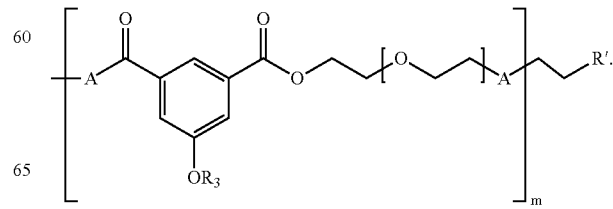

19. The amphiphilic polymer of claim 16, wherein the polymer comprises a drug.

20. The amphiphilic polymer of claim 16, wherein the polymer comprises a targeting moiety.

21. The amphiphilic polymer of claim 16, wherein the polymer comprises a labeling agent.

22. The amphiphilic polymer of claim 16, wherein the polymer comprises two or more of a drug, a targeting moiety, and a labeling agent.

23. The amphiphilic polymer of claim 16, wherein the polymer comprises a drug, a targeting moiety, and a labeling agent.

24. A composition comprising the polymer of claim 1.

25. A micelle comprising the polymer of claim 1.

26. The micelle of claim 25, wherein a fluorochrome, an indole-containing compound, an antibody or antibody fragment, a peptide, an oligonucleotide, a labeling agent, a drug, an enzyme, a chemomimetic functional group, a glycolipid, a metal ion chelate, an enzyme cofactor, a cytotoxic compound, a growth factor, a hormone, a cytokine, a toxin, a prodrug, an antimetabolite, a microtubule inhibitor, a radioactive material, a perfluorocarbon, or a combination thereof, is encapsulated within said micelle.

27. A process for producing an amphiphilic polymer of claim 1 comprising perfluorocarbons, the process comprising the steps of:
   i. contacting a dialkyl 5-hydroxy-isophthalate, a dialkyl 5-alkoxy-isophthalate, a dialkyl 5-amino-isophthalate, any derivative thereof or any combination thereof with a polyethylene glycol to form an amphiphilic copolymer; and
   ii. linking a perfluorocarbon to said amphiphilic copolymer, thereby being a process for producing amphiphilic polymers comprising perfluorocarbons.

28. The process of claim 27, wherein said process is performed in the presence of an enzyme.

29. The process of claim 28, wherein said enzyme is a lipase.

30. The process of claim 27, wherein said linking a perfluorocarbon to said amphiphilic copolymer comprises the step of alkylating the hydroxy group of said isophthalate to produce $—(CH_2)_q CO-R_2$.

31. The process of claim 27, further comprising the step of dissolving said product in water.

32. The process of claim 31, wherein micelles comprising polymeric units of said product self-assemble.

33. A method of imaging a cell, the method comprising the steps of contacting a cell with the amphiphilic polymer of claim 1, wherein the polymer comprises a labeling agent, and imaging said cell, whereby said polymer enables the imaging of said cell.

34. The method of claim 33, wherein said imaging is accomplished with computed tomography, computed radiography, magnetic resonance imaging, fluorescence microscopy, angiography, arteriography, nuclear imaging or a combination thereof.

35. A method of imaging a cell, the method comprising the steps of contacting a cell with the amphiphilic polymer of claim 16, wherein the polymer comprises a labeling agent, and imaging said cell, whereby said polymer enables the imaging of said cell.

36. A method of targeted delivery of at least one agent in a subject comprising the steps of administering to said subject the amphiphilic polymer of claim 1, wherein said polymer comprises said agent and a targeting moiety.

37. The method of claim 36, wherein the agent is a drug.

38. The method of claim 36, wherein the polymer comprises at least two agents, wherein a first agent is a drug and a second agent is a labeling agent.

39. A method of targeted delivery of at least one agent in a subject comprising the steps of administering to said subject the amphiphilic polymer of claim 16, wherein said polymer comprises said agent and a targeting moiety.

40. The method of claim 39, wherein the agent is a drug.

41. The method of claim 39, wherein the polymer comprises at least two agents, wherein a first agent is a drug and a second agent is a labeling agent.

\* \* \* \* \*

UNITED STATES PATENT AND TRADEMARK OFFICE
CERTIFICATE OF CORRECTION

PATENT NO. : 8,349,991 B2
APPLICATION NO. : 11/405012
DATED : January 8, 2013
INVENTOR(S) : Clark K. Colton It is certified that error appears in the above-identified patent and that said Letters Patent is hereby corrected as shown below:

Col. 2, Line 3, item [56] (Other Publications), delete "Scienc" and insert -- Science --, therefor.

Col. 2, Line 27, item [56] (Other Publications), delete "functinalized" and insert -- functionalized --, therefor.

Col. 78, Line 12, in Claim 1, after "group," delete "t,".

Col. 80, Line 15, in Claim 16, delete "agent" and insert -- agent, --, therefor.

Col. 80, Lines 58-66, in Claim 18, delete

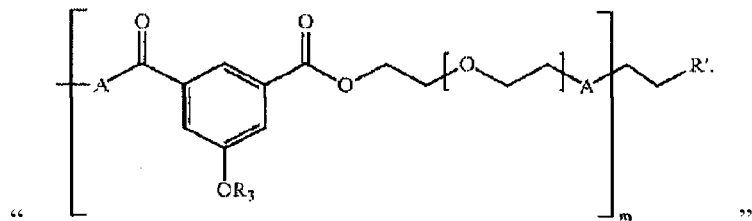

and insert

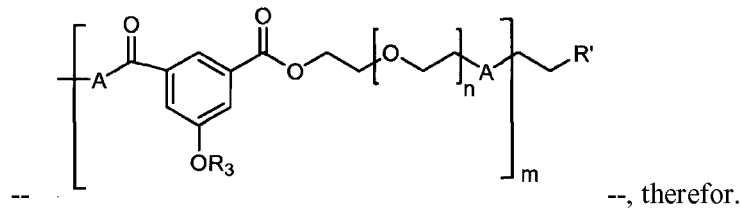   --, therefor.

Signed and Sealed this
Ninth Day of April, 2013

Teresa Stanek Rea
*Acting Director of the United States Patent and Trademark Office*